(12) United States Patent
Sahin et al.

(10) Patent No.: US 9,453,260 B2
(45) Date of Patent: Sep. 27, 2016

(54) GENETIC PRODUCTS DIFFERENTIALLY EXPRESSED IN TUMORS AND USE THEREOF

(71) Applicant: Ganymed Pharmaceuticals AG, Mainz (DE)

(72) Inventors: Ugur Sahin, Mainz (DE); Özlem Türeci, Mainz (DE); Michael Koslowski, Mainz (DE)

(73) Assignee: GANYMED PHARMACEUTICALS AG, Mainz (DE)

( * ) Notice: Subject to any disclaimer, the term of this patent is extended or adjusted under 35 U.S.C. 154(b) by 0 days.

(21) Appl. No.: 14/268,160

(22) Filed: May 2, 2014

(65) Prior Publication Data
US 2015/0031025 A1     Jan. 29, 2015

Related U.S. Application Data

(60) Division of application No. 12/197,960, filed on Aug. 25, 2008, now Pat. No. 8,716,455, which is a continuation of application No. 10/506,443, filed as application No. PCT/EP03/02556 on Mar. 12, 2003, now Pat. No. 7,429,461.

(30) Foreign Application Priority Data

Mar. 12, 2002 (DE) .................. 102 11 088

(51) Int. Cl.
| | | |
|---|---|---|
| *G01N 33/574* | (2006.01) | |
| *C12Q 1/68* | (2006.01) | |
| *C07K 14/47* | (2006.01) | |
| *C07K 16/30* | (2006.01) | |
| *A61K 39/395* | (2006.01) | |
| *A61K 38/00* | (2006.01) | |
| *A61K 39/00* | (2006.01) | |
| *A61K 48/00* | (2006.01) | |

(52) U.S. Cl.
CPC ....... *C12Q 1/6886* (2013.01); *A61K 39/39558* (2013.01); *C07K 14/4748* (2013.01); *C07K 16/30* (2013.01); *A61K 38/00* (2013.01); *A61K 39/00* (2013.01); *A61K 48/00* (2013.01); *C12Q 2600/112* (2013.01); *C12Q 2600/158* (2013.01); *G01N 33/574* (2013.01)

(58) Field of Classification Search
None
See application file for complete search history.

(56) References Cited

U.S. PATENT DOCUMENTS

| 5,869,045 A | 2/1999 | Hellstrom et al. |
| 2003/0017480 A1 | 1/2003 | Ota et al. |
| 2004/0058341 A1 | 3/2004 | Tang et al. |
| 2004/0180002 A1 | 9/2004 | Young et al. |

FOREIGN PATENT DOCUMENTS

| EP | 0 270 056 | 6/1988 |
| EP | 2 143 437 A1 | 1/2010 |
| JP | 2012/238202 | 10/2012 |
| WO | WO 92/04381 | 3/1992 |
| WO | WO 96/33265 | 10/1996 |
| WO | WO 96/33739 | 10/1996 |
| WO | WO 01/09345 | 2/2001 |
| WO | 01/75067 A2 | 10/2001 |
| WO | WO 02/10363 | 2/2002 |
| WO | WO 02/068579 | 9/2002 |
| WO | 02/078516 A2 | 10/2002 |

OTHER PUBLICATIONS

Chen et al, Hum Genet, 1999, 105:399-409.*
Kratzschmar et al. (Eur. J. Biochem., 236, 827-836, 1996).
L-lactate dehydrogenase C chain (EC 1.1.1.27), LDHC Human; EBI Database accession No. P07864, at http://www.uniprot.org/uniprot/P07864, entered Aug. 1, 1988.
Martelange et al., Cancer Res. 60(14):3848-3855, 2000.
Lethe et al., Int'l J. Cancer 76(6):903-908, 1998.
Lucas et al., Cancer Res. 58(4):743-752, 1998.
Bera et al., PNAS 99(5):3058-3063, 2002.
Koslowski et al., Cancer Res. 62(22) :6750-6755, 2002.
Pardoll, Nat. Med. 4:525-31, 1998.
Van Der Bruggen et al., Science 254:1643-7, 1991.
Sahin et al., Curr. Opin. Immunol. 9:709-16, 1997.
Tureci et al, Mol Med Today. 3:342-9, 1997.
Chen & Old, Cancer J. Sci. Am. 5:16-7, 1999.
Marchand et al., Int. J. Cancer 80:219-30, 1999.
Knuth et al., Cancer Chemother. Pharmacol. 46:p. 46-51, 2000.
Schmitt et al., Nucleic Acids Res. 27:4251-60, 1999.
Vasmatzis et al., Proc . Natl. Acad. Sci. USA. 95:300-4, 1998.
Scheurle et al., Cancer Res. 60:4037-43, 2000.
Altman et al., Science 274:94-96, 1996.
Dunbar et al., Curr. Biol. 8:413-416, 1998.
Greenberg, J. Immunol. 136(5):1917, 1986.
Riddel et al., Science 257:238, 1992.
Lynch et al., Eur. J. Immunol. 21:1403-1410, 1991.
Kast et al., Cell 59:603-614, 1989.
Stanislawski et al., Nat Immunol. 2:962-70, 2001.
Kessels et al., Nat Immunol. 2:957-61, 2001).
Ossendorp et al., Immunol Lett. 74:75-9, 2000.
Ossendorp et al., J. Exp. Med. 187:693-702, 1998.
Maloy et al., Proc Natl Acad Sci USA 98:3299-303, 2001.
Keogh et al., J. Immunol. 167:787-96, 2001.
Appella et al., Biomed Pept Proteins Nucleic Acids 1:177-84, 1995.
Wentworth et al., Mol Immunol. 32:603-12, 1995.
So et al., Mol. Cells 7:178-186, 1997.
Kreig et al., Nature 374:546-9, 1995.

(Continued)

*Primary Examiner* — Mark Halvorson
(74) *Attorney, Agent, or Firm* — McAndrews, Held & Malloy, Ltd.

(57) ABSTRACT

The invention relates to the identification of genetic products that are expressed in association with a tumor and the nucleic acid coding therefor. The invention relates to the therapy and diagnosis of diseases in which said genetic products that are expressed in association with a tumor are expressed in aberrant manner. The invention also relates to proteins, polypeptides, and peptides which are expressed in association with a tumor and the nucleic acids coding therefor.

8 Claims, 16 Drawing Sheets

(56) References Cited

OTHER PUBLICATIONS

Figure 1:
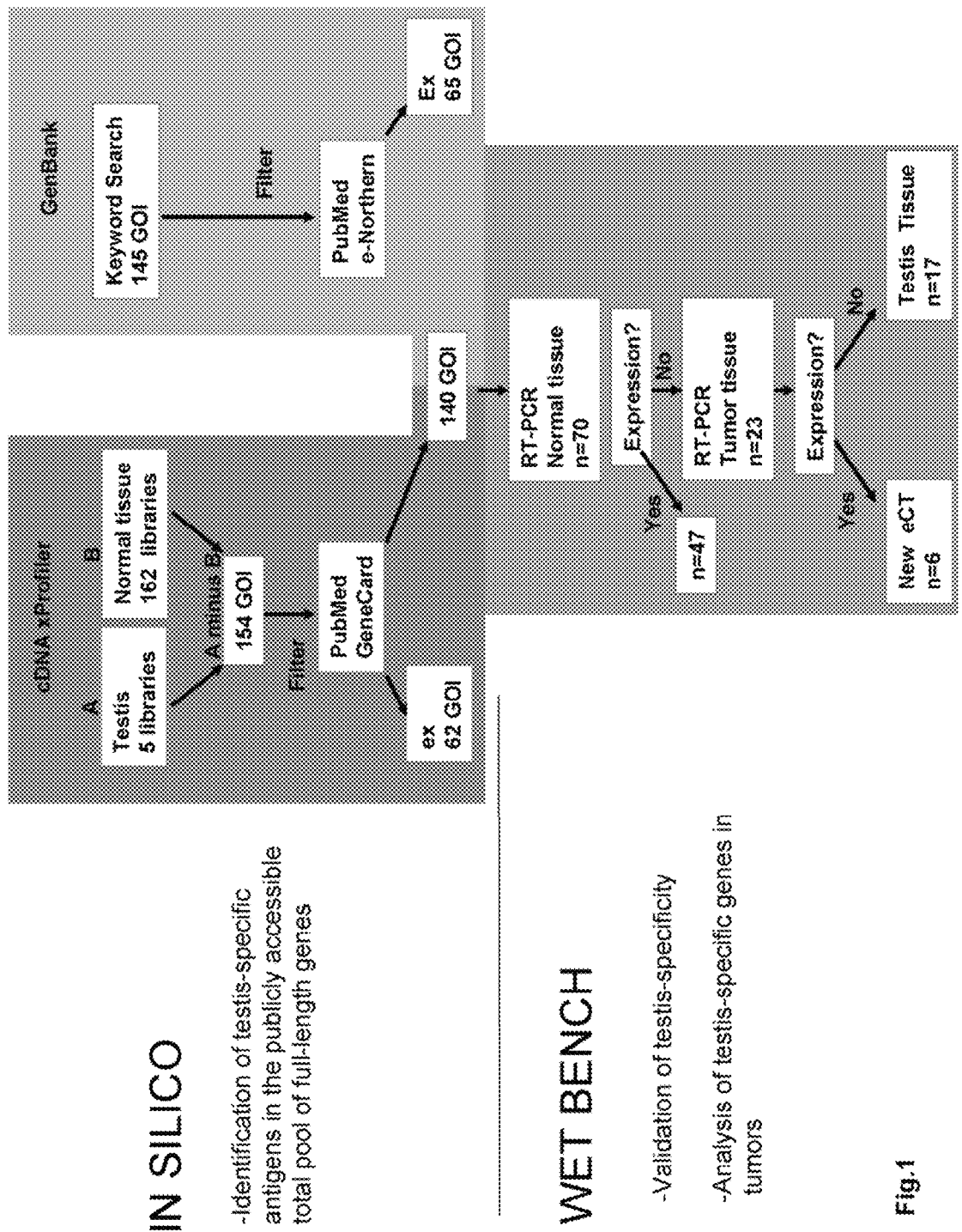

Hall, Science 268:1432-1434, 1995.
Zheng, P, et al., Proc. Natl. Acad. Sci., USA 95(11):6284-6289 (1998).
Gajewski et al., J. Immunol.154:5637-5648 (1995).
Ridge et al., Nature 393:474 (1998).
Bennett et al., Nature 393:478 (1998).
Schonberger et al., Nature 393:480 (1998).
Adams et al., Science 252:1651, 1991.
Gura, Science, 1997, 278:1041-1042.
Hillier et al., Genome Research 6:807-828, 1996.
Pennisi, Science 276:1023-1024, 1997.
Chomczynski & Sacchi, Anal. Biochem. 162:156-9, 1987.
Goldberg, E. et al., Contraception 64(2):93-8, 2001.
Cooker et al., Biol. Reprod. 48(6):1309-19, 1993.
Gupta, G.S., Crit. Rev. Biochem. Mol. Biol. 34(6):361-85, 1999.
Walker, S.M. et al., Biochem. J. 360(Pt 2):277-83, 2001.
Guioponi M. et al., Hum. Genet. 107(2):127-31, 2000.
Chen H. et al., Hum. Genet. 105(5):399-409, 1999.
Iijima and Devreotes, Cell 109:599-610, 2002.
White et. al., Annu Rev. Med., 52:125-145, 2001.
Stammers M. et al., Immunogenetics 51(4-5):373-82, 2000.
Liang Y. et al., Immunogenetics 53(5):357-68, 2001.
Liang Y. & Tedder, Genomics 72(2):119-27, 2001.
Jager D. et al., Cancer Res. 61(5):2055-61, 2001.
O'Bryan M. K., et al., Mol. Reprod. Dev. 58(1):116-25, 2001.
Maeda T. et al., Dev. Growth Differ. 41(6):715-22, 1999.
Kjeldsen et al., FEBS Lett 380:246-250, 1996.
Inoue et al., Hum. Mol. Genet. Jul:8(7):1201-7, 1999.
Roitt et al., Immunology, Fourth Edition, 1996, Mosby, p. 7.9-7.11.
Millan et al., PNAS 84:5311-5315, 1987.
Tapparael et al., Gene 323:189-199, 2003.
Tockman et al., Cancer Res. 52:2711s-2718s, 1992.
Greenberg et al., Genome Biology 4(9):117.1-117.8, 2003.
Clark W.R. (1986), The Experimental Foundations of Modern Immunology, Wiley & Sons, Inc., New York.
Roitt I (1991), Essential Immunology, 7th Edition, Blackwell Scientific Publications, Oxford.
Goodman and Gilman, "The Pharmacological Basis of Thereapeutics", 8th Edition, 1990, McGraw-Hill, Inc., in particular Chapter 52 (Antineoplastic Agents (Paul Calabrese and Bruce A. Chabner).
Sambrook et al., Molecular Cloning: A Laboratory Manual, 2nd Edition (1989) Cold Spring Harbor Laboratory Press, Cold Spring Harbor, N.Y.
International Search Report Corresponding to International Application Serial No. PCT/EP03/02556, mailed Jan. 23, 2004.
Non-Final Office Action dated May 12, 2010 in U.S. Appl. No. 12/197,960.
Final Office Action dated Dec. 22, 2010 in U.S. Appl. No. 12/197,960.
Non-Final Office Action dated Jan. 6, 2010 in U.S. Appl. No. 12/197,956.
Non-Final Office Action dated Jun. 23, 2010 in U.S. Appl. No. 12/197,956.
Final Office Action dated Feb. 19, 2011 in U.S. Appl. No. 12/197,956.
Hopp and Woods, Proc. Natl. Acad. Sci. USA, 1981, 78:3824-3828.
Database EMBL [Online], Apr. 12, 1996, "*H. sapiens* mRNA for cysteine-rich secretory protein-2/type I", gefunden im EBI accession No. EMBL:X95239, Database accession No. X95239.
Database Geneseq [Online], Feb. 13, 2002, "Novel human diagnostic protein—No. 6647", gefunden im EBI accession No. GSP:ABG06656, Database accession No. ABG06656.
Database Geneseq [Online], Feb. 13, 2002, gefunden im EBI accession No. GSN:AAS92411, Database accession No. AAS92411.
Kraetzschmar J et al: "The Human Cysteine-Rich Secretory Protein (CRISP) Family Primary Structure and Tissue Distribution of CRISP-1, CRISP-2 and CRISP-3", European Journal of Biochemistry, Blackwell Publishing, Berli, DE, vol. 236, No. 3, Mar. 15, 1996, pp. 827-836.
Database EMBL [Online], Sep. 9, 1998, "*Homo sapiens* putative tyrosine phosphatase mRNA, complete cds.", gefunden im EBI accession No. EMBL:AF007118, Database accession No. AF007118.
Database Geneseq [Online], "Human protein phosphatase 1 (PP1) protein sequence.", gefunden im EBI accession No. GSP:AAU75783, Database accession No. AAU75783.
Database GenBank [online], Accession No. NM_017448, <http://www.ncbi.nlm.nih.gov/entrez/viewer.fcgi?9257227:OLD03:593763> Nov. 2, 2000 uploaded, Definition: *Homo sapiens* lactate dehydrogenase C (LDHC), transcript variant 2, mRNA.
Database GenBank [online], Accession No. NM_013315, <http://www.ncbi.nlm.nih.gov/entrez/viewer.fcg?7019558:OLD03:593731> Nov. 2, 2000 uploaded, Definition: *Homo sapiens* transmembrane phosphatase with tensin homology (TPTE), mRNA.
Database GenBank [online], Accession No. NM_006781, <http://www.ncbi.nlm.nih.gov/entrez/viewer.fcgi?11321623:OLD03:2738164> Jun. 22, 2001 uploaded, Definition: *Homo sapiens* chromosome 6 open reading frame 10 (C6orf10), mRNA.
Database GenBank [online], Accession No. MM_017716, <http://www.ncbi.nlm.nih.gov/entrez/viewer.fcgi?8923205:OLD02:2717279> Feb. 10, 2002 uploaded, Definition: *Homo sapiens* membrane-spanning 4-domains, subfamily A, member 124-domains, subfamily A, member 7 (MS4A12), mRNA.
Mendelsohn , J. et al.: "The EGF receptor family as targets for cancer therapy", Oncogene (2000) 19, 6550-6565.
Jones JI et al., Prog Growth Factor Res. 1995; 6(2-4):319-27, Abstract.
Pilkington GJ et al., Anticancer Res. 1997; 17(6B):4107-9, Abstract.
Liu QJ and Gao B, Cell Mol Immunol. 2008; 5(3):171-82, p. 175.
Storkus WJ et al., Crit Rev Immunol. 2007; 27(5):485-93, Abstract.
Shaw LM, Methods Mol Biol. 2005; 294:97-105, Abstract.
Ying Zhan, 2008, Journal of International Biotechnology Law 5(1):34-36.
Bhattacharjee et al. 2001.

\* cited by examiner

Figure 3

Lactate dehydrogenase, active site (framed)
Tumor-specific epitopes (bold type)

```
SEQ_ID_19   MNESPDPTDLAGVIIELGPNDSPQTSEFKGATEEAPAKESPHTSEFKGAARVSPISESVL 60
SEQ_ID_20   MNESPDPTDLAGVIIELGPNDSPQTSEFKGATEEAPAKES------------------VL 42
SEQ_ID_21   MNESPDPTDLAGVIIELGPNDSPQTSEFKGATEEAPAKESPHTSEFKGAARVSPISESVL 60
SEQ_ID_58   MNESPDPTDLAGVIIELGPNDSPQTSEFKGATEEAPAKESPHTSEFKGAARVSPISESVL 60
SEQ_ID_59   MNESPDPTDLAGVIIELGPNDSPQTSEFKGATEEAPAKESPHTSEFKGAARVSPISESVL 60
SEQ_ID_60   MNESPDPTDLAGVIIELGPNDSPQTSEFKGATEEAPAKES------------------VL 42
SEQ_ID_61   MNESPDPTDLAGVIIELGPNDSPQTSEFKGATEEAPAKES------------------VL 42

SEQ_ID_19   ARLSKFEVEDAENVASYDSKIKKIVHSIVSSFAFGLFGVFLVLLDVTLILADLIFTDSKL 120
SEQ_ID_20   ARLSKFEVEDAENVASYDSKIKKIVHSIVSSFAFGLFGVFLVLLDVTLILADLIFTDSKL 102
SEQ_ID_21   ARLSKFEVEDAENVASYDSKIKKIVHSIVSSFAFGLFGVFLVLLDVTLILADLIFTDSKL 120
SEQ_ID_58   ARLSKFEVEDAENVASYDSKIKKIVHSIVSSFAFGLFGVFLVLLDVTLILADLIFTDSKL 120
SEQ_ID_59   ARLSKFEVEDAENVASYDSKIKKIVHSIVSSFAFGLFGVFLVLLDVTLILADLIFTDSKL 120
SEQ_ID_60   ARLSKFEVEDAENVASYDSKIKKIVHSIVSSFAFGLFGVFLVLLDVTLILADLIFTDSKL 102
SEQ_ID_61   ARLSKFEVEDAENVASYDSKIKKIVHSIVSSFAFGLFGVFLVLLDVTLILADLIFTDSKL 102

SEQ_ID_19   YIPLEYRSISLAIALFFLMDVLLRVFVERRQQYFSDLFNILDTAIIVILLLVDVVYIFFD 180
SEQ_ID_20   YIPLEYRSISLAIALFFLMDVLLRVFVERRQQYFSDLFNILDTAIIVILLLVDVVYIFFD 162
SEQ_ID_21   YIPLEYRSISLAIALFFLMDVLLRVFVERRQQYFSDLFNILDTAIIVILLLVDVVYIFFD 180
SEQ_ID_58   YIPLEYRSISLAIALFFLMDVLLRVFVERRQQYFSDLFNILDTAIIVILLLVDVVYIFFD 180
SEQ_ID_59   YIPLEYRSISLAIALFFLMDVLLRVFVERRQQYFSDLFNILDTAIIVILLLVDVVYIFFD 180
SEQ_ID_60   YIPLEYRSISLAIALFFLMDVLLRVFVERRQQYFSDLFNILDTAIIVILLLVDVVYIFFD 162
SEQ_ID_61   YIPLEYRSISLAIALFFLMDVLLRVFVERRQQYFSDLFNILDTAIIVILLLVDVVYIFFD 162

SEQ_ID_19   IKLLRNIPRWTHLLRLLRLIILLRIFHLFHQKRQLEKLIRRRVSENKRRYTRDGFDLDLT 240
SEQ_ID_20   IKLLRNIPRWTHLLRLLRLIILLRIFHLFHQKRQLEKLIRRRVSENKRRYTRDGFDLDLT 222
SEQ_ID_21   IKLLRNIPRWTHLLRLLRLIILLRIFHLFHQKRQLEKLIRRRVSENKRRYTRDGFDLDLT 240
SEQ_ID_58   IKLLRNIPRWTHLLRLLRLIILLRIFHLFHQKRQLEKLIRRRVSENKRRYTRDGFDLDLT 240
SEQ_ID_59   IKLLRNIPRWTHLLRLLRLIILLRIFHLFHQKRQLEKLIRRRVSENKRRYTRDGFDLDLT 240
SEQ_ID_60   IKLLRNIPRWTHLLRLLRLIILLRIFHLFHQKRQLEKLIRRRVSENKRRYTRDGFDLDLT 222
SEQ_ID_61   IKLLRNIPRWTHLLRLLRLIILLRIFHLFHQKRQLEKLIRRRVSENKRRYTRDGFDLDLT 222

SEQ_ID_19   YVTERIIAMSFPSSGRQSFYRNPIKEVVRFLDKKHRNHYRVYNLCS-------------- 286
SEQ_ID_20   YVTERIIAMSFPSSGRQSFYRNPIKEVVRFLDKKHRNHYRVYNLCS-------------- 268
SEQ_ID_21   YVTERIIAMSFPSSGRQSFYRNPIKEVVRFLDKKHRNHYRVYNLCSMYITLYCATVDRKQ 300
SEQ_ID_58   YVTERIIAMSFPSSGRQSFYRNPIKEVVRFLDKKHRNHYRVYNLCS-------------- 286
SEQ_ID_59   YVTERIIAMSFPSSGRQSFYRNPIKEVVRFLDKKHRNHYRVYNLCS-------------- 286
SEQ_ID_60   YVTERIIAMSFPSSGRQSFYRNPIKEVVRFLDKKHRNHYRVYNLCS-------------- 268
SEQ_ID_61   YVTERIIAMSFPSSGRQSFYRNPIKEVVRFLDKKHRNHYRVYNLCS-------------- 268

SEQ_ID_19   ----ERAYDPKHFHNRVVRIMIDDHNVPTLHQMVVFTKEVNEWMAQDLENIVAIHCKGGT 342
SEQ_ID_20   ----ERAYDPKHFHNRVVRIMIDDHNVPTLHQMVVFTKEVNEWMAQDLENIVAIHCKGGT 324
SEQ_ID_21   ITARERAYDPKHFHNRVVRIMIDDHNVPTLHQMVVFTKEVNEWMAQDLENIVAIHCKGGT 360
SEQ_ID_58   ----ERAYDPKHFHNRVVRIMIDDHNVPTLHQMVVFTKEVNEWMAQDLENIVAIHCKGGT 342
SEQ_ID_59   ----ERAYDPKHFHNRVVRIMIDDHNVPTLHQMVVFTKEVNEWMAQDLENIVAIHCKGGT 342
SEQ_ID_60   ----ERAYDPKHFHNRVVRIMIDDHNVPTLHQMVVFTKEVNEWMAQDLENIVAIHCKGGT 324
SEQ_ID_61   ----ERAYDPKHFHNRVVRIMIDDHNVPTLHQMVVFTKEVNEWMAQDLENIVAIHCKGGT 324

SEQ_ID_19   DRTGTMVCAFLIASEICSTAKESLYYFGERRTDKTHSEKFQGVETPSQKRYVAYFAQVKH 402
SEQ_ID_20   DRTGTMVCAFLIASEICSTAKESLYYFGERRTDKTHSEKFQGVETPSQKRYVAYFAQVKH 384
SEQ_ID_21   DRTGTMVCAFLIASEICSTAKESLYYFGERRTDKTHSEKFQGVETPSQKRYVAYFAQVKH 420
SEQ_ID_58   DRTGTMVCAFLIASEICSTAKESLYYFGERRTDKTHSEKFQGVETPSQMYVI-------- 395
SEQ_ID_59   G----------------------------------------------------------- 343
SEQ_ID_60   DRTGTMVCAFLIASEICSTAKESLYYFGERRTDKTHSEKFQGVETP-------------- 370
SEQ_ID_61   G----------------------------------------------------------- 325

SEQ_ID_19   LYNWNLPPRRILFIKHFIIYSIPRYVRDLKIQIEMEKKVVFSTISLGKCSVLDNITTDKI 462
SEQ_ID_20   LYNWNLPPRRILFIKHFIIYSIPRYVRDLKIQIEMEKKVVFSTISLGKCSVLDNITTDKI 444
SEQ_ID_21   LYNWNLPPRRILFIKHFIIYSIPRYVRDLKIQIEMEKKVVFSTISLGKCSVLDNITTDKI 480
SEQ_ID_58   ------------------------------------------------------------ 
SEQ_ID_59   -------------------------YVRDLKIQIEMEKKVVFSTISLGKCSVLDNITTDKI 379
SEQ_ID_60   ---------------------------------------------SVLDNITTDKI 381
SEQ_ID_61   -------------------------YVRDLKIQIEMEKKVVFSTISLGKCSVLDNITTDKI 361
```

Figure 6

```
SEQ_ID_19    LIDVFDGPPLYDDVKVQFFYSNLPTYYDNCSFYFWLHTSFIENNRLYLPKNELDNLHKQK 522
SEQ_ID_20    LIDVFDGPPLYDDVKVQFFYSNLPTYYDNCSFYFWLHTSFIENNRLYLPKNELDNLHKQK 504
SEQ_ID_21    LIDVFDGPPLYDDVKVQFFYSNLPTYYDNCSFYFWLHTSFIENNRLYLPKNELDNLHKQK 540
SEQ_ID_58    ------------------------------------------------------------
SEQ_ID_59    LIDVFDGPPLYDDVKVQFFYSNLPTYYDNCSFYFWLHTSFIENNRLYLPKNELDNLHKQK 439
SEQ_ID_60    LIDVFDGPPLYDDVKVQFFYSNLPTYYDNCSFYFWLHTSFIENNRLYLPKNELDNLHKQK 441
SEQ_ID_61    LIDVFDGPPLYDDVKVQFFYSNLPTYYDNCSFYFWLHTSFIENNRLYLPKNELDNLHKQK 421

SEQ_ID_19    ARRIYPSDFAVEILFGEKMTSSDVVAGSD 551
SEQ_ID_20    ARRIYPSDFAVEILFGEKMTSSDVVAGSD 533
SEQ_ID_21    ARRIYPSDFAVEILFGEKMTSSDVVAGSD 569
SEQ_ID_58    -----------------------------
SEQ_ID_59    ARRIYPSDFAVEILFGEKMTSSDVVAGSD 468
SEQ_ID_60    ARRIYPSDFAVEILFGEKMTSSDVVAGSD 470
SEQ_ID_61    ARRIYPSDFAVEILFGEKMTSSDVVAGSD 450
```

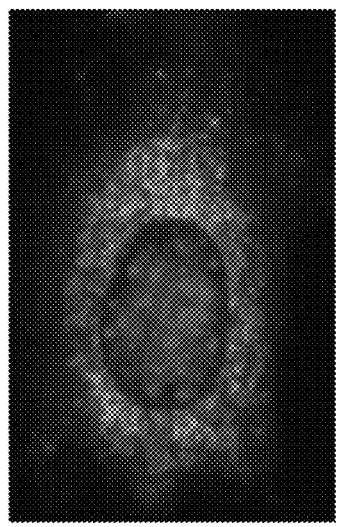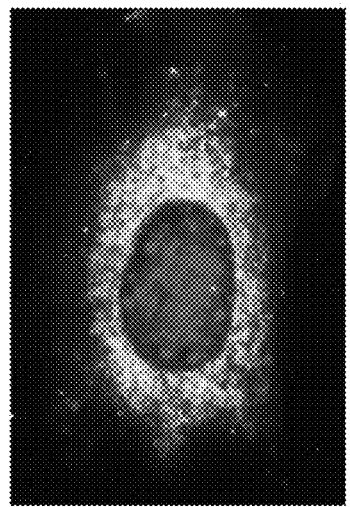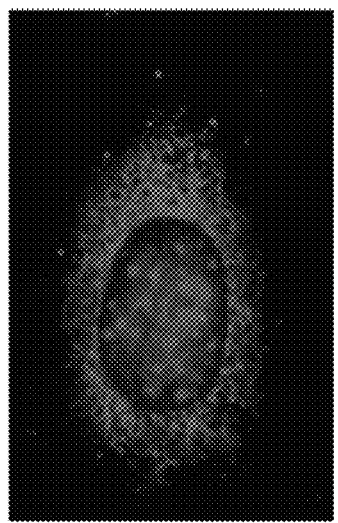
Fig. 12

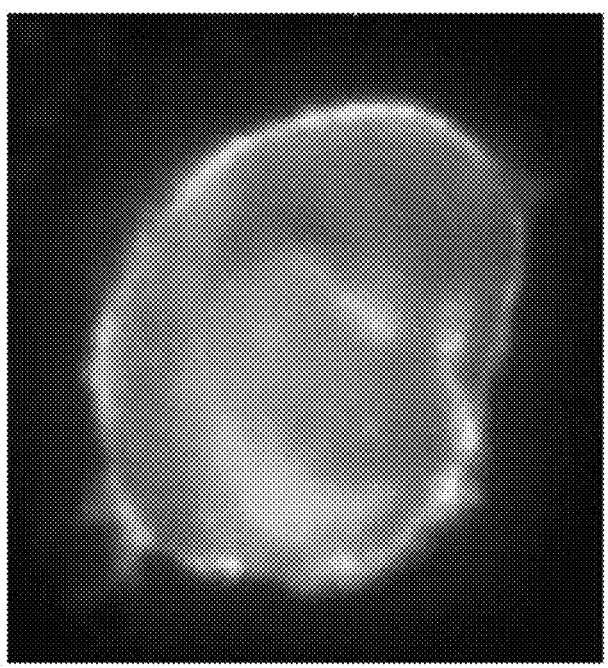
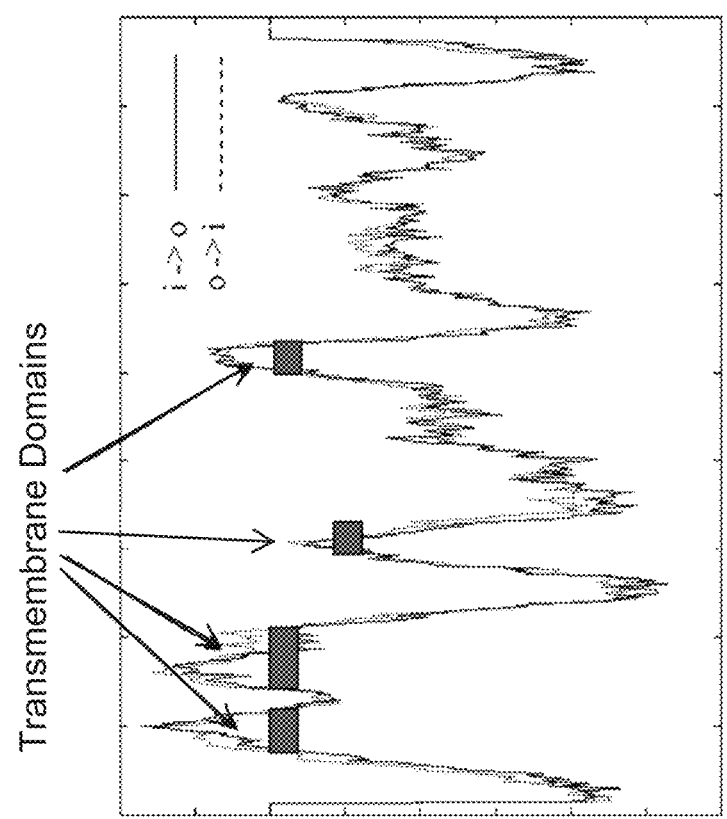
Fig. 13

US 9,453,260 B2

GENETIC PRODUCTS DIFFERENTIALLY EXPRESSED IN TUMORS AND USE THEREOF

RELATED APPLICATIONS

This application is a divisional application of U.S. patent application Ser. No. 12/197,960, filed on Aug. 25, 2008, now U.S. Pat. No. 8,716,455, which issued May 6, 2014, which is a continuation application of U.S. patent application Ser. No. 10/506,443, filed Sep. 2, 2004, now U.S. Pat. No. 7,429,461, which issued Sep. 30, 2008 and which is a National Stage Entry of PCT/EP03/02556, which was filed on Mar. 12, 2003 and claims priority to German Patent Application Number 102-11-088.3, which was filed on Mar. 13, 2002, all of which are incorporated herein by reference in their entireties.

SEQUENCE LISTING

This application includes a sequence listing, which is submitted upon filing in electronic form only (computer readable ".txt" file), and which is incorporated herein by reference in lieu of the paper copy of the sequence listing. The content of the electronic sequence listing and the paper copy of the sequence listing are the same.

BACKGROUND OF THE INVENTION

Despite interdisciplinary approaches and exhaustive use of classical therapeutic procedures, cancers are still among the leading causes of death. More recent therapeutic concepts aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced. Tumor cells biologically differ substantially from their non-malignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens. The specific recognition of tumor-associated antigens involves cellular and humoral mechanisms which are two functionally interconnected units: CD4$^+$ and CD8$^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998). Accordingly, a central aim of tumor immunology is to molecule/ly define these structures. The molecular nature of these antigens has been enigmatic for a long time. Only after development of appropriate cloning techniques has it been possible to screen cDNA expression libraries of tumors systematically for tumor-associated antigens by analyzing the target structures of cytotoxic T lymphocytes (CTL) (van der Bruggen at al., *Science* 254:1643-7, 1991) or by using circulating autoantibodies (Sahin et al., *Curr. Opin. Immunol.* 9:709-16, 1997) as probes. To this end, cDNA expression libraries were prepared from fresh tumor tissue and recombinantly expressed as proteins in suitable systems Immunoeffectors isolated from patients, namely CTL clones with tumor-specific lysis patterns, or circulating autoantibodies were utilized for cloning the respective antigens.

In recent years a multiplicity of antigens have been defined in various neoplasias by these approaches. The class of cancer/testis antigens (CTA) is of great interest here. CTA and genes encoding them (cancer/testis genes or CTG) are defined by their characteristic expression pattern [Tureci et al, *Mol Med Today.* 3:342-9, 1997]. They are not found in normal tissues, except testis and germ cells, but are expressed in a number of human malignomas, not tumor type-specifically but with different frequency in tumor entities of very different origins (Chen & Old, *Cancer J. Sci. Am.* 5:16-7, 1999). Serum reactivities against CTA are also not found in healthy controls but only in tumor patients. This class of antigens, in particular owing to its tissue distribution, is particularly valuable for immunotherapeutic projects and is tested in current clinical patient studies (Marchand at al., *Int. J. Cancer* 80:219-30, 1999; Knuth et al., *Cancer Chemother. Pharmacol.* 46:p 46-51, 2000).

However, the probes utilized for antigen identification in the classical methods illustrated above are immunoeffectors (circulating autoantibodies or CTL clones) from patients usually having already advanced cancer. A number of data indicate that tumors can lead, for example, to tolerlzation and anergization of T cells and that, during the course of the disease, especially those specificities which could cause effective immune recognition are lost from the immunoeffector repertoire. Current patient studies have not yet produced any solid evidence of a real action of the previously found and utilized tumor-associated antigens. Accordingly, it cannot be ruled out that proteins evoking spontaneous immune responses are the wrong target structures.

BRIEF SUMMARY OF THE INVENTION

It was the object of the present invention to provide target structures for a diagnosis and therapy of cancers.

According to the invention, this object is achieved by the subject matter of the claims.

BRIEF DESCRIPTIONS OF THE FIGURES

FIG. 1: Diagrammatic representation of the cloning of eCT. The strategy comprises identifying candidate genes (GOI="Genes of interest") in databases and testing said genes by means of RT-PCR.

Figure 2:
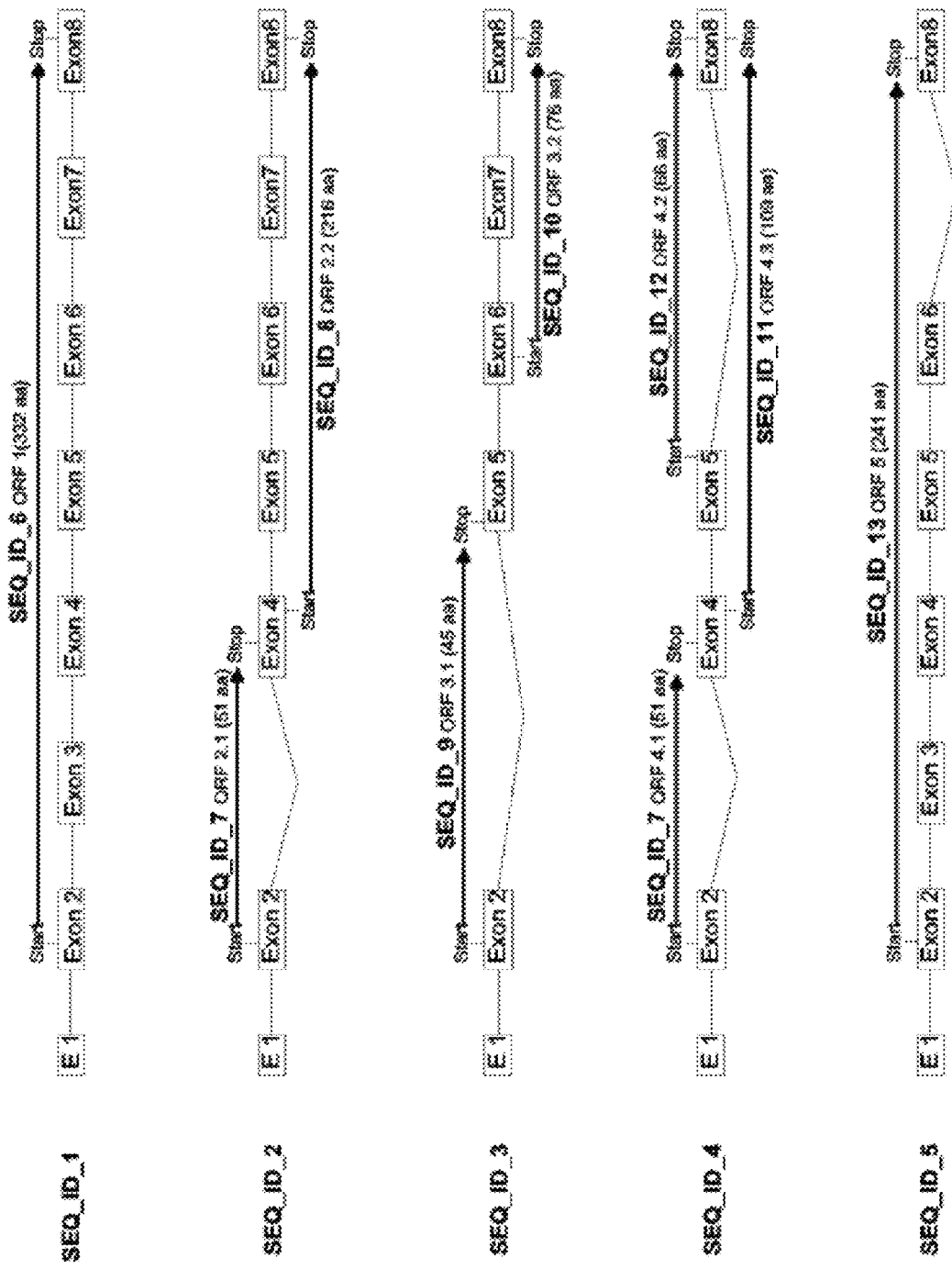

FIG. 2: Splicing of LDH C. Alternative splicing events result in the absence of exon 3 (SEQ ID NO:2), of the two exons 3 and 4 (SEQ ID NO:3), of the exons 3, 6 and 7 (SEQ ID NO:4) and of exon 7 (SEQ ID NO:5). ORF=open reading frame, as =amino acid.

FIG. 3: Alignment of possible LDH-C proteins. SEQ ID NO:8 and SEQ ID NO:10 are truncated portions of the prototype protein (SEQ ID NO:6). The protein sequences of SEQ ID NO:7, SEQ ID NO:9, SEQ ID NO:11, SEC ID NO:12 and SEQ ID NO:13 are additionally altered and contain only tumor-specific epitopes (printed in bold type). The catalytic centre is framed.

Figure 4:
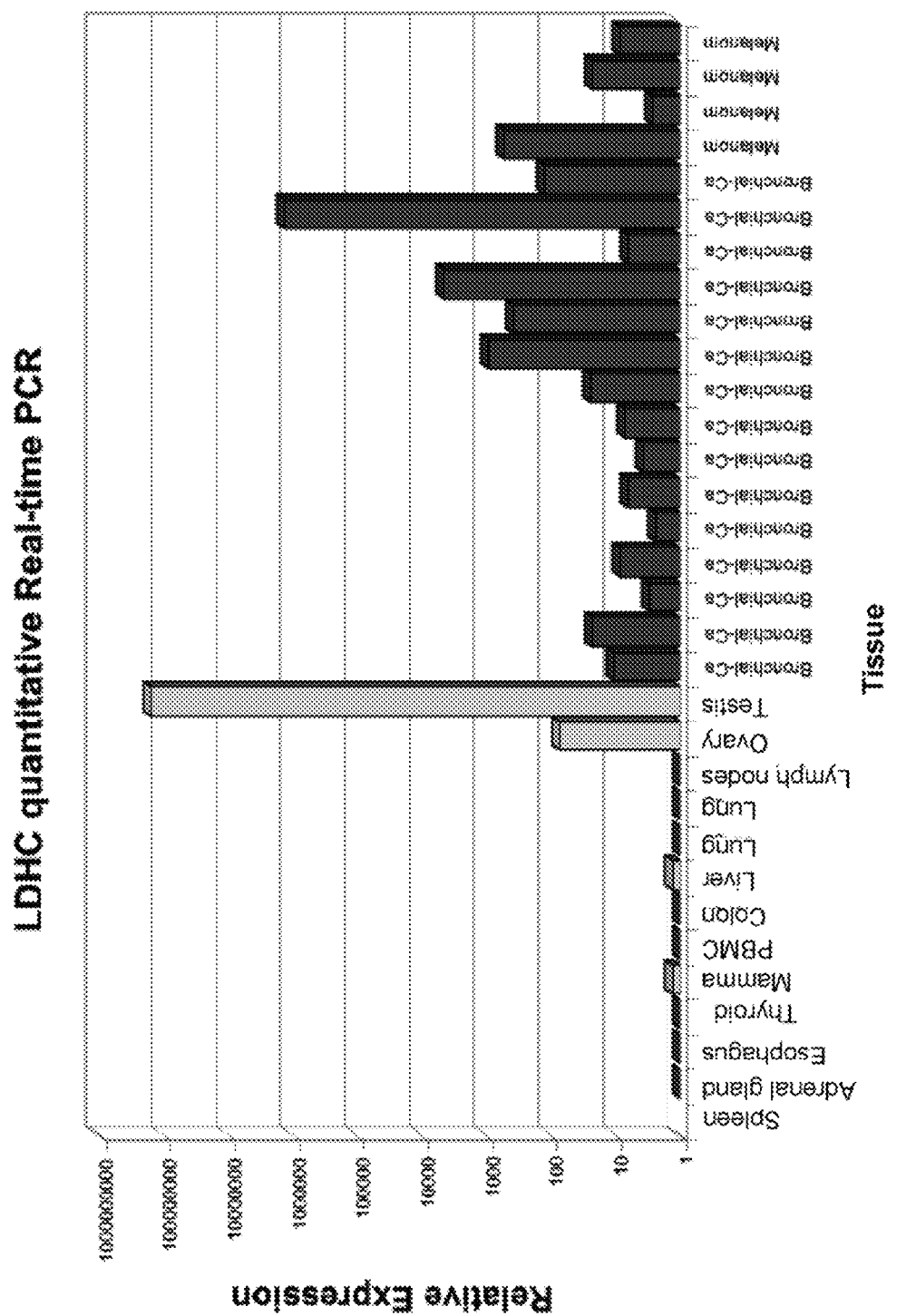

FIG. 4: Quantification of LDH C in various tissues by means of real time PCR. No transcripts were detected in normal tissues other than testis, but significant levels of expression were detected in tumors.

Figure 5:
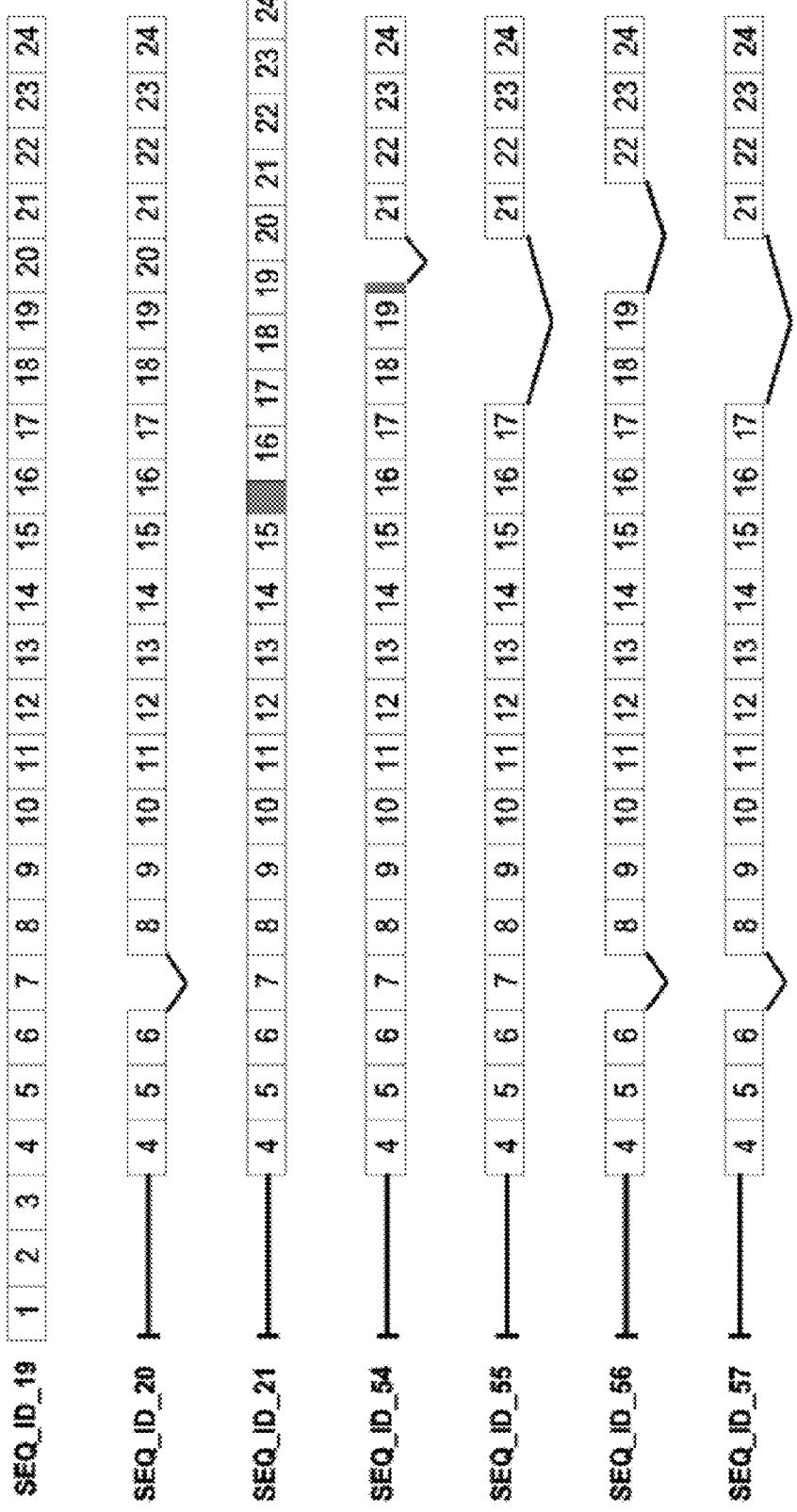

FIG. 5: Exon composition of TPTE variants. According to the invention, splice variants were identified (SEQ ID NO:20, SEQ ID NO:21, SEQ ID NO:54, SEQ ID NO:55, SEQ ID NO:56, SEQ ID NO:57) which are expressed in testicular tissues and in tumors and which have frame shifts and thus altered sequence regions.

FIG. 6: Alignment of the possible TPTE proteins. Alternative splicing events result in alterations of the encoded proteins, with the reading frame being retained in principle. The putative transmembrane domains are printed in bold type, the catalytic domain is framed.

Figure 7:
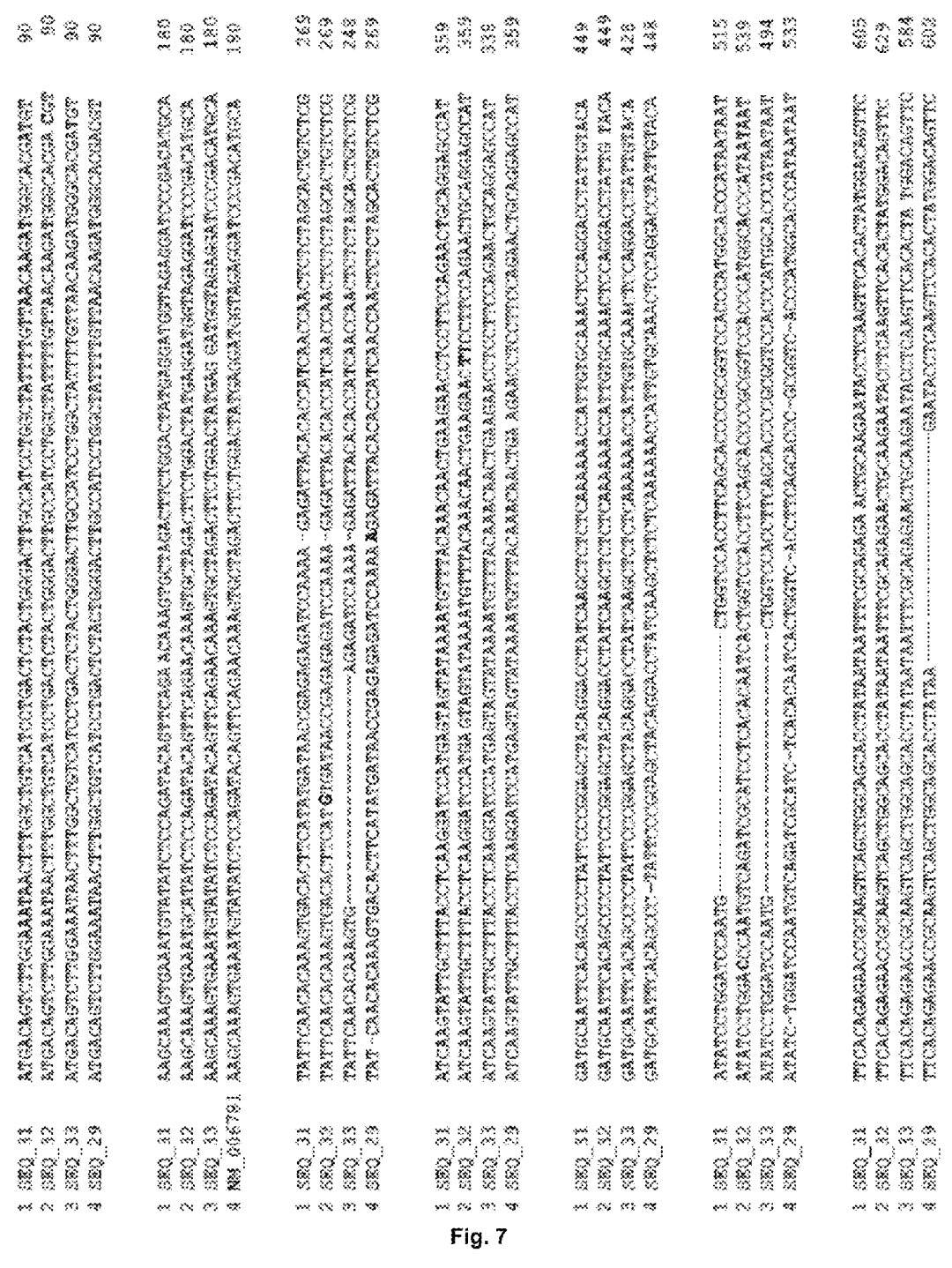
Figure 7:
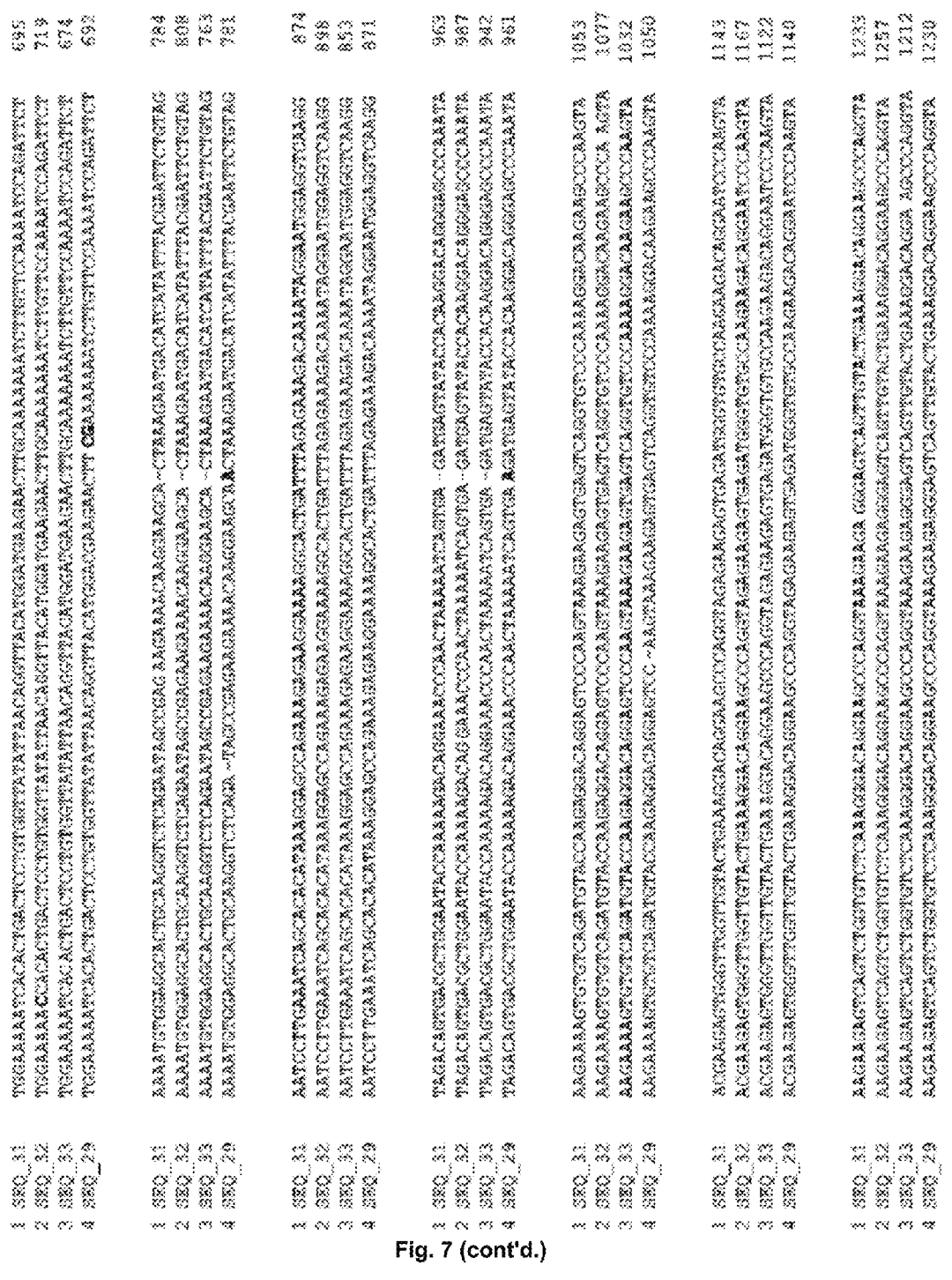

FIG. 7: Alignment of TSBP variants at the nucleotide level. The differences in the nucleotide sequences of the TSBP variants found according to the invention (SEQ) ID NO:31, SEQ ID NO:32, SEQ ID NO:33) to the known sequence (NM_006781, SEQ ID NO: 29) are printed in bold type.

Figure 8:
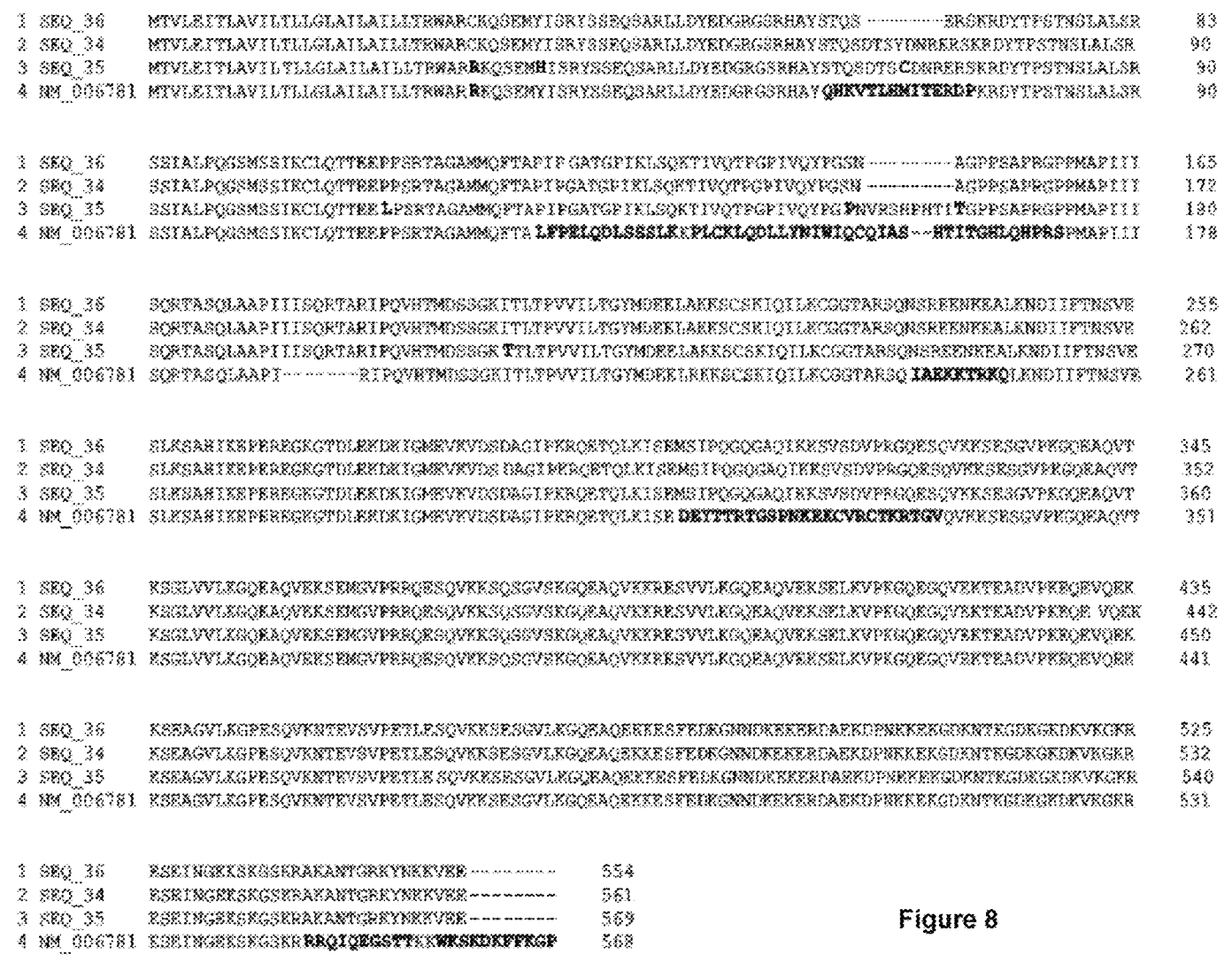

FIG. 8: Alignment of TSBP variants at the protein level. In the proteins encoded by the TSBP variants found according to the invention (SEQ ID NO:34, SEQ ID NO:35, SEQ ID NO:36), frame shifts cause substantial differences to the previously described protein (SEQ ID NO:30, NM_006781) and are indicated by bold type.

Figure 9:
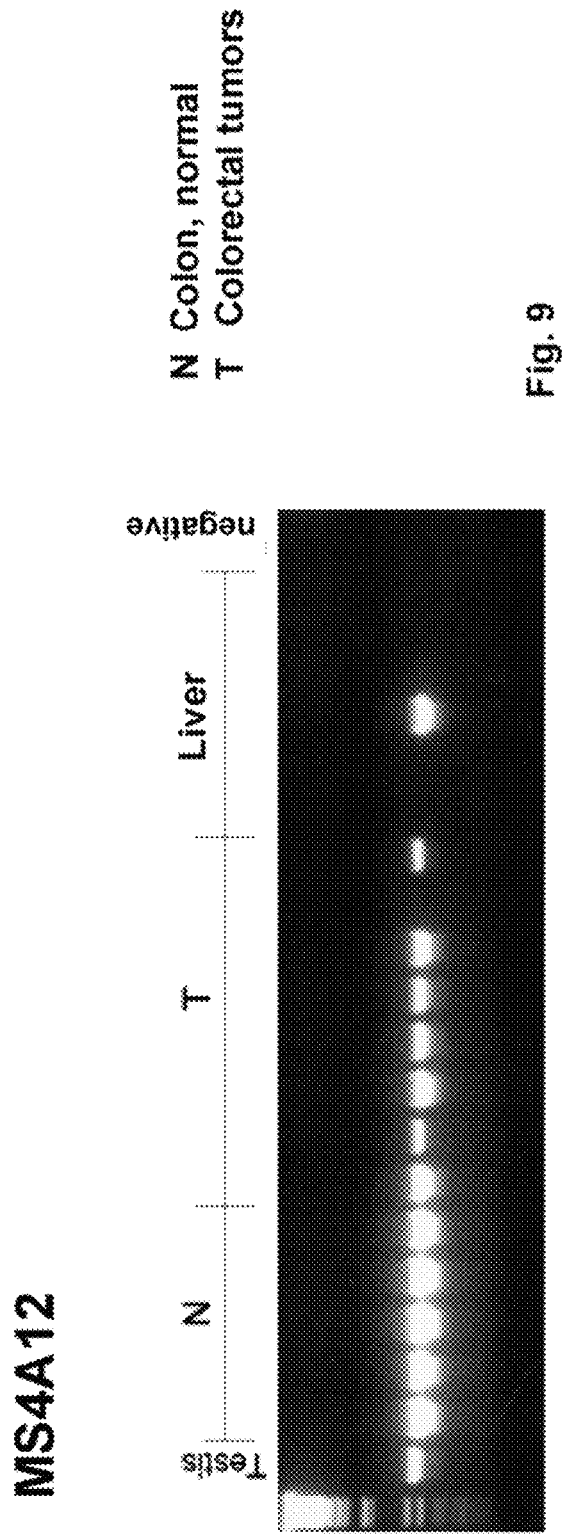

FIG. 9: RT-PCR for MS4A12. Expression was detected in the tissues tested only in testis, colon and colorectal carcinomas (colon ca's). In one of the 6 liver tissue samples shown, a positive detection was carried out for MS4A12, since this sample has been infiltrated by a colon carcinoma metastasis. Later studies also demonstrated distinct expression in colon carcinoma metastases.

Figure 10:
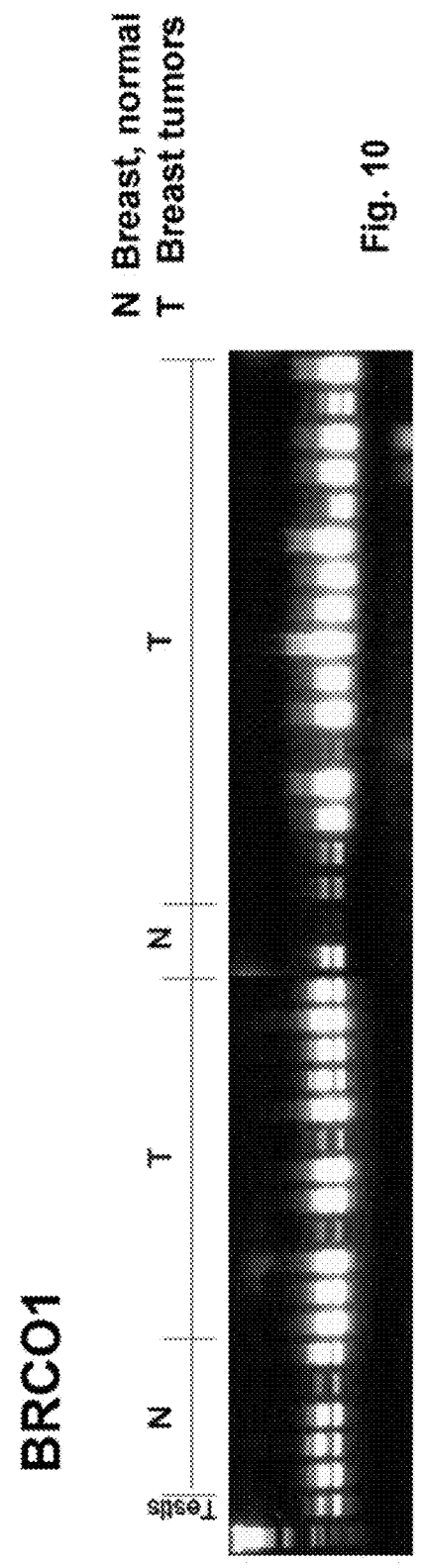

FIG. 10: RT-PCR for BRCO1. BRCO1 is distinctly overexpressed in breast tumors in comparison with expression in normal mammary gland tissue.

Figure 11:
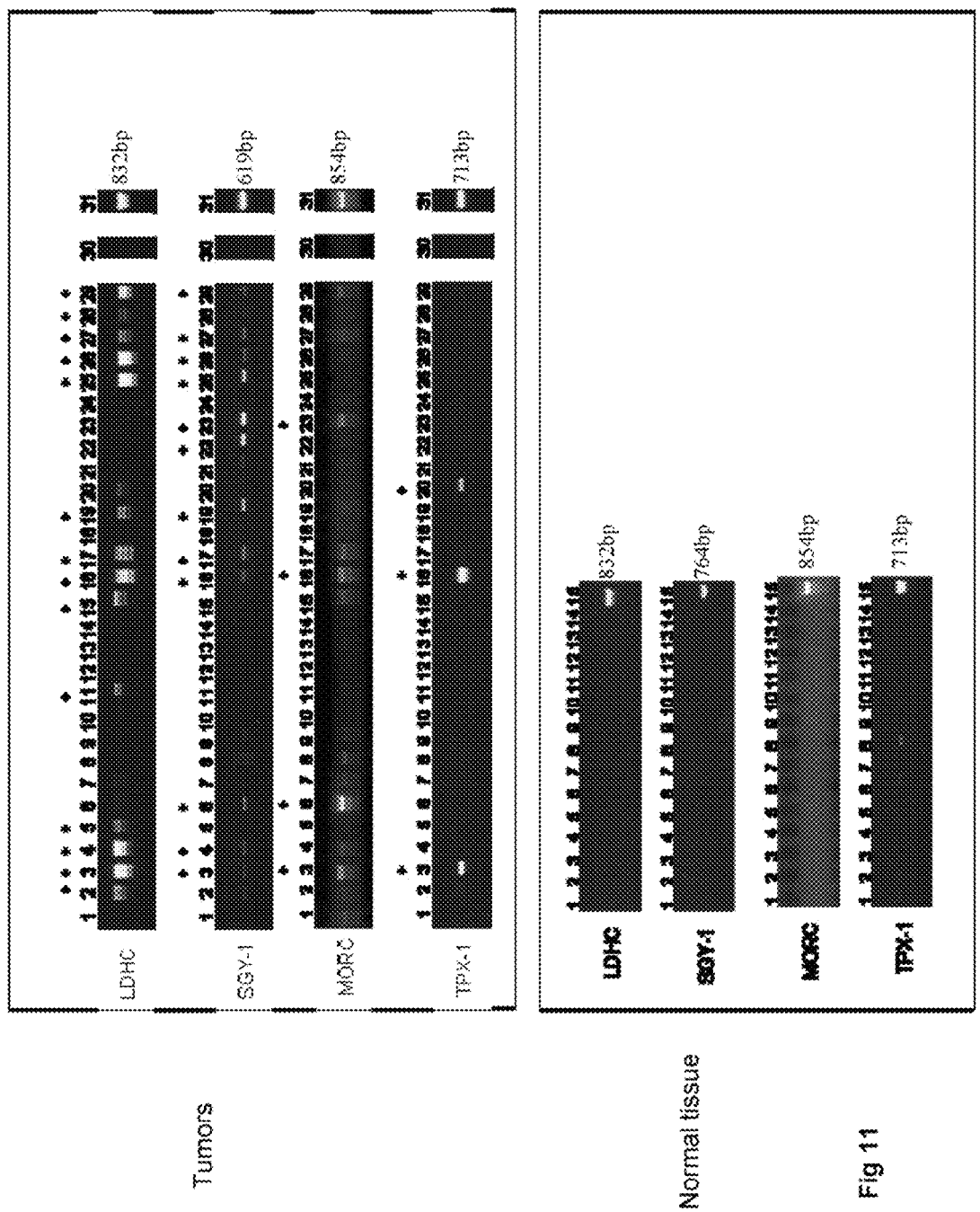

FIG. 11: RT-PCR for MORC, TPX1, LDHC, SGY-1. A study of various normal tissues reveals expression only in testis (1 skin, 2 small intestine, 3 colon, 4 liver, 5 lung, 6 stomach, 7 breast, 8 kidney, 9 ovary, 10 prostate, 11 thyroid, 12 leukocytes, 13 thymus, 14 negative control, 15 testis). The examination of tumors (1-17 lung tumors, 18-29 melanomas, 30 negative control, 31 testis) reveals ectopic expression in said tumors with different frequencies for the individual eCT.

FIG. 12: Mitochondrial localization of LDHC in the MCF-7 breast cancer cell line. MCF-7 cells were transiently transfected with an LDHC expression plasmid. The antigen was detected with LDHC-specific antibodies and showed distinct colocalization with the mitochondrial respiratory chain enzyme cytochrome C-oxidase.

FIG. 13: Predicted topology of TPTE and subcellular localization on the cell surface of MCF-7 cells. The diagram on the left-hand side depicts the 4 putative TPTE transmembrane domains (arrows). MCF-7 cells were transiently transfected with a TPTE expression plasmid. The antigen was detected using TPTE-specific antibodies and showed distinct colocalization with MHC I molecules located on the cell surface.

Figure 14:
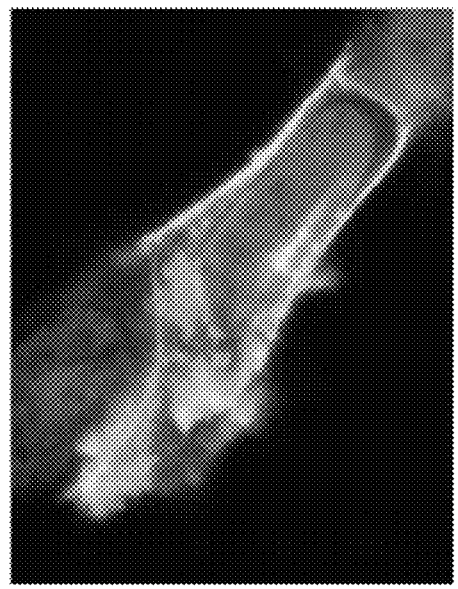

FIG. 14: MS4A12 localization on the cell membrane. Tumor cells were transiently transfected with a GFP-tagged MS4A12 construct and showed complete colocalization with plasma membrane markers in confocal immunofluorescence microscopy.

DETAILED DESCRIPTION OF THE INVENTION

According to the invention, a strategy for identifying and providing antigens expressed in association with a tumor and the nucleic acids coding therefor was pursued. This strategy is based on the fact that actually testis- and thus germ cell-specific genes which are usually silent in adult tissues are reactivated in tumor cells in an ectopic and forbidden manner. First, data mining produces a list as complete as possible of all known testis-specific genes which are then evaluated for their aberrant activation in tumors by expression analyses by means of specific RT-PCR. Data mining is a known method of identifying tumor-associated genes. In the conventional strategies, however, transcriptoms of normal tissue libraries are usually subtracted electronically from tumor tissue libraries, with the assumption that the remaining genes are tumor-specific (Schmitt et al., *Nucleic Acids Res.* 27:4251-60, 1999; Vasmatzis et al., *Proc. Natl. Acad. Sci. USA*. 95:300-4, 1998. Scheurle et al., *Cancer Res.* 60:4037-43, 2000).

The concept of the invention, which has proved much more successful, however, is based on utilizing data mining for electronically extracting all testis-specific genes and then evaluating said genes for ectopic expression in tumors.

The invention thus relates in one aspect to a strategy for identifying genes differentially expressed in tumors. Said strategy combines data mining of public sequence libraries ("in silico") with subsequent evaluating laboratory-experimental ("wet bench") studies.

According to the invention, a combined strategy based on two different bioinformatic scripts enabled new members of the cancer/testis (CT) gene class to be identified. These have previously been classified as being purely testis-, germ cell- or sperm-specific. The finding that these genes are aberrantly activated in tumor cells allows them to be assigned a substantially new quality with functional implications. According to the invention, these tumor-associated genes and the genetic products encoded thereby were identified and provided independently of an immunogenic action.

The tumor-associated antigens identified according to the invention have an amino acid sequence encoded by a nucleic; acid which is selected from the group consisting of (a) a nucleic acid which comprises a nucleic acid sequence selected from the group consisting of SEQ ID NOs: 1-5, 19-21, 29, 31-33, 37, 39, 40, 54-57, 62, 63, 70, 74, 85-88, a part or derivative thereof, b) a nucleic acid which hybridizes with the nucleic acid of (a) under stringent conditions, c) a nucleic acid which is degenerate with respect to the nucleic acid of (a) or (b), and (d) a nucleic acid which is complementary to the nucleic acid of (a), (b) or (c). In a preferred embodiment, a tumor-associated antigen identified according to the invention has an amino acid sequence encoded by a nucleic acid which is selected from the group consisting of SEQ ID NOs: 1-5, 19-21, 29, 31-33, 37, 39, 40, 54-57, 62, 63, 70, 74, 85-88. In a further preferred embodiment, a tumor-associated antigen identified according to the invention comprises an amino acid sequence selected from the group consisting of SEQ ID NOs: 6-13, 14-18, 22-24, 30, 34-36, 38, 41, 58-61, 64, 65, 71, 75, 80-84, 89-100, a part or derivative thereof.

The present invention generally relates to the use of tumor-associated antigens identified according to the invention or of parts thereof, of nucleic acids coding therefor or of nucleic acids directed against said coding nucleic acids or of antibodies directed against the tumor-associated antigens identified according to the invention or parts thereof for therapy and diagnosis. This utilization may relate to individual but also to combinations of two or more of these antigens, functional fragments, nucleic acids, antibodies, etc., in one embodiment also in combination with other tumor associated genes and antigens for diagnosis, therapy and progress control.

Preferred diseases for a therapy and/or diagnosis are those in which one or more of the tumor-associated antigens identified according to the invention are selectively expressed or abnormally expressed.

The invention also relates to nucleic acids and genetic products which are expressed in association with a tumor cell and which are produced by altered splicing (splice variants) of known genes or by altered translation with utilization of alternative open reading frames. Said nucleic acids comprise the sequences according to (SEQ ID NO: 2-5, 20, 21, 31-33, 54-57, 85-88) of the sequence listing. Furthermore, the genetic products comprise sequences according to (SEQ ID NO: 7-13, 23, 24, 34-36, 58-61, 89-100) of the sequence listing. The splice variants of the invention can be used according to the invention as targets for diagnosis and therapy of neoplastic diseases.

Very different mechanisms may cause splice variants to be produced, for example
  utilization of variable transcription initiation sites
  utilization of additional exons
  complete or incomplete splicing out of single or two or more exons,
  splice regulator sequences altered via mutation (deletion or generation of new donor/acceptor sequences),
  incomplete elimination of intron sequences.

Altered splicing of a gene results in an altered transcript sequence (splice variant). Translation of a splice variant in the region of its altered sequence results in an altered protein which may be distinctly different in the structure and function from the original protein. Tumor-associated splice variants may produce tumor-associated transcripts and tumor-associated proteins/antigens. These may be utilized as molecular markers both for detecting tumor cells and for therapeutic targeting of tumors. Detection of tumor cells, for example in blood, serum, bone marrow, sputum, bronchial lavage, bodily secretions and tissue biopsies, may be carried out according to the invention, for example, after extraction of nucleic acids by PCR amplification with splice variant-specific oligonucleotides. According to the invention, all sequence-dependent detection systems are suitable for detection. These are, apart from PCR, for example gene chip/microarray systems, Northern blot, RNAse protection assays (RDA) and others. All detection systems have in common that detection is based on a specific hybridization with at least one splice variant-specific nucleic acid sequence. However, tumor cells may also be detected according to the invention by antibodies which recognize a specific epitope encoded by the splice variant. Said antibodies may be prepared by using for immunization peptides which are specific for said splice variant. Suitable for immunization are particularly the amino acids whose epitopes are distinctly different from the variant(s) of the genetic product, which is (are) preferably produced in healthy cells. Detection of the tumor cells with antibodies may be carried out here on a sample isolated from the patient or as imaging with intravenously administered antibodies. In addition to diagnostic usability, splice variants having new or altered epitopes are attractive targets for immunotherapy. The epitopes of the invention may be utilized for targeting therapeutically active monoclonal antibodies or T lymphocytes. In passive immunotherapy, antibodies or T lymphocytes which recognize splice variant-specific epitopes are adoptively transferred here. As in the case of other antigens, antibodies may be generated also by using standard technologies (immunization of animals, panning strategies for isolation of recombinant antibodies) with utilization of polypeptides which include these epitopes. Alternatively, it is possible to utilize for immunization nucleic acids coding for oligo- or polypeptides which contain said epitopes. Various techniques for in vitro or in vivo generation of epitope-specific T lymphocytes are known and have been described in detail, for example (Kessler J H, et al. 2001, Sahin et al., 1997) and are likewise based on utilizing oligo- or polypeptides which contain the splice variant-specific epitopes or nucleic acids coding for said oligo- or polypeptides. Oligo- or polypeptides which contain the splice variant-specific epitopes or nucleic acids coding for said polypeptides may also be used for utilization as pharmaceutically active substances in active immunotherapy (vaccination, vaccine therapy).

In one aspect, the invention relates to a pharmaceutical composition comprising an agent which recognizes the tumor-associated antigen identified according to the invention and which is preferably selective for cells which have expression or abnormal expression of a tumor-associated antigen identified according to the invention. In particular embodiments, said agent may cause induction of cell death, reduction in cell growth, damage to the cell membrane or secretion of cytokines and preferably have a tumor-inhibiting activity. In one embodiment, the agent is an antisense nucleic acid which hybridizes selectively with the nucleic acid coding for the tumor-associated antigen. In a further embodiment, the agent is an antibody which binds selectively to the tumor-associated antigen, in particular a complement-activated antibody which binds selectively to the tumor-associated antigen. In a further embodiment, the agent comprises two or more agents which each selectively recognize different tumor-associated antigens, at least one of which is a tumor-associated antigen identified according to the invention. Recognition needs not be accompanied directly with inhibition of activity or expression of the antigen. In this aspect of the invention, the antigen selectively limited to tumors preferably serves as a label for recruiting effector mechanisms to this specific location. In a preferred embodiment, the agent is a cytotoxic T lymphocyte which recognizes the antigen on an HLA molecule and lyses the cell labeled in this way. In a further embodiment, the agent is an antibody which binds selectively to the tumor-associated antigen and thus recruits natural or artificial effector mechanisms to said cell. In a further embodiment, the agent is a T helper lymphocyte which enhances effector functions of other cells specifically recognizing said antigen.

In one aspect, the invention relates to a pharmaceutical composition comprising an agent which inhibits expression or activity of a tumor-associated antigen identified according to the invention, In a preferred embodiment, the agent is an antisense nucleic acid which hybridizes selectively with the nucleic acid coding for the tumor-associated antigen. In a. further embodiment, the agent is an antibody which binds selectively to the tumor-associated antigen, In a further embodiment, the agent comprises two or more agents which each selectively inhibit expression or activity of different tumor-associated antigens, at least one of which is a tumor-associated antigen identified according to the invention.

The invention furthermore relates to a pharmaceutical composition which comprises an agent which, when administered, selectively increases the amount of complexes between an HLA molecule and a peptide epitope from the tumor-associated antigen identified according to the invention, In one embodiment, the agent comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule. In one embodiment, the agent comprises two or more agents which each selectively increase the amount of complexes between MHC molecules and peptide epitopes of different tumor-associated antigens, at least one of which is a tumor-associated antigen identified according to the invention.

The invention furthermore relates to a pharmaceutical composition which comprises one or more components selected from the group consisting of (i) a tumor-associated antigen identified according to the invention or a part thereof, (ii) a nucleic acid which codes for a tumor-associated antigen identified according to the invention or for a part thereof, (iii) an antibody which binds to a tumor-associated antigen identified according to the invention or to a part thereof, (iv) an antisense nucleic acid which hybridizes specifically with a nucleic acid coding for a tumor-associated antigen identified according to the invention, (v) a host cell which expresses a tumor-associated antigen identified according to the invention or a part thereof, and (vi) isolated complexes between a tumor-associated antigen identified according to the invention or a part thereof and an HLA molecule.

A nucleic acid coding for a tumor-associated antigen identified according to the invention or for a part thereof may be present in the pharmaceutical composition in an expression vector and functionally linked to a promoter.

A host cell present in a pharmaceutical composition of the invention may secrete the tumor-associated antigen or the part thereof, express it on the surface or may additionally express an HLA molecule which binds to said tumor-associated antigen or said part thereof. In one embodiment, the host cell expresses the HLA molecule endogenously. In a further embodiment, the host cell expresses the HLA molecule and/or the tumor-associated antigen or the part thereof in a recombinant manner. The host cell is preferably nonproliferative. In a preferred embodiment, the host cell is an antigen-presenting cell, in particular a dendritic cell, monocyte or a macrophage.

An antibody present in a pharmaceutical composition of the invention may be a monoclonal antibody. In further embodiments, the antibody is a chimeric or humanized antibody, a fragment of a natural antibody or a synthetic antibody, all of which may be produced by combinatory techniques. The antibody may be coupled to a therapeutically or diagnostically useful agent.

An antisense nucleic acid present in a pharmaceutical composition of the invention may comprise a sequence of 6-50, in particular 10-30, 15-30 and 20-30, contiguous nucleotides of the nucleic acid coding for the tumor-associated antigen identified according to the invention.

In further embodiments, a tumor-associated antigen, provided by a pharmaceutical composition of the invention either directly or via expression of a nucleic acid, or a part thereof binds to MHC molecules on the surface of cells, said binding preferably causing a cytolytic response and/or inducing cytokine release.

A pharmaceutical composition of the invention may comprise a pharmaceutically compatible carrier and/or an adjuvant. The adjuvant may be selected from saponin, GM-CSF, CpG nucleotides, RNA, a cytokine or a chemokine. A pharmaceutical composition of the invention is preferably used for the treatment of a disease characterized by selective expression or abnormal expression of a tumor-associated antigen. In a preferred embodiment, the disease is cancer.

The invention furthermore relates to methods of treating or diagnosing a disease characterized by expression or abnormal expression of one of more tumor-associated antigens. In one embodiment, the treatment comprises administering a pharmaceutical composition of the invention.

In one aspect, the invention relates to a method of diagnosing a disease characterized by expression or abnormal expression of a tumor-associated antigen identified according to the invention. The method comprises detection of (i) a nucleic acid which codes for the tumor-associated antigen or of a part thereof and/or (ii) detection of the tumor-associated antigen or of a part thereof, and/or (iii) detection of an antibody to the tumor-associated antigen or to a part thereof and/or (iv) detection of cytotoxic or T helper lymphocytes which are specific for the tumor-associated antigen or for a part thereof in a biological sample isolated from a patient. In particular embodiments, detection comprises (i) contacting the biological sample with an agent which binds specifically to the nucleic acid coding for the tumor-associated antigen or to the part thereof, to said tumor-associated antigen or said part thereof, to the antibody or to cytotoxic or T helper lymphocytes specific for the tumor-associated antigen or parts thereof, and (ii) detecting the formation of a complex between the agent and the nucleic acid or the part thereof, the tumor-associated antigen or the part thereof, the antibody or the cytotoxic or T helper lymphocytes. In one embodiment, the disease is characterized by expression or abnormal expression of two or more different tumor-associated antigens and detection comprises detection of two or more nucleic acids coding for said two or more different tumor-associated antigens or of parts thereof, detection of two or more different tumor-associated antigens or of parts thereof, detection of two or more antibodies binding to said two or more different tumor-associated antigens or to parts thereof or detection of two or more cytotoxic or T helper lymphocytes specific for said two or more different tumor-associated antigens. In a further embodiment, the biological sample isolated from the patient is compared to a comparable normal biological sample.

In a further aspect, the invention relates to a method for determining regression, course or onset of a disease characterized by expression or abnormal expression of a tumor-associated antigen identified according to the invention, which method comprises monitoring a sample from a patient who has said disease or is suspected of falling ill with said disease, with respect to one or more parameters selected from the group consisting of (i) the amount of nucleic acid which codes for the tumor-associated antigen or of a part thereof, (ii) the amount of the tumor-associated antigen or a part thereof, (iii) the amount of antibodies which bind to the tumor-associated antigen or to a part thereof, and (iv) the amount of cytolytic T cells or T helper cells which are specific for a complex between the tumor-associated antigen or a part thereof and an MHC molecule. The method preferably comprises determining the parameter(s) in a first sample at a first point in time and in a further sample at a second point in time and in which the course of the disease is determined by comparing the two samples. In particular embodiments, the disease is characterized by expression or abnormal expression of two or more different tumor-associated antigens and monitoring comprises monitoring (i) the amount of two or more nucleic acids which code for said two or more different tumor-associated antigens or of parts thereof, and/or (ii) the amount of said two or more different tumor-associated antigens or of parts thereof, and/or (iii) the amount of two or more antibodies which bind to said two or more different tumor-associated antigens or to parts thereof, and/or (iv) the amount of two or more cytolytic T cells or of T helper cells which are specific for complexes between said two or more different tumor-associated antigens or of parts thereof and MHC molecules.

According to the invention, detection of a nucleic acid or of a part thereof or monitoring the amount of a nucleic acid or of a part thereof may be carried out using a polynucleotide probe which hybridizes specifically to said nucleic acid or said part thereof or may be carried out by selective amplification of said nucleic acid or said part thereof. In one embodiment, the polynucleotide probe comprises a sequence of 6-50, in particular 10-30, 15-30 and 20-30, contiguous nucleotides of said nucleic acid.

In particular embodiments, the tumor-associated antigen to be detected or the part thereof is present intracellularly or on the cell surface. According to the invention, detection of a tumor-associated antigen or of a part thereof or monitoring the amount of a tumor-associated antigen or of a part thereof may be carried out using an antibody binding specifically to said tumor-associated antigen or said part thereof.

In further embodiments, the tumor-associated antigen to be detected or the part thereof is present in a complex with an MHC molecule, in particular an HLA molecule.

According to the invention, detection of an antibody or monitoring the amount of antibodies may be carried out using a protein or peptide binding specifically to said antibody.

According to the invention, detection of cytolytic T cells or of T helper cells or monitoring the amount of cytolytic T cells or of T helper cells which are specific for complexes between an antigen or a part thereof and MHC molecules may be carried out using a cell presenting the complex between said antigen or said part thereof and an MHC molecule.

The polynucleotide probe, the antibody, the protein or peptide or the cell, which is used for detection or monitoring, is preferably labeled in a detectable manner. In particular embodiments, the detectable marker is a radioactive marker or an enzymic marker. T lymphocytes may additionally be detected by detecting their proliferation, their cytokine production, and their cytotoxic activity triggered by specific stimulation with the complex of MHC and tumor-associated antigen or parts thereof. T lymphocytes may also be detected via a recombinant MHC molecule or else a complex of two or more MHC molecules which are loaded with the particular immunogenic fragment of one or more of the tumor-associated antigens and which can identify the specific T lymphocytes by contacting the specific T cell receptor.

In a further aspect, the invention relates to a method of treating, diagnosing or monitoring a disease characterized by expression or abnormal expression of a tumor-associated antigen identified according to the invention, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of a natural antibody.

The invention also relates to a method of treating a patient having a disease characterized by expression or abnormal expression of a tumor-associated antigen identified according to the invention, which method comprises (i) removing a sample containing immunoreactive cells from said patient, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. The invention likewise relates to cloning the T cell receptor of cytolytic T cells against the tumor-associated antigen. Said receptor may be transferred to other T cells which thus receive the desired specificity and, as under (iii), may be introduced into the patient.

In one embodiment, the host cell endogenously expresses an HLA molecule. In a further embodiment, the host cell recombinantly expresses an HLA molecule and/or the tumor-associated antigen or the part thereof. The host cell is preferably nonproliferative. In a preferred embodiment, the host cell is an antigen-presenting cell, in particular a dendritic cell, a monocyte or a macrophage.

In a further aspect, the invention relates to a method of treating a patient having a disease characterized by expression or abnormal expression of a tumor-associated antigen, which method comprises (i) identifying a nucleic acid which codes for a tumor-associated antigen identified according to the invention and which is expressed by cells associated with said disease, (ii) transfecting a host cell with said nucleic acid or a part thereof, (iii) culturing the transfected host cell for expression of said nucleic acid (this is not obligatory when a high rate of transfection is obtained), and (iv) introducing the host cells or an extract thereof into the patient in an amount suitable for increasing the immune response to the patient's cells associated with the disease. The method may further comprise identifying an MHC molecule presenting the tumor-associated antigen or a part thereof, with the host cell expressing the identified MHC molecule and presenting said tumor-associated antigen or a part thereof. The immune response may comprise a B cell response or a T cell response. Furthermore, a T cell response may comprise production of cytolytic T cells and/or T helper cells which are specific for the host cells presenting the tumor-associated antigen or a part thereof or specific for cells of the patient which express said tumor-associated antigen or a part thereof.

The invention also relates to a method of treating a disease characterized by expression or abnormal expression of a tumor-associated antigen identified according to the invention, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

Preferably, the host cells used according to the invention are nonproliferative or are rendered nonproliferative. A disease characterized by expression or abnormal expression of a tumor-associated antigen is in particular cancer.

The present invention furthermore relates to a nucleic acid selected from the group consisting of (a) a nucleic acid which comprises a nucleic acid sequence selected from the group consisting of SEQ ID NOs: 2-5, 20-21, 31-33, 39, 54-57, 62, 63, 85-88, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The invention furthermore relates to a nucleic acid, which codes for a protein or polypeptide comprising an amino acid sequence selected from the group consisting of SEQ ID NOs: 7-13, 14-18, 23-24, 34-36, 58-61, 64, 65, 89-100, a part or derivative thereof.

In a further aspect, the invention relates to promoter sequences of nucleic acids of the invention. These sequences may be functionally linked to another gene, preferably in an expression vector, and thus ensure selective expression of said gene in appropriate cells.

In a further aspect, the invention relates to a recombinant nucleic acid molecule, in particular DNA or RNA molecule, which comprises a nucleic acid of the invention.

The invention also relates to host cells which contain a nucleic acid of the invention or a recombinant nucleic acid molecule comprising a nucleic acid of the invention.

The host cell may also comprise a nucleic acid coding for a HLA molecule. In one embodiment, the host cell endogenously expresses the HLA molecule. In a further embodiment, the host cell recombinantly expresses the HLA molecule and/or the nucleic acid of the invention or a part thereof. Preferably, the host cell is nonproliferative. In a preferred embodiment, the host cell is an antigen-presenting cell, in particular a dendritic cell, a monocyte or a macrophage.

In a further embodiment, the invention relates to oligonucleotides which hybridize with a nucleic acid identified according to the invention and which may be used as genetic probes or as "antisense" molecules. Nucleic acid molecules in the form of oligonucleotide primers or competent samples, which hybridize with a nucleic acid identified according to the invention or parts thereof, may be used for finding nucleic acids which are homologous to said nucleic acid identified according to the invention. PCR amplification, Southern and Northern hybridization may be employed for finding homologous nucleic acids. Hybridization may be carried out under low stringency, more preferably under medium stringency and most preferably under high stringency conditions. The term "stringent conditions" according to the invention refers to conditions which allow specific hybridization between polynucleotides.

In a further aspect, the invention relates to a protein or polypeptide which is encoded by a nucleic acid selected from the group consisting of (a) a nucleic acid which comprises a nucleic acid sequence selected from the group consisting of SEQ ID NOs: 2-5, 20-21, 31-33, 39, 54-57, 62, 63, 85-88, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the invention relates to a protein or polypeptide which comprises an amino acid sequence selected from the group consisting of SEQ ID NOs: 7-13, 14-18, 23-24, 34-36, 58-61, 64, 65, 89-100, a part or derivative thereof In a further aspect, the invention relates to an immunogenic fragment of a tumor-associated antigen identified according to the invention. Said fragment preferably binds to a human HLA receptor or to a human antibody. A fragment of the invention preferably comprises a sequence of at least 6, in particular at least 8, at least 10, at least 12, at least 15, at least 20, at least 30 or at least 50, amino acids.

In a further aspect, the invention relates to an agent which binds to a tumor-associated antigen identified according to the invention or to a part thereof. In a preferred embodiment, the agent is an antibody. In further embodiments, the antibody is a chimeric, a humanized antibody or an antibody produced by combinatory techniques or is a fragment of an antibody. Furthermore, the invention relates to an antibody which binds selectively to a complex of (i) a tumor-associated antigen identified according to the invention or a part thereof and (ii) an MHC molecule to which said tumor-associated antigen identified according to the invention or said part thereof binds, with said antibody not binding to (i) or (ii) alone. An antibody of the invention may be a monoclonal antibody. In further embodiments, the antibody is a chimeric or humanized antibody or a fragment of a natural antibody.

The invention furthermore relates to a conjugate between an agent of the invention which binds to a tumor-associated antigen identified according to the invention or to a part thereof or an antibody of the invention and a therapeutic or diagnostic agent. In one embodiment, the therapeutic or diagnostic agent is a toxin.

In a further aspect, the invention relates to a kit for detecting expression or abnormal expression of a tumor-associated antigen identified according to the invention, which kit comprises agents for detection (i) of the nucleic acid which codes for the tumor-associated antigen or of a part thereof, (ii) of the tumor-associated antigen or of a part thereof, (iii) of antibodies which bind to the tumor-associated antigen or to a part thereof, and/or (iv) of T cells which are specific for a complex between the tumor-associated antigen or a part thereof and an MHC molecule. In one embodiment, the agents for detection of the nucleic acid or the part thereof are nucleic acid molecules for selective amplification of said nucleic acid, which comprise, in particular a sequence of 6-50, in particular 10-30, 15-30 and 20-30, contiguous nucleotides of said nucleic acid.

According to the invention, genes are described which are expressed in tumor cells selectively or aberrantly and which are tumor-associated antigens.

According to the invention, these genes or their derivatives are preferred target structures for therapeutic approaches. Conceptionally, said therapeutic approaches may aim at inhibiting the activity of the selectively expressed tumor-associated genetic product. This is useful, if said aberrant respective selective expression is functionally important in tumor pathogenicity and if its ligation is accompanied by selective damage of the corresponding cells. Other therapeutic concepts contemplate tumor-associated antigens as labels which recruit effector mechanisms having cell-damaging potential selectively to tumor cells. Here, the function of the target molecule itself and its role in tumor development are totally irrelevant.

"Derivative" of a nucleic acid means according to the invention that single or multiple nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or *Current Protocols in Molecular Biology*, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1× SDS at temperatures of up to 68° C.

According to the invention, complementary nucleic acids have at least 40%, in particular at least 50%, at least 60%, at least 70%, at least 80%, at least 90% and preferably at least 95%, at least 98 or at least 99%, identical nucleotides.

Nucleic acids coding for tumor-associated antigens may, according to the invention, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5' untranscribed and 5' untranslated sequences which are involved in initiation of transcription and translation, respectively, such as TATA box, capping sequence, CAAT sequence, and the like. More specifically, 5' untranscribed regulatory sequences comprise a promoter region which includes a promoter sequence for transcriptional control of the functionally linked gene. Regulatory sequences may also comprise enhancer sequences or upstream activator sequences.

Thus, on the one hand, the tumor-associated antigens illustrated herein may be combined with any expression control sequences and promoters. On the other hand, however, the promoters of the tumor-associated genetic products illustrated herein may, according to the invention, be combined with any other genes. This allows the selective activity of these promoters to be utilized.

According to the invention, a nucleic acid may furthermore be present in combination with another nucleic acid which codes for a polypeptide controlling secretion of the protein or polypeptide encoded by said nucleic acid from a host cell. According to the invention, a nucleic acid may also be present in combination with another nucleic acid which codes for a polypeptide causing the encoded protein or polypeptide to be anchored on the cell membrane of the host cell or compartmentalized into particular organelles of said cell.

In a preferred embodiment, a recombinant DNA molecule is according to the invention a vector, where appropriate with a promoter, which controls expression of a nucleic acid, for example a nucleic acid coding for a tumor-associated antigen of the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids or viral genomes.

The nucleic acids coding for a tumor-associated antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application. According to the invention, the term "host cell" relates to any cell which can be transformed or transfected with an exogenous nucleic acid. The term "host cells" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single cop or of two or more copies and, in one embodiment is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selective marker such as a gene imparting resistance to G418 (and thus enabling stably transfected cell lines to be selected) and the enhancer-promoter sequences of cytomegalovirus (CMV).

In those cases of the invention in which an HLA molecule presents a tumor-associated antigen or a part thereof, an expression vector may also comprise a nucleic acid sequence coding for said HLA molecule. The nucleic acid sequence coding for the HLA molecule may be present on the same expression vector as the nucleic acid coding for the tumor-associated antigen or the part thereof, or both nucleic acids may be present on different expression vectors. In the latter, case, the two expression vectors may be cotransfected into a cell. If a host cell expresses neither the tumor-associated antigen or the part thereof nor the HLA molecule, both nucleic acids coding therefor are transfected into the cell either on the same expression vector or on different expression vectors. If the cell already expresses the HLA molecule, only the nucleic acid sequence coding for the tumor-associated antigen or the part thereof can be transfected into the cell.

The invention also comprises kits for amplification of a nucleic acid coding for a tumor-associated antigen. Such kits comprise, for example, a pair of amplification primers which hybridize to the nucleic acid coding for the tumor-associated antigen. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid coding for the tumor-associated antigen, and the other primer will hybridize to the complementary strand in an arrangement which allows amplification of the nucleic acid coding for the tumor-associated antigen.

"Antisense" molecules or "antisense" nucleic acids may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, the "antisense molecule" also comprises a construct which contains a nucleic acid or a part thereof in reverse orientation with respect to its natural promoter. An antisense transcript of a nucleic acid or of a part thereof may form a duplex with the naturally occurring mRNA specifying the enzyme and thus prevent accumulation of or translation of the mRNA into the active enzyme. Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3' untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a "modified" oligonucleotide. Here, the oligonucleotide may be modified in very different ways, without impairing its ability to bind its target, in order to increase, for example, its stability or therapeutic efficacy. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, arboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

Preferably, the proteins and polypeptides described according to the invention have been isolated. The terms "isolated protein" or "isolated polypeptide" mean that the protein or polypeptide has been separated from its natural environment. An isolated protein or polypeptide may be in an essentially purified state. The term "essentially purified" means that the protein or polypeptide is essentially free of other substances with which it is associated in nature or in vivo.

Such proteins and polypeptides may be used, for example, in producing antibodies and in an immunological or diagnostic assay or as therapeutics. Proteins and polypeptides described according to the invention may be isolated from biological samples such as tissue or cell homogenates and may also be expressed recombinantly in a multiplicity of pro- or eukaryotic expression systems.

For the purposes of the present invention, "derivatives" of a protein or polypeptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible Amino acid deletion variants are characterized by the removal of one or more amino acids from the sequence Amino acid substitution variants are characterized by at least one residue in the sequence being removed and another residue being inserted in its place. Preference is given to the modifications being in positions in the amino acid sequence which are not conserved between homologous proteins or polypeptides. Preference is given to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val, (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. Techniques for introducing substitution mutations at predetermined sites into DNA which has a known or partially known sequence are well known and comprise M13 mutagenesis, for example. The manipulation of DNA sequences for preparing proteins having substitutions, insertions or deletions, is described in detail in Sambrook et al. (1989), for example.

According to the invention, "derivatives" of proteins or polypeptides also comprise single or multiple substitutions, deletions and/or additions of any molecules associated with the enzyme, such as carbohydrates, lipids and/or proteins or polypeptides. The term "derivative" also extends to all functional chemical equivalents of said proteins or polypeptides.

According to the invention, a part or fragment of a tumor-associated antigen has a functional property of the polypeptide from which it has been derived. Such functional properties comprise the interaction with antibodies, the interaction with other polypeptides or proteins, the selective binding of nucleic acids and an enzymatic activity. A particular property is the ability to form a complex with HLA and, where appropriate, generate an immune response. This immune response may be based on stimulating cytotoxic or T helper cells. A part or fragment of a tumor-associated antigen of the invention preferably comprises a sequence of at least 6, in particular at least 8, at least 10, at least 12, at least 15, at least 20, at least 30 or at least 50, consecutive amino acids of the tumor-associated antigen.

A part or a fragment of a nucleic acid coding for a tumor-associated antigen relates according to the invention to the part of the nucleic acid, which codes at least for the tumor-associated antigen and/or for a part or a fragment of said tumor-associated antigen, as defined above.

The isolation and identification of genes coding for tumor-associated antigens also make possible the diagnosis of a disease characterized by expression of one or more tumor-associated antigens. These methods comprise determining one or more nucleic acids which code for a tumor-associated antigen and/or determining the encoded tumor-associated antigens and/or peptides derived therefrom. The nucleic acids may be determined in the conventional manner, including by polymerase chain reaction or hybridization with a labeled probe. Tumor-associated antigens or peptides derived therefrom may be determined by screening patient antisera with respect to recognizing the antigen and/or the peptides. They may also be determined by screening T cells of the patient for specificities for the corresponding tumor-associated antigen.

The present invention also enables proteins binding to tumor-associated antigens described herein to be isolated, including antibodies and cellular binding partners of said tumor-associated antigens.

According to the invention, particular embodiments ought to involve providing "dominant negative" polypeptides derived from tumor-associated antigens. A dominant negative polypeptide is an inactive protein variant which, by way of interacting with the cellular machinery, displaces an active protein from its interaction with the cellular machinery or which competes with the active protein, thereby reducing the effect of said active protein. For example, a dominant negative receptor which binds to a ligand but does not generate any signal as response to binding to the ligand can reduce the biological effect of said ligand. Similarly, a dominant negative catalytically inactive kinase which usually interacts with target proteins but does not phosphorylate said target proteins may reduce phosphorylation of said target proteins as response to a cellular signal. Similarly, a dominant negative transcription factor which binds to a promoter site in the control region of a gene but does not increase transcription of said gene may reduce the effect of a normal transcription factor by occupying promoter binding sites, without increasing transcription.

The result of expression of a dominant negative polypeptide in a cell is a reduction in the function of active proteins. The skilled worker may prepare dominant negative variants of a protein, for example, by conventional mutagenesis methods and by evaluating the dominant negative effect of the variant polypeptide.

The invention also comprises substances such as polypeptides which bind to tumor-associated antigens. Such binding substances may be used, for example, in screening assays for detecting tumor-associated antigens and complexes of tumor-associated antigens with their binding partners and in a purification of said tumor-associated antigens and of complexes thereof with their binding partners. Such substances may also be used for inhibiting the activity of tumor-associated antigens, for example by binding to such antigens.

The invention therefore comprises binding substances such as, for example, antibodies or antibody fragments, which are capable of selectively binding to tumor associated antigens. Antibodies comprise polyclonal and monoclonal antibodies which are produced in the conventional manner.

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology*, $7^{th}$ Edition, Blackwell Scientific Publications, Oxford), The pFc' and Fc regions are, for example, effectors of the complement cascade but are not involved in antigen binding. An antibody from which the pFc' region has been enzymatically removed or which has been produced without the pFc' region, referred to as F(ab')$_2$ fragment, carries both antigen binding sites of a complete antibody. Similarly, an antibody from which the Fc region has been enzymatically removed or which has been produced without said Fc region, referred to Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

WO 92/04381 for example, describes production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

The invention also provides $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR. and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The invention also comprises "single-chain" antibodies.

The invention also comprises polypeptides which bind specifically to tumor-associated antigens. Polypeptide binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Phage display may be particularly effective in identifying binding peptides of the invention. In this connection, for example, a phage library is prepared (using, for example, the M13, fd or lambda phages) which presents inserts of from 4 to about 80 amino acid residues in length. Phages are then selected which carry inserts which bind to the tumor-associated antigen. This process may be repeated via two or more cycles of a reselection of phages binding to the tumor-associated antigen. Repeated rounds result in a concentration of phages carrying particular sequences. An analysis of DNA sequences may be carried out in order to identify the sequences of the expressed polypeptides. The smallest linear portion of the sequence binding to the tumor-associated antigen may be determined. The "two-hybrid system" of yeast may also be used for identifying polypeptides which bind to a tumor-associated antigen. Tumor-associated antigens described according to the invention or fragments thereof may be used for screening peptide libraries, including phage-display libraries, in order to identify and select peptide binding partners of the tumor-associated antigens. Such molecules may be used, for example, for screening assays, purification protocols, for interference with the function of the tumor-associated antigen and for other purposes known to the skilled worker.

The antibodies described above and other binding molecules may be used, for example, for identifying tissue which expresses a tumor-associated antigen. Antibodies may also be coupled to specific diagnostic substances for displaying cells and tissues expressing tumor-associated antigens. They may also be coupled to therapeutically useful substances. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium. According to the invention, the term "therapeutically useful substance" means any therapeutic molecule which, as desired, is selectively guided to a cell which expresses one or more tumor-associated antigens, including anticancer agents, radioactive iodine-labeled compounds, toxins, cytostatic or cytolytic drugs, etc. anticancer agents comprise, for example, aminoglutethimide, azathioprine, bleomycin sulfate, busulfan, carmustine, chlorambucil, cisplatin, cyclophosphamide, cyclpsporine, cytarabidine, dacarbazine, dactinomycin, daunorubin, doxorubicin, taxol, etoposide, fluorouracil, interferon-α, lomustine, mercaptopurine, methotrexate, mitotane, procarbazine HC1, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention, the term "disease" refers to any pathological state in which tumor-associated antigens are expressed or abnormally expressed. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, in particular seminomas, melanomas, teratomas, gliomas, colorectal cancer, breast cancer, prostate cancer, cancer of the uterus, ovarian cancer and lung cancer.

According to the invention, a biological sample may be a tissue sample and/or a cellular sample and may be obtained in the conventional manner such as by tissue biopsy, including punch biopsy, and by taking blood, bronchial aspirate, urine, feces or other body fluids, for use in the various methods described herein.

According to the invention, the term "immunoreactive cell" means a cell which can mature into an immune cell (such as B cell, T helper cell, or cytolytic T cell) with suitable stimulation Immunoreactive cells comprise OD34+ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for detecting specific clones of cytotoxic T lymphocytes (Altman et al., *Science* 274:94-96, 1996; Dunbar et al., *Curr. Biol.* 8:413-416, 1998). Soluble MHC class I molecules are folded in vitro in the presence of $\beta_2$ microglobulin and a peptide antigen binding to said class I molecule. The MHC/peptide complexes are purified and then labeled with biotin. Tetramers are formed by mixing the biotinylated peptide-MHC complexes with labeled avidin (e.g. phycoerythrin) in a molar ratio of 4:1. Tetramers are then contacted with cytotoxic T lymphocytes such as peripheral blood or lymph nodes. The tetramers bind to cytotoxic T lymphocytes which recognize the peptide antigen/MHC class I complex. Cells which are bound to the tetramers may be sorted by fluorescence-controlled cell sorting to isolate reactive cytotoxic T lymphocytes. The isolated cytotoxic T lymphocytes may then be propagated in vitro.

In a therapeutic method referred to as adoptive transfer (Greenberg, *J. Immunol.* 136(5):1917, 1986; Riddel et al., *Science* 257:238, 1992; Lynch et al., *Eur. J. Immunol.* 21:1403-1410, 1991; Kast et al., *Cell* 59:603-614, 1989), cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Often, of the T cell repertoire of a patient, only T cells with low affinity for a specific complex of this kind can be propagated, since those with high affinity have been extinguished due to development of tolerance. An alternative here may be a transfer of the T cell receptor itself. For this too, cells presenting the desired complex (e.g. dendritic cells) are combined with cytotoxic T lymphocytes of healthy individuals. This results in propagation of specific cytotoxic T lymphocytes with high affinity if the donor had no previous contact with the specific complex. The high affinity T cell receptor of these propagated specific T lymphocytes is cloned and can be transduced via gene transfer, for example using retroviral vectors, into T cells of other patients, as desired. Adoptive transfer is then carried out using these genetically altered T lymphocytes (Stanislawski et al., *Nat Immunol.* 2:962-70, 2001; Kessels et al., *Nat Immunol.* 2:957-61, 2001).

The therapeutic aspects above start out from the fact that at least some of the abnormal cells of the patient present a complex of a tumor-associated antigen and an HLA molecule. Such cells may be identified in a manner known per se. As soon as cells presenting the complex have been identified, they may be combined with a sample from the patient, which contains cytotoxic T lymphocytes. If the cytotoxic T lymphocytes lyse the cells presenting the complex, it can be assumed that a tumor-associated antigen is presented.

Adoptive transfer is not the only form of therapy which can be applied according to the invention. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting HLA molecule). Various cell types may be used. Furthermore, it is possible to use vectors which carry one or both of the genes of interest. Particular preference is given to viral or bacterial vectors. For example, nucleic acids coding for a tumor-associated antigen or for a part thereof may be functionally linked to promoter and enhancer sequences which control expression of said tumor-associated antigen or a fragment thereof in particular tissues or cell types. The nucleic acid may be incorporated into an expression vector. Expression vectors may be nonmodified extrachromosomal nucleic acids, plasmids or viral genomes into which exogenous nucleic acids may be inserted. Nucleic acids coding for a tumor-associated antigen may also be inserted into a retroviral genome, thereby enabling the nucleic acid to be integrated into the genome of the target tissue or target cell. In these systems, a microorganism such as vaccinia virus, pox virus, Herpes simplex virus, retrovirus or adenovirus carries the gene of interest and de facto "infects" host cells. Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen presenting cells in vivo possible. The tumor-associated antigen or a fragment thereof may be represented as protein, as DNA (e.g. within a vector) or as RNA. The tumor-associated antigen is processed to produce a peptide partner for the HLA molecule, while a fragment thereof may be presented without the need for further processing. The latter is the case in particular, if these can bind to HLA molecules. Preference is given to administration forms in which the complete antigen is processed in vivo by a dendritic cell, since this may also produce T helper cell responses which are needed for an effective immune response (Ossendorp at al., *Immunol Lett.* 74:75-9, 2000; Ossendorp et al., *J. Exp. Med.* 187:693-702, 1998). In general, it is possible to administer an effective amount of the tumor-associated antigen- to a patient by intradermal injection, for example. However, injection may also be carried out intranodally into a lymph node (Maloy at al., *Proc Natl Aced Sci USA* 98:3299-303, 2001). It may also be carried out in combination with reagents which facilitate uptake into dendritic cells. In vivo preferred tumor-associated antigens comprise those which react with allogenic cancer antisera or with T cells of many cancer patients. Of particular interest, however, are those against which no spontaneous immune responses pre-exist. Evidently, it is possible to induce against these immune responses which can lyse tumors (Keogh at al., *J. Immunol.* 167:787-96, 2001; Appella at al., *Biomed Pept Proteins Nucleic Acids* 1:177-84, 1995; Wentworth et al., *Mol Immunol.* 32:603-12, 1995).

The pharmaceutical compositions described according to the invention may also be used as vaccines for immunization. According to the invention, the terms "immunization" or "vaccination" mean an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization, one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and stimulating particular lymphocytes. Adjuvants are known and comprise in a nonlimiting way monophosphoryl lipid A (MPL, SmithKline Beecham), saponin such as QS21 (SmithKline Beecham), DQS21 (SmithKline Beecham; WO 96/33739), QS7, QS17, QS18 and QS-L1 (So et al., *Mol. Cells* 7:178-186, 1997), incomplete Freund's adjuvant, complete Freund's adjuvant, vitamin E, montanide, alum, CpG oligonucleotides (cf. Kreig at al., *Nature* 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 µg to about 100 µg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids. Examples of such costimulating molecules are B7-1 and B7-2 (CD80 and CD86, respectively) which are expressed on dendritic cells (DC) and interact with the CD28 molecule expressed on the T cells. This interaction provides a costimulation (signal 2) for an antigen/MHC/TCR-stimulated (signal 1) T cell, thereby enhancing propagation of said T cell and the effector function. B7 also interacts with CTLA4 (CD152) on T cells, and, studies involving CTLA4 and B7 ligands demonstrate that B7-CTLA4 interaction can enhance antitumor immunity and CTL propagation (Zheng, P. et al., *Proc. Natl. Acad. Sci. USA* 95(11):6284-6289 (1998)).

B7 is typically not expressed on tumor cells so that these are no effective antigen-presenting cells (APCs) for T cells. Induction of B7 expression would enable rumor cells to stimulate more effectively propagation of cytotoxic T lymphocytes and an effector function. Costimulation by a combination of B7/IL-6/IL-12 revealed induction of IFN-gamma and Th1-cytokine profile in a T cell population, resulting in further enhanced T cell activity (Gajewski et al., *J. Immunol.* 154:5637-5648 (1995)).

A complete activation of cytotoxic T lymphocytes and a complete effector function require an involvement of T helper cells via interaction between the CD40 ligand on said T helper cells and the CD40 molecule expressed by dendritic cells (Ridge et al., *Nature* 393:474 (1998), Bennett et al., *Nature* 393:478 (1998), Schönberger et al., *Nature* 393:480 (1998)). The mechanism of this costimulating signal probably relates to the increase in B7 production and associated IL-6/IL-12 production by said dendritic cells (antigen-presenting cells). CD40-CD40L interaction thus complements the interaction of signal I (antigen/MHC-TCR) and signal 2 (B7-CD28).

The use of anti-CD40 antibodies for stimulating dendritic cells would be expected to directly enhance a response to tumor antigens which are usually outside the range of an inflammatory response or which are presented by nonprofessional antigen-presenting cells (tumor cells). In these situations, T helper and B7-costimulating signals are not provided. This mechanism could be used in connection with therapies based on antigen-pulsed dendritic cells or in situations in which T helper epitopes have not been defined in known TRA precursors.

The invention also provides for administration of nucleic acids, polypeptides or peptides. Polypeptides and peptides may be administered in a manner known per se. In one embodiment, nucleic acids are administered by ex vivo methods, i.e, by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The invention also provides for administering nucleic acids in vivo by using vectors such as viruses and target-controlled liposomes.

In a preferred embodiment, a viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e, they are incapable of generating infectious particles).

Various methods may be used in order to introduce according to the invention nucleic acids into cells in vitro or in vivo. Methods of this kind comprise transfection of nucleic acid $CaPO_4$ precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants, CpG and cytokines and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lunch aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of particular condition characterized by expression of one or more tumor-associated antigens, the desired reaction relates to inhibition of the course of the disease. This comprises slowing down the progress of the disease and, in particular, interrupting the progress of the disease. The desired reaction in a treatment of a disease or of a condition may also be delay of the onset or a prevention of the onset of said disease or said condition.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the invention are preferably sterile and contain an effective amount of the therapeutically active substance to generate the desired reaction or the desired effect, The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 µg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may be used for preparing pharmaceutically compatible salts and are included in the invention. Pharmacologically and pharmaceutically compatible salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, suspensions, syrups, elixir or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples herein, which are used only for illustration purposes and are not meant to be limiting, Owing to the description and the examples, further embodiments which are likewise included in the invention are accessible to the skilled worker.

EXAMPLES

Material and Methods

The terms "in silico", "electronic" and "virtual cloning" refer solely to the utilization of methods based on databases, which may also be used to simulate laboratory experimental processes.

Unless expressly defined otherwise, all other terms and expressions are used so as to be understood by the skilled worker. The techniques and methods mentioned are carried out in a manner known per se and are described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information.

Datamining-Based Strategy for Determining eCT (Electronically Cloned Cancer/Testis Genes)

Two in silico strategies, namely GenBank keyword search and the cDNAxProfiler, were combined (FIG. 1). Utilizing the NCBI ENTREZ Search and Retrieval System (available at NCBI website), a GenBank search was carried out for candidate genes annotated as being specifically expressed in testicular tissue (Wheeler at al., *Nucleic Acids Research* 28:10-14, 2000).

Carrying out queries with the keywords "testis-specific gene", "sperm-specific gene", "spermatogonia-specific gene", candidate genes (GOI, genes of interest) were extracted from the databases. The search was restricted to part of the total information of these databases by using the limits "*homo sapiens*", for the organism, and "mRNA", for the type of molecule.

The list of the GOI found was curated by determining different names for the same sequence and eliminating such redundancies.

All candidate genes obtained by the keyword search were in turn studied with respect to their tissue distribution by the "electronic Northern" (eNorthern) method. The eNorthern is based on aligning the sequence of a GOI with an EST (expressed sequence tag) database (Adams et al., *Science* 252:1651, 1991) (BLAST search at NCBI website). The tissue origin of each EST which is found to be homologous to the GOI can be determined and in this way the sum of all ESTs produces a preliminary assessment of the tissue distribution of the GOI. Further studies were carried out only with those GOI which had no homologies to EST from nontesticular normal tissues with the exception of placenta and fetal tissue. This evaluation also took into account that the public domain contains wrongly annotated cDNA libraries (Scheurle et al., *Cancer Res*, 60:4037-4043, 2000).

The second datamining method utilized was the cDNA xProfiler of the NCBI Cancer Genome Anatomy Project (available at NCI website) (Hillier et al., *Genome Research* 6:807-828, 1996; Pennisi, *Science* 276:1023-1024, 1997). This allows pools of transcriptomes deposited in databases to be related to one another by logical operators. We have defined a pool A to which all expression libraries prepared from testis were assigned, excluding mixed libraries. All cDNA libraries prepared from normal tissues other than testis, ovary or fetal tissue were assigned to pool B. Generally, all cDNA libraries were utilized independently of underlying preparation methods, but only those with a size >1000 were admitted. Pool B was digitally subtracted from pool A by means of the BUT NOT operator. The set of GOI found in this manner was also subjected to eNorthern studies and validated by a literature research.

This combined datamining includes all of the about 13000 full-length genes in the public domain and predicts out of these genes a total of 140 genes having potential testis-specific expression, Among the latter were 25 previously known genes of the CT gene class, underlining the efficiency of our strategy.

All other genes were first evaluated in normal tissues by means of specific RT-PCR. All GOI which had proved to be expressed in nontesticular normal tissues had to be regarded as false-positives and were excluded from further studies. The remaining ones were studied in a large panel of a wide variety of tumor tissues. The antigens depicted below proved here to be ectopically activated in tumor cells.

RNA Extraction, Preparation of Poly-d(T) Primed cDNA and RT-PCR Analysis

Total RNA was extracted from native tissue material by using guanidium isothiocyanate as chaotropic agent (Chomczynski & Sacchi, *Anal. Biochem.* 162:156-9, 1987). After extraction with acidic phenol and precipitation with isopropanol, said RNA was dissolved in DEPC treated water.

First strand cDNA synthesis from 2-4 µg of total RNA was carried out in a 20 µl reaction mixture by means of Superscript II (Invitrogen), according to the manufacturer's information. The primer used was a dT(18) oligonucleotide. Integrity and quality of the cDNA were checked by amplification of p53 in a 30 cycle PCR (sense CGTGAGCGCTTCGAGATGTTCCG, (SEQ ID NO:52) antisense CCTAACCAGCTGCCCAACTGTAG, (SEQ ID NO:53) hybridization temperature 67° C.).

An archive of first strand cDNA was prepared from a number of normal tissues and tumor entities. For expression studies, 0.5 µl of these cDNAs was amplified in a 30 µl reaction mixture, using GOI-specific primers (see below) and 1 U of HotStarTaq DNA polymerase (Oiagen). Each reaction mixture contained 0.3 mM dNTPs, 0.3 µM of each primer and 3 µl of 10× reaction buffer. The primers were selected so as to be located in two different exons, and elimination of the interference by contaminating genomic DNA as the reason for false-positive results was confirmed by testing nonreverse-transcribed DNA as template. After 15 minutes at 95° C. to activate the HotStarTaq DNA polymerase, 35 cycles of PCR were carried out (1 min at 94° C., 1 min at the particular hybridization temperature, 2 min at 72° C. and final elongation at 72° C. for 6 min).

20 µl of this reaction were fractionated and analyzed on an ethidium bromide-stained agarose gel.

The following primers were used for expression analysis of the corresponding antigens at the hybridization temperature indicated.

```
LDH-C (67° C.)
                                    (SEQ ID NO: 25)
sense TGCCGTAGGCATGGCTTGTGC,
                                    (SEQ ID NO: 26)
antisense CAACATCTGAGACACCATTCC TPTE (64° C.)
                                    (SEQ ID NO: 27)
sense TGGATGTCACTCTCATCCTTG,
                                    (SEQ ID NO: 28)
antisense CCATAGTTCCTGTTCTATCTG TSBP (63° C.)
                                    (SEQ ID NO: 42)
sense TCTAGCACTGTCTCGATCAAG,
                                    (SEQ ID NO: 43)
antisense TGTCCTCTTGGTACATCTGAC
```

-continued

MS4A12 (66°)
                                       (SEQ ID NO: 44)
sense CTGTGTCAGCATCCAAGGAGC,
                                       (SEQ ID NO: 45)
antisense TTCACCTTTGCCAGCATGTAG BRCO1 (60'C)
                                       (SEQ ID NO: 46)
sense CTTGCTCTGAGTCATCAGATG,
                                       (SEQ ID NO: 47)
antisense CACAGAATATGAGCCATACAG TPX1 (65° C.)
                                       (SEQ ID NO: 78)
sense TTTTGTCTATGGTGTAGGACC,
                                       (SEQ ID NO: 79)
antisense GGAATGGCAATGATGTTACAG.

Preparation of Random Hexamer-Primed cDNA and Quantitative Real Time PCR

LDHC expression was quantified by means of real time PCR.

The principle of quantitative real time PCR using the ABI PRISM Sequence Detection System (PE Biosystems, USA) utilizes the 5'-3' exonuclease activity of Taq DNA polymerase for direct and specific detection of PCR products via release of fluorescence reporter dyes. In addition to sense and antisense primers, the PCR employs a doubly fluorescently labeled probe (TaqMan probe) which hybridizes to a sequence of the PCR product. The probe is labeled 5' with a reporter dye (e.g. FAM) and 3' with a quencher dye (e.g. TAMRA). If the probe is intact, the spatial proximity of reporter to quencher suppresses the emission of reporter fluorescence. If the probe hybridizes to the PCR product during the PCR, said probe is cleaved by the 5'-3' exonuclease activity of Taq DNA polymerase and suppression of the reporter fluorescence is removed. The increase in reporter fluorescence as a consequence of the amplification of the target, is measured after each PCR cycle and utilized for quantification. Expression of the target gene is quantified absolutely or relative to expression of a control gene with constant expression in the tissues to be studied. LDHC expression was calculated by means of the $\Delta\Delta$-$C_t$ method (PE Biosystems, USA), after normalizing the samples to 18s RNA as "housekeeping" gene. The reactions were carried out in duplex mixtures and determined in duplicate. cDNA was synthesized using the High Capacity cDNA Archive Kit (PE Biosystems, USA) and hexamer primers according to the manufacturer's information. In each case 5 µl of the diluted cDNA were used for the PCR in a total volume of 25 µl: sense primer (GGTGTCACTTCTGTGCCTTCCT) (SEQ ID NO:48) 300 nM; antisense primer (CGGCACCA-GTTCCAACAATAG) (SEQ ID NO:49) 300 nM; TaqMan probe (CAAAGGTTCTCCAAATGT) (SEQ ID NO:50) 250 nM; sense primer 18s RNA 50 nM; antisense primer 18s RNA 50 nM; 18s RNA sample 250 nM; 12.5 µl TaqMan Universal PCR Master Mix; initial denaturation 95° C. (10 min); 95° C. (15 sec); 60° C. (1 min); 40 cycles. Due to amplification of a 128 bp product beyond the border of exon 1 and exon 2, all LDHC splice variants described were included in the quantification.

Cloning and Sequence Analysis

Full length genes and gene fragments were cloned by common methods. The sequence was determined by amplifying corresponding antigens by means of the pfu proof-reading polymerase (Stratagene). After completion of the PCR, adenosine was ligated by means of HotStarTaq DNA polymerase to the ends of the amplicon in order to clone the fragments into the TOPO-TA vector according to the manufacturer's information. A commercial service carried out the sequencing. The sequences were analyzed by means of common prediction programs and algorithms.

Example 1

Identification of LDH C as a New Tumor Antigen

LDH C (SEQ ID NO:1) and its translation product (SEQ ID NO:6) have been described as testis-specific isoenzyme of the lactate dehydrogenase family. The sequence has been published in GenBank under accession number NM_017448. The enzyme forms a homotetramer having a molecular weight of 140 kDa (Goldberg, E. et al., *Contraception* 64(2):93-8, 2001; Cooker et al., *Biol. Reprod.* 48(6): 1309-19, 1993; Gupta, G. S., *Crit. Rev. Biochem, Mol. Biol.* 34(6):361-85, 1999).

RT-PCR studies for expression analysis using a primer pair (5'-TGCCGTAGGCATGGCTTGTGC-3', (SEQ ID NO:25) and 5'-CAACATCTGAGACACCATTCC-3') (SEQ ID NO:26) which does not cross-amplify the related and ubiquitously expressed isoenzymes LDH A and LDH B and which is based on the LDH C prototype sequence NM_017448 which has previously been described as being testis-specific, confirmed according to the invention the lack of expression in all normal tissues tested, but demonstrated that the stringent transcriptional repression of this antigen in somatic cells has been removed in the case of tumors; cf. Table 1. As has been described classically for CT genes, LDH C is expressed in a number of tumor entities.

TABLE 1

Expression of LDHC in tumors

| Tissue | Tested in total | Positive | % |
|---|---|---|---|
| Melanoma | 16 | 7 | 44 |
| Mammary carcinomas | 20 | 7 | 35 |
| Colorectal tumors | 20 | 3 | 15 |
| Prostate carcinomas | 8 | 3 | 38 |
| Bronchial carcinomas | 17 | 8 | 47 |
| Kidney cell carcinomas | 7 | 4 | 57 |
| Ovarian carcinomas | 7 | 3 | 43 |
| Thyroid carcinomas | 4 | 1 | 25 |
| Cervical carcinomas | 6 | 5 | 83 |
| Melanoma cell lines | 8 | 5 | 63 |
| Bronchial carcinoma cell lines | 6 | 2 | 33 |

The expected size of the amplification product is 824 bp, using the PCR primers mentioned above. According to the invention, however, amplification of multiple additional bands was observed in tumors, but not in testis. Since this is indicative for the presence of alternative splice variants, the complete open reading frame was amplified using LDH-C-specific primers (5'-TAGCGCCTCAACTGTCGTTGG-3', (SEQ ID NO:51) and 5'-CAACATCTGAGACACCATTCC-3') (SEQ ID NO:26) and independent full-length clones were sequenced. Alignments with the prototype ORF of the LDH C sequence described (SEQ ID NO:1) and the genomic sequence on chromosome 11 confirm additional splice variants (SEQ ID NO:2-5). The alternative splicing events result in the absence of exon 3 (SEQ ID NO:2), of the two exons 3 and 4 (SEQ ID NO:3), of the exons 3, 6 and 7 (SEQ ID NO:4) or of exon 7 (SEQ ID NO:5) (cf. FIG. 2).

These new splice variants are generated exclusively in tumors, but not in testis. Alternative splicing causes alterations in the reading frame and results in new possible ORFS encoding the amino acid sequences depicted in SEQ ID NO:7-13 (ORF for SEQ ID NO:7: nucleotide position 59-214 of SEQ ID NO:2 and, respectively, SEQ ID NO:4 ORF for SEQ ID NO:8: nucleotide position 289-939 of SEQ ID NO:2; ORF for SEQ ID NO:9: nucleotide position 59-196 of SEQ ID NO:3; ORF for SEQ ID NO:10: nucleotide position 535-765 of SEQ ID NO:3; ORF for SEQ ID NO:11: nucleotide position 289-618 of SEQ ID NO:4; ORF for SEQ ID NO:12: nucleotide position 497-697 of SEQ ID NO:4; ORF for SEQ ID NO:13: nucleotide position 59-784 of SEQ ID NO:5) (FIG. 2, 3). Apart from premature termination, utilization of alternative start codons is also possible so that the encoded proteins may be truncated both N-terminally and C-terminally.

While SEQ ID NO:8 and SEQ ID NO:10 represent truncated portions of the prototype protein, the protein sequence of SEQ ID NO:7, SEQ ID NO:9, SEQ ID NO:11, SEQ ID NO:12 and SEQ ID NO:13 are additionally altered and contain only tumor-specific epitopes (printed in bold type in FIG. 3). Peptide regions which could result in tumor specific epitopes are as follows (the strictly tumor-specific portion produced by frame shifts is underlined):

SEQ ID NO: 14: GAVGMACAISILLKITVYLQTPE (of SEQ ID NO: 7)

SEQ ID NO: 15: GAVGMACAISILLKWIF (of SEQ ID NO: 9)

SEQ ID NO: 16: GWIIGEHGDSSGIIWNKRRTLSQYPLCLGAEWC IRCCEN (of SEQ ID NO: 11)

SEQ 7D NO: 17: MVGLLENMVILVGLYGIKEELFL (of SEQ ID NO: 12)

SEQ ID NO: 18: EHWKNIHKQVIQRDYME (of SEQ ID NO: 13)

These regions may potentially contain epitopes which can be recognized on MHC I or MHC II molecules by T lymphocytes and which result in a strictly tumor-specific response.

Not all of the predicted proteins have the catalytic lactate dehydrogenase domain for NADH-dependent metabolization of pyruvate to lactate, which represents the last step of anaerobic glycolysis. This domain would be required for the enzymatic function as lactate dehydrogenase (framed in FIG. 3). Further analyses, for example using algorithms such as TMpred and pSORT (Nakai & Kanehisa, 1992), predict different subcellular localizations for the putative proteins.

According to the invention, the level of expression was quantified by real time PCR using a specific primer-sample set. The amplicon is present in the junction between exon 1 and exon 2 and thus detects all variants (SEQ ID NO:1-5). These studies too, do not detect any transcripts in normal tissues except testis. They confirm significant levels of expression in tumors (FIG. 4).

LDHC-specific polyclonal antibodies were produced according to the invention by selecting a peptide from the extreme N-terminal region MSTVKEQLIEKLIEDDENSQ (SEQ ID NO:80). LDHC-specific antibodies were produced in rabbits with the aid of this peptide. Subsequent studies on protein expression confirmed selective LDHC expression in testis and in various tumors. In addition, immunohistological studies in accordance with the invention revealed a distinct colocalization of LDHC with cytochrome C oxidase in mitochondria. This indicates that LDHC plays an important part in the respiratory chain of tumors.

Example 2

Identification of TPTE as a New Tumor Antigen

The sequences of the TPTE transcript (SEQ ID NO:19) and of its translation product (SEQ ID NO:22) have been published in GenBank under accession number NM_013315 (Walker, S. M. at al., *Biochem. J.* 360(Pt 2):277-83, 2001; Guipponi M. et al., *Hum. Genet.* 107(2):127-31, 2000; Chen H. et al., *Hum. Genet.* 105(5):399-409, 1999) TPTE has been described as a gene coding for a possible transmembrane tyrosinephosphatase, with testis-specific expression located in the pericentromeric region of chromosomes 21, 13, 15, 22 and Y (Chen, H. et al., *Hum. Genet.* 105:399-409, 1999). Alignment studies in accordance with the invention additionally reveal homologous genomic sequences on chromosomes 3 and 7.

According to the invention, PCR primers (5'-TGGATGT-CACTCTCATCCTTG-3' (SEQ ID NO:27) and 5'-CCATAGTTCCTGTTCTATCTG-3') (SEQ ID NO:28) were generated based on the sequence of TPTE (SEQ ID NO:19) and used for RT-PCR analyses (95° 15 min; 94° 1 min; 63° 1 min; 72° 1 min; 35 cycles) in a number of human tissues. Expression in normal tissues was shown to be limited to testis. As described for the other eCT, TPTE variants were shown according to the invention to be ectopically activated in a number of tumor tissues; cf. Table 2. According to the invention, further TPTE splice variants were identified (SEQ ID NO:20, SEQ ID NO:21, SEQ ID NO:54, SEQ ID NO:55, SEQ ID NO:56, SEQ ID NO:57) which are expressed in testicular tissue and in tumors and which have frame shifts and thus altered sequence regions (FIG. 5).

TABLE 2

Expression of TPTE in tumors

| Tissue | Tested in total | Positive | % |
| --- | --- | --- | --- |
| Melanoma | 18 | 9 | 50 |
| Mammary carcinomas | 20 | 4 | 20 |
| Colorectal tumors | 20 | 0 | 0 |
| Prostate carcinomas | 8 | 3 | 38 |
| Bronchial carcinomas | 23 | 9 | 39 |
| Kidney cell carcinomas | 7 | 0 | 0 |
| Ovarian carcinomas | 7 | 2 | 29 |
| Thyroid carcinomas | 4 | 0 | 0 |
| Cervical carcinomas | 6 | 1 | 17 |
| Melanoma cell lines | 8 | 4 | 50 |
| Bronchial carcinoma cell lines | 6 | 2 | 33 |
| Mammalian carcinoma cell lines | 5 | 4 | 80 |

The TPTE genomic sequence consists of 24 axons (accession number NT_029430). The transcript depicted in SEQ ID NO:19 contains all of these exons. The splice variant depicted in SEQ ID NO:20 is produced by splicing out exon 7. The splice variant depicted in SEQ ID NO:21 shows partial incorporation of an intron downstream of exon 15. As the variants SEQ ID NO:54, SEQ ID NO:55, SEQ ID NO:56, SEQ ID NO:57 indicate, it is alternatively also possible to splice out exons 18, 19, 20 and 21.

These alternative splicing events result in alterations of the encoded protein, with the reading frame being retained in principle (FIG. 6). For example, the translation product encoded by the sequence depicted in SEQ ID NO:20 (SEQ ID NO:23) has a deletion of 13 amino acids in comparison to the sequence depicted in SEQ ID NO:22. The translation product encoded by the sequence depicted in SEQ ID NO:21

(SEQ ID NO:24) carries an additional insertion in the central region of the molecule and thereby differs from the other variants by 14 amino acids.

The translation products of the variants SEQ ID NO:54, SEQ ID NO:55, SEQ ID NO:56, SEQ ID NO:57, namely the proteins SEQ ID NO:58, SEQ) ID NO:59, SEQ ID NO:60, SEQ ID NO:61, are likewise altered.

Analyses for predicting the functional domains reveal the presence of a tyrosinephosphatase domain for SEQ ID NO:22, SEQ ID NO:23, SEQ ID NO:24, SEQ ID NO:58, SEQ ID NO:60 but not for SEQ ID NO:59, SEQ ID NO:61. For all variants, 3-4 transmembrane domains are predicted (FIG. 6).

Analysis of TPTE antigen expression, using specific antibodies, confirmed selective expression in testis and in a number of different tumors. Colocalization studies moreover revealed that according to the invention TPTE is located together with class I immunoglobulins on the cell surface of tumor cells. Previously, TPTE had been described only as a Golgi-associated protein. Owing to TPTE expression on the cell surface of tumor cells, this tumor antigen is suitable according to the invention as an outstanding target for developing diagnostic and therapeutic monoclonal antibodies. Owing to the predicted membrane topology of TPTE, the extracellulary exposed regions are particularly suitable for this purpose according to the invention. According to the invention, this comprises the peptides FTDSKLYIPLEYRS (SEQ ID NO:81) and FDIKLLRNIPRWT (SEQ ID NO: 82). In addition, TPTE was shown to promote the migration of tumor cells. To this end, tumor cells which had been transfected with TPTE under the control of a eukaryotic promoter and control cells were studied in "Boyden chamber" migration experiments, as to whether they exhibit directed migration. TPTE-transfected cells here had according to the invention markedly (3-fold) increased migration in 4 independent experiments. These functional data indicate that TPTE plays an important part in the metastasizing of tumors. Thus, processes which inhibit according to the invention endogenous TPTE activity in tumor cells, for example by using antisense RNA, different methods of RNA interference (RNAi) by means of expression vectors or retroviruses, and by using small molecules, could result in reduced metastasizing and thus be very important therapeutically. A causal connection between the activity of a phosphatase in tumors and increased migration and increased formation of metastases was established recently for the PTEN tyrosinephosphastase (Iijima and Devreotes Cell 109: 599-610, 2002).

Example 3

Identification of TSBP as a New Tumor Antigen

The electronic cloning method employed according to the invention produced TSBP (SEQ ID NO:29) and the protein derived therefrom (SEQ ID NO:30). The gene has been described previously as being testis-specifically regulated (accession number NM_006781). The gene was predicted to encode a basic protein and to be located on chromosome 6 close to a sequence coding for an MHC complex (C6orf10) (Stammers M. et al., *Immunogenetics* 51(4-5):373-82, 2000). According to the invention, the previously described sequence was shown to be incorrect. The sequence of the invention is substantially different from the known sequence. According to the invention, 3 different splicing variants were cloned. The differences in the nucleotide sequences of the TSBP variants found according to the invention (SEQ ID NO:31, SEQ ID NO: 32, SEQ ID NO:33) to the known sequence (NM_006781, SEQ ID NO:29) are depicted in FIG. 7 (differences depicted in bold type). They result in frame shifts so that the proteins encoded by the TSBP variants found according to the invention (SEQ ID NO:34, SEQ ID NO:35, SEQ ID NO:36) differ substantially from the previously described protein (SEQ ID NO:30) (FIG. 8).

It was confirmed according to the invention that this antigen is strictly transcriptionally repressed in normal tissues (PCR primers 5'-TCTAGCACTGTCTCGATCAAG-3' (SEQ ID NO:42) and 5'-TGTCCTCTTGGTACATCTGAC-3') (SEQ ID NO:43). However, in 25 normal tissues studied, TSBP was expressed, apart from in testis, also in normal lymph node tissue. According to the invention, ectopic activation of TSBP in tumors was also detected, and it therefore qualifies as a tumor marker or tumor-associated antigen (Table 3).

Although TSBP, expression is found in primary tumor tissue, it is not found in permanent cell lines of corresponding tumor entities. Moreover, the gene is in the direct neighborhood of Notch 4 which is specifically expressed in arteries and involved in vascular morphogenesis. These are significant indications of this being a marker for specific endothelial cells. TSBP may therefore serve as a potential marker for tumor endothelia and for neovascular targeting.

Consequently, the TSBP promoter may be cloned to another genetic product whose selective expression in lymph nodes is desired.

Analysis of TSBP antigen expression, using specific antibodies, confirmed the selective localization of the protein in testis and lymph nodes and also in melanomas and bronchial carcinomas. In addition, immunohistological studies using GFP-tagged TSBP revealed a distinct perinucleic accumulation.

TABLE 3

Expression of TSBP in tumors

| Tissue | Tested in total | Positive | % |
| --- | --- | --- | --- |
| Melanoma | 12 | 2 | 16 |
| Mammary carcinomas | 15 | 0 | — |
| Colorectal tumors | 15 | 0 | — |
| Prostate carcinomas | 8 | 0 | — |
| Bronchial carcinomas | 7 | 17 | 41 |
| Kidney cell carcinomas | 7 | 0 | — |
| Ovarian carcinomas | 7 | 0 | — |
| Thyroid carcinomas | 4 | 0 | — |
| Cervical carcinomas | 6 | 0 | — |
| Melanoma cell lines | 8 | 0 | — |
| Bronchial carcinoma cell lines | 6 | 0 | — |

Example 4

Identification of MS4A12 as a New Tumor Antigen

MS4A12 (SEQ ID NO:37, accession number NM_017716) and its translation product (SEQ ID NO:38) have been described previously as members of a multigene family related to the B cell-specific antigen CD20, the hematopoietic cell-specific protein HTm4 and the β chain of the high affinity IgE receptor. All family members are characterized by at least four potential transmembrane domains and both the C and the N-terminus are cytoplasmic (Liang Y. et al., *Immunogenetics* 53(5):357-68, 2001; Liang Y. & Tedder, *Genomics* 72(2):119-27, 2001). According to the invention, RT-PCR studies on MS4A12 were carried out. The primers were selected based on the published MS4A12 sequence (NM_017716) (sense: CTGTGTCAGCATC-CAAGGAGC, (SEQ ID NO:44) antisense: TTCACCTTT-GCCAGCATGTAG) (SEQ ID NO:45). In the tissues tested, expression was detected only in testis, colon (6/8) and colorectal carcinomas (colon-Ca's) (16/20) and in colonic metastases (12/15) (FIG. 9).

The high incidence in colonic metastases makes TSBP an attractive diagnostic and therapeutic target. According to the invention, the predicted extracellular region comprising the protein sequence GVAGQDYWAVLSGKG (SEQ ID NO:83) is particularly suitable for producing monoclonal antibodies and small chemical inhibitors. According to the invention, the intracellular localization of the MS4A12 protein on the cell membrane was also confirmed by fluorescence superposition using plasma membrane markers in confocal immunofluorescence.

TABLE 4

Expression of MS4A12 in normal tissues and colorectal carcinomas and metastasis

| | |
|---|---|
| Ileum | + |
| Colon | + |
| Liver | − |
| Lung | − |
| Lymph nodes | − |
| Stomach | − |
| Spleen | − |
| Adrenal gland | − |
| Kidney | − |
| Esophagus | − |
| Ovary | − |
| Rectum | + |
| Testis | + |
| Thymus | − |
| Skin | − |
| Mamma | − |
| Pancreas | − |
| PBMC | − |
| PBMC act. | − |
| Prostate | − |
| Thyroid | − |
| Tube | − |
| Uterus | − |
| Cerebrum | − |
| Cerebellum | − |
| Colorectal tumors | 16/20 |
| Colorectal tumors metastases | 12/15 |

Thus, MS4A12 is a cell membrane-located differentiation antigen for normal colon epithelia, which is also expressed in colorectal tumors and metastases.

Example 5

Identification of BRCO1 as a New Tumor Antigen

BRCO1 and its translation product have not been described previously. The datamining method of the invention produced the EST (expressed sequence tag) AI668620. RT-PCR studies using specific primers (sense: CTTGCTCT-GAGTCATCAGATG, (SEQ ID NO:46) antisense: CACA-GAATATGAGCCATACAG) (SEQ ID NO:47) were carried for expression analysis. According to the invention, specific expression was found in testicular tissue and additionally in normal mammary gland (Table 5). In all other tissues, this antigen is transcriptionally repressed. It is likewise detected in mammary gland tumors (20 out of 20). BRCO1 is distinctly overexpressed in breast tumors in comparison with expression in normal mammary gland tissue (FIG. 10). Utilizing EST contigs (the following ESTs were incorporated: AW137203, BF327792, BF327797, BE069044, BF330665), more than 1500 bp of this transcript were cloned according to the invention by electronic full-length cloning (SEQ ID NO:39). The sequence maps to chromosome 10p11-12. In the same region, in immediate proximity, the gene for a mammary differentiation antigen, NY-BR-1, has been described previously (NM 052997; Jager, D. et al., *Cancer Res.* 61(5):2055-61, 2001).

TABLE 5

Expression of BRCO1 in normal tissues and breast tumors

| | |
|---|---|
| Ileum | − |
| Colon | − |
| Liver | − |
| Lung | − |
| Lymph nodes | − |
| Stomach | − |
| Spleen | − |
| Adrenal gland | − |
| Kidney | − |
| Esophagus | − |
| Ovary | − |
| Rectum | − |
| Testis | + |
| Thymus | − |
| Skin | − |
| Mamma | + |
| Pancreas | − |
| PBMC | − |
| PBMC act. | − |
| Prostate | − |
| Thyroid | − |
| Tube | − |
| Uterus | − |
| Cerebrum | − |
| Cerebellum | − |
| Mammary carcinomas | ++ (20/20) |

Matched pair (mammary carcinoma and adjacent normal tissue) studies revealed BRCO1 overexpression in 70% of the mammary carcinomas in comparison with the normal tissue.

Thus, BRCO1 is a new differentiation antigen for normal mammary gland epithelia, which is overexpressed in breast tumors.

Example 6

Identification of TPX1 as a New Tumor Antigen

The sequence of TPX1 (Acc. No. NM_003296; SEQ ID NO: 40) and of its translation product (SEQ ID NO:41, are known. The antigen has been described previously only as being testis-specific, that is as an element of the outer fibers and of the acrosome of sperms. Previously, an involvement as adhesion molecule in the attachment of sperms to Sertoli cells has been attributed to said antigen (O'Bryan, M. K. et al., *Mol. Reprod. Dev.* 58(1):116-25, 2001; Maeda, T, et al., *Dev. Growth Differ.* 41(6):715-22, 1999). The invention reveals, for the first time, aberrant expression of TPX1 in solid tumors (Table 6). Owing to the marked amino acid homology between TPX1 and the neutrophile-specific matrix glycoprotein SGP 28 (Kieldsen et al., *FEBS Lett* 380:246-259, 1996), TPX1-specific protein sequences comprising the peptide SREVTTNAQR (SEQ ID NO:84) are suitable according to the invention for preparing diagnostic and therapeutic molecules.

TABLE 6

Expression of TPX1 in tumors

| Tissue | Tested in total | Positive | % |
|---|---|---|---|
| Melanoma | 16 | 1 | 6 |
| Mammary carcinomas | 20 | 3 | 15 |
| Colorectal tumors | 20 | 0 | 0 |
| Prostate carcinomas | 8 | 3 | 37 |
| Bronchial carcinomas | 17 | 2 | 11 |
| Kidney cell carcinomas | 7 | 1 | 14 |
| Ovarian carcinomas | 7 | 1 | 14 |
| Thyroid carcinomas | 4 | 0 | 0 |
| Cervical carcinomas | 6 | 1 | 16 |
| Melanoma cell lines | 8 | 2 | 25 |
| Bronchial carcinoma cell lines | 6 | 1 | 16 |

Example 7

Identification of BRCO2 as a New Tumor Genetic Product

BROC2 and its translation product have not been described previously. The method of the invention produced the ESTs (expressed sequence tag) BE069341, BF330573 and AA601511. RT-PCR studies using specific primers (sense: AGACATGGCTCAGATGTGCAG, (SEQ ID NO:66) antisense: GGAAATTAGCAAGGCTCTCGC) (SEQ ID NO:67) were carried out for expression analysis. According to the invention, specific expression was found in testicular tissue and additionally in normal mammary gland (Table 7). In all other tissues, this genetic product is transcriptionally repressed. It is likewise detected in mammary gland tumors. Utilizing EST contigs (the following ESTs were incorporated: BF330573, AL044891 and AA601511), 1300 bp of this transcript were cloned according to the invention by electronic full-length cloning (SEQ ID 62), The sequence maps to chromosome 10p11-12. In the same region, in immediate proximity, the gene for a mammary differentiation genetic product, NY-BR-1, has been described previously (NM_052997; Jager, D. et al., Cancer Res. 61(5):2055-61, 2001), and here the BRCO1 described above under Example 6 is located. Further genetic analyses revealed according to the invention that the sequence listed under SEQ ID NO:62 represents the 3' untranslated region of the NY-BR-1 gene, which has not been described previously.

TABLE 7

Expression of BRCO2 in normal tissues and breast tumors

| Tissue | Expression |
|---|---|
| Testis | + |
| Mamma | + |
| Skin | − |
| Liver | − |
| Prostate | − |
| Thymus | − |
| Brain | − |
| Lung | − |
| Lymph nodes | − |
| Spleen | − |
| Adrenal gland | − |
| Ovary | − |
| Leukocytes | − |
| Colon | − |
| Esophagus | − |
| Uterus | − |
| Skeleton muscle | − |
| Epididymis | − |
| Bladder | − |
| Kidney | − |
| Mammary carcinoma | + |

BRCO2 is a new differentiation genetic product for normal mammary gland epithelia, which is also expressed in breast tumors.

Example 8

Identification of PCSC as a New Tumor Genetic Product

PCSC (SEQ ID NO:63) and its translation product have not been described previously. The datamining method of the invention produced the EST (expressed sequence tag) BF064073. RT-PCR studies using specific primers (sense: TCAGGTATTCCCTGCTCTTAC, (SEQ ID NO:68) antisense: TGGGCAATTCTCTCAGGCTTG) (SEQ ID NO:69) were carried out for expression analysis. According to the invention, specific expression was found in normal colon, and additionally in colon carcinomas (Table 5). In all other tissues, this genetic product is transcriptionally repressed. PCSC codes for two putative ORFs (SEQ ID 64 and SEQ ID 65) Sequence analysis of SEQ ID 64 revealed a structural homology to CXC cytokines. In addition, 4 alternative PCSC cDNA fragments were cloned (SEQ ID NO:85-88). In each case, according to the invention, each cDNA contains 3 putative ORFs which code for the polypeptides depicted in SEQ ID NO:89-100.

TABLE 8

Expression of PCSC in normal tissues and colorectal carcinomas

| Tissue | Expression |
|---|---|
| Ileum | + |
| Colon | + |
| Liver | − |
| Lung | − |
| Lymph nodes | − |
| Stomach | − |
| Spleen | − |
| Adrenal gland | − |
| Kidney | − |
| Esophagus | − |
| Ovary | − |
| Rectum | + |
| Testis | − |
| Thymus | − |
| Skin | − |
| Mamma | − |
| Pancreas | − |
| PBMC | − |
| PBMC act. | − |
| Prostate | − |
| Thyroid | − |
| Tube | − |
| Uterus | − |
| Cerebrum | − |
| Cerebellum | − |
| Colorectal tumors | 19/20 |
| Colorectal tumors metastases | 15/15 |

Thus, PCSC is a differentiation antigen for normal colon epithelia which is also expressed in colorectal tumors and in all colon metastases studied. PCSC expression detected in

Example 9

Identification of SGY-1 as a New Tumor Antigen

The sequences of the SGY-1 transcript (SEQ ID NO:70) and of its translation product (SEQ ID NO:71) have been published in GenBank under accession number AF177398 (Krupnik et al., *Gene* 238, 301-313, 1999). Soggy-1 has previously been described as a member of the Dickkopf protein family which act as inhibitors and antagonists of the Wnt family of proteins. The Wnt proteins in turn have important functions in embryonic development. Based on the sequence of SGY-1 (SEQ ID NO:70), PCR primers (5'-CTCCTATCCATGATGCTGACG-3' (SEQ ID NO:72) and 5'-CCTGAGGATGTACAGTAAGTG-3') (SEQ ID NO:73) were generated according to the invention and used for RT-PCR analyses (95° 15 min; 94° 1 min; 63° 1 min; 72° 1 min; 35 cycles) in a number of human tissues. Expression in normal tissues was shown to be limited to testis. As described for the other eCT, SGY-1 was shown according to the invention to be ectopically activated in a number of tumor tissues; cf. Table 9.

TABLE 9

Expression of SGY-1 in tumors

| Tissue | Tested in total | Positive | % |
|---|---|---|---|
| Melanoma | 16 | 4 | 25 |
| Mammary carcinomas | 20 | 4 | 20 |
| Colorectal tumors | 20 | 0 | 0 |
| Prostate carcinomas | 8 | 1 | 13 |
| Bronchial carcinomas | 32 | 3 | 18 |
| Kidney cell carcinomas | 7 | 0 | 0 |
| Ovarian carcinomas | 7 | 4 | 57 |
| Thyroid carcinomas | 4 | 0 | 0 |
| Cervical carcinomas | 6 | 2 | 33 |
| Melanoma cell lines | 8 | 2 | 25 |
| Bronchial carcinoma cell lines | 6 | 2 | 33 |
| Mammalian carcinoma cell lines | | | |

Example 10

Identification of MORC as a New Tumor Antigen

The sequences of the MORC transcript (SEQ ID NO:74) and of its translation product (SEQ ID NO:75) have been published in GenBank under the accession number XM_037008 (Inoue et al., *Hum Mol Genet*. July: 8(7):1201-7, 1999).

MORC has originally been described as being involved in spermatogenesis. Mutation of this protein in the mouse system results in underdevelopment of the gonads.

Based on the sequence of MORC (SEQ ID NO:74), PCR primers (5'-CTGAGTATCAGCTACCATCAG-3' (SEQ ID NO:76) and 5'-TCTGTAGTCCTTCACATATCG-3') (SEQ ID NO:77) were generated according to the invention and used for RT-PCR analyses (95° 15 min; 94° 1 min; 63° 1 min; 72° 1 min; 35 cycles) in a number of human tissues. Expression in normal tissues was shown to be limited to testis. As described for the other eCT, MORC was shown according to the invention to be ectopically activated in a number of tumor tissues cf. Table 10.

TABLE 10

Expression of MORC in tumors

| Tissue | Tested in total | Positive | % |
|---|---|---|---|
| Melanoma | 16 | 3 | 18 |
| Mammary carcinomas | 20 | 0 | 0 |
| Colorectal tumors | 20 | 0 | 0 |
| Prostate carcinomas | 8 | 0 | 0 |
| Bronchial carcinomas | 17 | 3 | 18 |
| Kidney cell carcinomas | 7 | 0 | 0 |
| Ovarian carcinomas | 7 | 1 | 14 |
| Thyroid carcinomas | 4 | 0 | 0 |
| Cervical carcinomas | 6 | 0 | 0 |
| Melanoma cell lines | 8 | 1 | 12 |
| Bronchial carcinoma cell lines | 6 | 1 | 17 |

---

The invention claimed is:

1. A method of diagnosing cancer, which method comprises detection of a nucleic acid which codes for a tumor-associated antigen in a biological sample isolated from a patient, with said tumor-associated antigen having a sequence encoded by a nucleic acid which comprises a nucleic acid sequence selected from the group consisting of SEQ ID NOs: 19-21, 54 and 56
    wherein the detection comprises
        (i) contacting the nucleic acids isolated from the biological sample with a primer set comprising SEQ ID NO: 27 and SEQ ID NO: 28 under conditions which amplifies the nucleic acids; wherein the conditions are suitable for RT-PCR comprising incubating the primer set and the nucleic acids at about 95° C. for about 15 minutes, incubating the primer set and the nucleic acids at about 94° C. for about 1 minute, hybridizing the primer set to the nucleic acids at about 63° C. for about 1 minute, and amplifying the nucleic acids at about 72° C. for about 1 minute, and repeating for about 35 cycles; and
        (ii) detecting the amplified nucleic acid;
    wherein an increased or abnormal amount of the nucleic acid in the biological sample as compared to a normal biological sample without cancer indicates the patient has cancer; and
    wherein the cancer is selected from the group consisting of seminomas, melanoma, teratomas, gliomas, colorectal cancer, breast cancer, prostate cancer, cancer of the uterus, ovarian cancer, lung cancer, kidney cancer, thyroid cancer, cervical cancer, and carcinomas.

2. The method of claim 1, wherein the tumor-associated antigen comprises an amino acid sequence selected from the group consisting of SEQ ID NOs: 22-24, 58 and 60.

3. A method for determining regression, course, or onset of cancer, which method comprises monitoring a sample from a patient who has cancer or is suspected of falling ill with cancer, with respect to the amount of nucleic acid which codes for the tumor-associated antigen, said tumor-associated antigen having a sequence encoded by a nucleic acid which comprises a nucleic acid sequence selected from the group consisting of SEQ ID NOs: 19-21, 54 and 56
    wherein the monitoring is determined in a first sample at a first point in time and in a second sample at a second point in time
    wherein the monitoring comprises
        (i) contacting the nucleic acid isolated from the sample with a primer set comprising SEQ ID NO: 27 and SEQ ID NO: 28 under conditions which amplifies the nucleic acids; wherein the conditions are suitable for RT-PCR comprising incubating the primer set and the nucleic acids at about 95° C. for about 15 minutes, incubating the primer set and the nucleic acids at about 94° C. for about 1 minute, hybridizing the primer set to the nucleic acids at about 63° C. for about 1 minute, and amplifying the nucleic acids at about 72° C. for about 1 minute, and repeating for about 35 cycles; and (ii) detecting the amplified nucleic acid;

wherein an increased or abnormal amount of the nucleic acid in the first sample as compared to the second sample indicates the regression, course, or onset of cancer; and wherein the cancer is selected from the group consisting of seminomas, melanoma, teratomas, gliomas, colorectal cancer, breast cancer, prostate cancer, cancer of the uterus, ovarian cancer, lung cancer, kidney cancer, thyroid cancer, cervical cancer, and carcinomas.

4. The method of claim 3, in which the tumor-associated antigen comprises an amino acid sequence selected from the group consisting of SEQ ID NOs: 22-24, 58 and 60.

5. A method of diagnosing cancer, which method comprises detection of a nucleic acid which codes for a tumor-associated antigen in a biological sample isolated from a patient, with said tumor-associated antigen having a sequence encoded by a nucleic acid which comprises a nucleic acid sequence selected from the group consisting of SEQ ID NOs: 19-21, 54 and 56;

wherein the detection comprises (i) contacting the nucleic acid isolated from the biological sample with a probe prepared by amplification with a primer set comprising SEQ ID NO: 27 and SEQ ID NO: 28 under conditions that allow the probe to hybridize to the nucleic acid;

(ii) detecting a complex formed between the probe and the nucleic acid from the sample;

wherein an increased or abnormal amount of the complex comprising the nucleic acid in the biological sample as compared to a normal biological sample indicates the patient has cancer; and wherein the cancer is selected from the group consisting of seminomas, melanoma, teratomas, gliomas, colorectal cancer, breast cancer, prostate cancer, cancer of the uterus, ovarian cancer, lung cancer, kidney cancer, thyroid cancer, cervical cancer, and carcinomas.

6. The method of claim 5, in which the tumor-associated antigen comprises an amino acid sequence selected from the group consisting of SEQ ID NOs: 22-24, 58 and 60.

7. A method for determining regression, course, or onset of cancer, which method comprises monitoring a sample from a patient who has cancer or is suspected of falling ill with cancer, with respect to the amount of nucleic acid which codes for the tumor-associated antigen, said tumor-associated antigen having a sequence encoded by a nucleic acid which comprises a nucleic acid sequence selected from the group consisting of SEQ ID NOs: 19-21, 54 and 56;

wherein the monitoring is determined in a first sample at a first point in time and in a second sample at a second point in time;

wherein the monitoring comprises (i) contacting the nucleic acid isolated from the sample with a probe prepared by amplification with a primer set comprising SEQ ID NO: 27 and SEQ ID NO: 28 under conditions that allow the probe to hybridize to the nucleic acid;

(ii) detecting a complex formed between the probe and the nucleic acid from the sample;

wherein an increased or abnormal amount of the complex comprising the nucleic acid in the first sample as compared to the second sample indicates the regression, course, or onset of cancer; and wherein the cancer is selected from the group consisting of seminomas, melanoma, teratomas, gliomas, colorectal cancer, breast cancer, prostate cancer, cancer of the uterus, ovarian cancer, lung cancer, kidney cancer, thyroid cancer, cervical cancer, and carcinomas.

8. The method of claim 7, in which the tumor-associated antigen comprises an amino acid sequence selected from the group consisting of SEQ ID NOs: 22-24, 58 and 60.

\* \* \* \* \*

SEQUENCE LISTING

<160> NUMBER OF SEQ ID NOS: 100

<210> SEQ ID NO 1
<211> LENGTH: 1171
<212> TYPE: DNA
<213> ORGANISM: Homo sapiens

<400> SEQUENCE: 1

```
ctgtcgttgg tgtatttttc tggtgtcact tctgtgcctt ccttcaaagg ttctccaaat      60
gtcaactgtc aaggagcagc taattgagaa gctaattgag gatgatgaaa actcccagtg     120
taaaattact attgttggaa ctggtgccgt aggcatggct tgtgctatta gtatcttact     180
gaaggatttg gctgatgaac ttgcccttgt tgatgttgca ttggacaaac tgaagggaga     240
aatgatggat cttcagcatg gcagtctttt ctttagtact tcaaagatta cttctggaaa     300
agattacagt gtatctgcaa actccagaat agttattgtc acagcaggtg caaggcagca     360
ggagggagaa actcgccttg ccctggtcca acgtaatgtg gctataatga aatcaatcat     420
```

```
tcctgccata gtccattata gtcctgattg taaaattctt gttgtttcaa atccagtgga      480
tattttgaca tatatagtct ggaagataag tggcttacct gtaactcgtg taattggaag      540
tggttgtaat ctagactctg cccgtttccg ttacctaatt ggagaaaagt tgggtgtcca      600
ccccacaagc tgccatggtt ggattattgg agaacatggt gattctagtg tgcccttatg      660
gagtggggtg aatgttgctg tgttgctct gaagactctg gaccctaaat taggaacgga       720
ttcagataag gaacactgga aaaatatcca taaacaagtt attcaaagtg cctatgaaat      780
tatcaagctg aagggtata cctcttgggc tattggactg tctgtgatgg atctggtagg       840
atccattttg aaaaatctta ggagagtgca cccagtttcc accatggtta agggattata      900
tggaataaaa aagaactct ttctcagtat cccttgtgtc ttgggcgga atggtgtctc        960 agatgttgtg aaaattaact tgaattctga ggaggaggcc cttttcaaga gagtgcaga     1020 aacactttgg aatattcaaa aggatctaat attttaaatt aaagccttct aatgttccac     1080
tgtttggaga acagaagata gcaggctgtg tattttaaat tttgaaagta ttttcattga     1140
tcttaaaaaa taaaaacaaa ttggagacct g                                    1171

<210> SEQ ID NO 2
<211> LENGTH: 1053
<212> TYPE: DNA
<213> ORGANISM: Homo sapiens

<400> SEQUENCE: 2
ctgtcgttgg tgtattttc tggtgtcact tctgtgcctt ccttcaaagg ttctccaaat        60
gtcaactgtc aaggagcagc taattgagaa gctaattgag gatgatgaaa actcccagtg      120
taaaattact attgttggaa ctggtgccgt aggcatggct tgtgctatta gtatcttact      180
gaagattaca gtgtatctgc aaactccaga atagttattg tcacagcagg tgcaaggcag      240
caggagggag aaactcgcct tgccctggtc aacgtaatg tggctataat gaaatcaatc       300
attcctgcca tagtccatta gtcctgat tgtaaaattc ttgttgtttc aaatccagtg        360
gatattttga catatatagt ctggaagata agtggcttac ctgtaactcg tgtaattgga      420
agtggttgta atctagactc tgcccgtttc cgttacctaa ttggagaaaa gttgggtgtc      480
caccccacaa gctgccatgg ttggattatt ggagaacatg gtgattctag tgtgccctta      540
tggagtgggg tgaatgttgc tgtgttgct ctgaagactc tggaccctaa attaggaacg       600
gattcagata aggaacactg gaaaaatatc cataaacaag ttattcaaag tgcctatgaa      660
attatcaagc tgaagggta tacctcttgg gctattggac tgtctgtgat ggatctggta       720
ggatccattt tgaaaaatct taggagagtg cacccagttt ccaccatggt taagggatta     780 tatgaataa aagaagaact ctttctcagt atcccttgtg tcttggggcg aatggtgtc        840 tcagatgttg tgaaaattaa cttgaattct gaggaggagg ccttttcaa gaagagtgca      900 gaaacactt ggaatattca aaaggatcta atattttaaa ttaaagcctt ctaatgttcc       960
actgtttgga gaacagaaga tagcaggctg tgtattttaa attttgaaag tattttcatt    1020
gatcttaaaa aataaaaaca aattggagac ctg                                   1053

<210> SEQ ID NO 3
<211> LENGTH: 879
<212> TYPE: DNA
<213> ORGANISM: Homo sapiens

<400> SEQUENCE: 3
```

```
ctgtcgttgg tgtattttc tggtgtcact tctgtgcctt ccttcaaagg ttctccaaat      60
gtcaactgtc aaggagcagc taattgagaa gctaattgag gatgatgaaa actcccagtg    120
taaaattact attgttggaa ctggtgccgt aggcatggct tgtgctatta gtatcttact    180
gaagtggata ttttgacata tatagtctgg aagataagtg gcttacctgt aactcgtgta    240
attggaagtg gttgtaatct agactctgcc cgtttccgtt acctaattgg agaaaagttg    300
ggtgtccacc ccacaagctg ccatggttgg attattggag aacatggtga ttctagtgtg    360
cccttatgga gtggggtgaa tgttgctggt gttgctctga agactctgga ccctaaatta    420
ggaacggatt cagataagga acactggaaa aatatccata acaagttat tcaaagtgcc     480
tatgaaatta tcaagctgaa ggggtatacc tcttgggcta ttggactgtc tgtgatggat    540
ctggtaggat ccattttgaa aaatcttagg agagtgcacc cagtttccac catggttaag    600
ggattatatg gaataaaaga agaactcttt ctcagtatcc cttgtgtctt ggggcggaat    660
ggtgtctcag atgttgtgaa aattaacttg aattctgagg aggaggccct ttcaagaag     720
agtgcagaaa cactttggaa tattcaaaag gatctaatat tttaaattaa gccttctaa     780
tgttccactg tttggagaac agaagatagc aggctgtgta ttttaaattt tgaaagtatt    840
ttcattgatc ttaaaaaata aaacaaatt ggagacctg                            879

<210> SEQ ID NO 4
<211> LENGTH: 811
<212> TYPE: DNA
<213> ORGANISM: Homo sapiens

<400> SEQUENCE: 4
ctgtcgttgg tgtattttc tggtgtcact tctgtgcctt ccttcaaagg ttctccaaat      60
gtcaactgtc aaggagcagc taattgagaa gctaattgag gatgatgaaa actcccagtg    120
taaaattact attgttggaa ctggtgccgt aggcatggct tgtgctatta gtatcttact    180
gaagattaca gtgtatctgc aaactccaga atagttattg tcacagcagg tgcaaggcag    240
caggagggag aaactcgcct tgccctggtc caacgtaatg tggctataat gaaatcaatc    300
attcctgcca tagtccatta tagtcctgat tgtaaaattc ttgttgtttc aaatccagtg    360
gatattttga catatatagt ctggaagata agtggcttac ctgtaactcg tgtaattgga    420
agtggttgta atctagactc tgcccgtttc cgttacctaa ttggagaaaa gttgggtgtc    480
caccccacaa gctgccatgg ttggattatt ggagaacatg gtgattctag tgggattata    540
tggaataaaa gaagaactct ttctcagtat cccttgtgtc ttggggcgga atggtgtctc    600
agatgttgtg aaaattaact tgaattctga ggaggaggcc ttttcaaga agagtgcaga    660
aacactttgg aatattcaaa aggatctaat attttaaatt aaagccttct aatgttccac    720
tgtttggaga acagaagata gcaggctgtg tattttaaat tttgaaagta ttttcattga    780
tcttaaaaaa taaaacaaa ttggagacct g                                    811

<210> SEQ ID NO 5
<211> LENGTH: 1047
<212> TYPE: DNA
<213> ORGANISM: Homo sapiens

<400> SEQUENCE: 5
ctgtcgttgg tgtattttc tggtgtcact tctgtgcctt ccttcaaagg ttctccaaat      60
gtcaactgtc aaggagcagc taattgagaa gctaattgag gatgatgaaa actcccagtg    120
taaaattact attgttggaa ctggtgccgt aggcatggct tgtgctatta gtatcttact    180
```

```
gaaggatttg gctgatgaac ttgcccttgt tgatgttgca ttggacaaac tgaagggaga      240
aatgatggat cttcagcatg gcagtctttt ctttagtact tcaaagatta cttctggaaa      300
agattacagt gtatctgcaa actccagaat agttattgtc acagcaggtg caaggcagca      360
ggagggagaa actcgccttg ccctggtcca acgtaatgtg gctataatga aatcaatcat      420
tcctgccata gtccattata gtcctgattg taaaattctt gttgtttcaa atccagtgga      480
tattttgaca tatatagtct ggaagataag tggcttacct gtaactcgtg taattggaag      540
tggttgtaat ctagactctg cccgtttccg ttacctaatt ggagaaaagt tgggtgtcca      600
ccccacaagc tgccatggtt ggattattgg agaacatggt gattctagtg tgcccttatg      660
gagtggggtg aatgttgctg gtgttgctct gaagactctg gaccctaaat taggaacgga      720
ttcagataag gaacactgga aaatatccca taaacaagtt attcaaaggg attatatgga      780
ataaaagaag aactctttct cagtatccct tgtgtcttgg ggcggaatgg tgtctcagat      840
gttgtgaaaa ttaacttgaa ttctgaggag gaggcccttt tcaagaagag tgcagaaaca      900
ctttggaata ttcaaaagga tctaatattt taaattaaag ccttctaatg ttccactgtt      960
tggagaacag aagatagcag gctgtgtatt ttaaattttg aaagtatttt cattgatctt     1020
aaaaaataaa aacaaattgg agacctg                                        1047

<210> SEQ ID NO 6
<211> LENGTH: 332
<212> TYPE: PRT
<213> ORGANISM: Homo sapiens

<400> SEQUENCE: 6

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
                20                  25                  30

Met Ala Cys Ala Ile Ser Ile Leu Leu Lys Asp Leu Ala Asp Glu Leu
            35                  40                  45

Ala Leu Val Asp Val Ala Leu Asp Lys Leu Lys Gly Glu Met Met Asp
        50                  55                  60

Leu Gln His Gly Ser Leu Phe Phe Ser Thr Ser Lys Ile Thr Ser Gly
65                  70                  75                  80

Lys Asp Tyr Ser Val Ser Ala Asn Ser Arg Ile Val Ile Val Thr Ala
                85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
    130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
                165                 170                 175

Lys Leu Gly Val His Pro Thr Ser Cys His Gly Trp Ile Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
```

```
             210                 215                 220
Glu His Trp Lys Asn Ile His Lys Gln Val Ile Gln Ser Ala Tyr Glu
225                 230                 235                 240

Ile Ile Lys Leu Lys Gly Tyr Thr Ser Trp Ala Ile Gly Leu Ser Val
                245                 250                 255

Met Asp Leu Val Gly Ser Ile Leu Lys Asn Leu Arg Arg Val His Pro
            260                 265                 270

Val Ser Thr Met Val Lys Gly Leu Tyr Gly Ile Lys Glu Glu Leu Phe
            275                 280                 285

Leu Ser Ile Pro Cys Val Leu Gly Arg Asn Gly Val Ser Asp Val Val
            290                 295                 300

Lys Ile Asn Leu Asn Ser Glu Glu Ala Leu Phe Lys Lys Ser Ala
305                 310                 315                 320

Glu Thr Leu Trp Asn Ile Gln Lys Asp Leu Ile Phe
                325                 330
```

<210> SEQ ID NO 7
<211> LENGTH: 51
<212> TYPE: PRT
<213> ORGANISM: Homo sapiens

<400> SEQUENCE: 7

```
Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
                20                  25                  30

Met Ala Cys Ala Ile Ser Ile Leu Leu Lys Ile Thr Val Tyr Leu Gln
            35                  40                  45

Thr Pro Glu
    50
```

<210> SEQ ID NO 8
<211> LENGTH: 216
<212> TYPE: PRT
<213> ORGANISM: Homo sapiens

<400> SEQUENCE: 8

```
Met Lys Ser Ile Ile Pro Ala Ile Val His Tyr Ser Pro Asp Cys Lys
1               5                   10                  15

Ile Leu Val Val Ser Asn Pro Val Asp Ile Leu Thr Tyr Ile Val Trp
                20                  25                  30

Lys Ile Ser Gly Leu Pro Val Thr Arg Val Ile Gly Ser Gly Cys Asn
            35                  40                  45

Leu Asp Ser Ala Arg Phe Arg Tyr Leu Ile Gly Glu Lys Leu Gly Val
        50                  55                  60

His Pro Thr Ser Cys His Gly Trp Ile Ile Gly Glu His Gly Asp Ser
65                  70                  75                  80

Ser Val Pro Leu Trp Ser Gly Val Asn Val Ala Gly Val Ala Leu Lys
                85                  90                  95

Thr Leu Asp Pro Lys Leu Gly Thr Asp Ser Asp Lys Glu His Trp Lys
            100                 105                 110

Asn Ile His Lys Gln Val Ile Gln Ser Ala Tyr Glu Ile Ile Lys Leu
        115                 120                 125

Lys Gly Tyr Thr Ser Trp Ala Ile Gly Leu Ser Val Met Asp Leu Val
    130                 135                 140

Gly Ser Ile Leu Lys Asn Leu Arg Arg Val His Pro Val Ser Thr Met
```

```
                    145                 150                 155                 160
Val Lys Gly Leu Tyr Gly Ile Lys Glu Glu Leu Phe Leu Ser Ile Pro
                165                 170                 175

Cys Val Leu Gly Arg Asn Gly Val Ser Asp Val Val Lys Ile Asn Leu
                180                 185                 190

Asn Ser Glu Glu Ala Leu Phe Lys Lys Ser Ala Glu Thr Leu Trp
                195                 200                 205

Asn Ile Gln Lys Asp Leu Ile Phe
    210                 215

<210> SEQ ID NO 9
<211> LENGTH: 45
<212> TYPE: PRT
<213> ORGANISM: Homo sapiens

<400> SEQUENCE: 9

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
                20                  25                  30

Met Ala Cys Ala Ile Ser Ile Leu Leu Lys Trp Ile Phe
                35                  40                  45

<210> SEQ ID NO 10
<211> LENGTH: 76
<212> TYPE: PRT
<213> ORGANISM: Homo sapiens

<400> SEQUENCE: 10

Met Asp Leu Val Gly Ser Ile Leu Lys Asn Leu Arg Arg Val His Pro
1               5                   10                  15

Val Ser Thr Met Val Lys Gly Leu Tyr Gly Ile Lys Glu Glu Leu Phe
                20                  25                  30

Leu Ser Ile Pro Cys Val Leu Gly Arg Asn Gly Val Ser Asp Val Val
                35                  40                  45

Lys Ile Asn Leu Asn Ser Glu Glu Ala Leu Phe Lys Lys Ser Ala
    50                  55                  60

Glu Thr Leu Trp Asn Ile Gln Lys Asp Leu Ile Phe
65                  70                  75

<210> SEQ ID NO 11
<211> LENGTH: 109
<212> TYPE: PRT
<213> ORGANISM: Homo sapiens

<400> SEQUENCE: 11

Met Lys Ser Ile Ile Pro Ala Ile Val His Tyr Ser Pro Asp Cys Lys
1               5                   10                  15

Ile Leu Val Val Ser Asn Pro Val Asp Ile Leu Thr Tyr Ile Val Trp
                20                  25                  30

Lys Ile Ser Gly Leu Pro Val Thr Arg Val Ile Gly Ser Gly Cys Asn
                35                  40                  45

Leu Asp Ser Ala Arg Phe Arg Tyr Leu Ile Gly Glu Lys Leu Gly Val
    50                  55                  60

His Pro Thr Ser Cys His Gly Trp Ile Ile Gly Glu His Gly Asp Ser
65                  70                  75                  80

Ser Gly Ile Ile Trp Asn Lys Arg Arg Thr Leu Ser Gln Tyr Pro Leu
                85                  90                  95
```

-continued

```
Cys Leu Gly Ala Glu Trp Cys Leu Arg Cys Cys Glu Asn
            100                 105

<210> SEQ ID NO 12
<211> LENGTH: 66
<212> TYPE: PRT
<213> ORGANISM: Homo sapiens

<400> SEQUENCE: 12

Met Val Gly Leu Leu Glu Asn Met Val Ile Leu Val Gly Leu Tyr Gly
1               5                   10                  15

Ile Lys Glu Glu Leu Phe Leu Ser Ile Pro Cys Val Leu Gly Arg Asn
            20                  25                  30

Gly Val Ser Asp Val Val Lys Ile Asn Leu Asn Ser Glu Glu Glu Ala
        35                  40                  45

Leu Phe Lys Lys Ser Ala Glu Thr Leu Trp Asn Ile Gln Lys Asp Leu
    50                  55                  60

Ile Phe
65

<210> SEQ ID NO 13
<211> LENGTH: 241
<212> TYPE: PRT
<213> ORGANISM: Homo sapiens

<400> SEQUENCE: 13

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Asp Leu Ala Asp Glu Leu
        35                  40                  45

Ala Leu Val Asp Val Ala Leu Asp Lys Leu Lys Gly Glu Met Met Asp
    50                  55                  60

Leu Gln His Gly Ser Leu Phe Phe Ser Thr Ser Lys Ile Thr Ser Gly
65              70                  75                  80

Lys Asp Tyr Ser Val Ser Ala Asn Ser Arg Ile Val Ile Val Thr Ala
            85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
    130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
            165                 170                 175

Lys Leu Gly Val His Pro Thr Ser Cys His Gly Trp Ile Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
    210                 215                 220

Glu His Trp Lys Asn Ile His Lys Gln Val Ile Gln Arg Asp Tyr Met
225                 230                 235                 240
```

Glu

<210> SEQ ID NO 14
<211> LENGTH: 23
<212> TYPE: PRT
<213> ORGANISM: Homo sapiens

<400> SEQUENCE: 14

Gly Ala Val Gly Met Ala Cys Ala Ile Ser Ile Leu Leu Lys Ile Thr
1               5                   10                  15

Val Tyr Leu Gln Thr Pro Glu
            20

<210> SEQ ID NO 15
<211> LENGTH: 17
<212> TYPE: PRT
<213> ORGANISM: Homo sapiens

<400> SEQUENCE: 15

Gly Ala Val Gly Met Ala Cys Ala Ile Ser Ile Leu Leu Lys Trp Ile
1               5                   10                  15

Phe

<210> SEQ ID NO 16
<211> LENGTH: 39
<212> TYPE: PRT
<213> ORGANISM: Homo sapiens

<400> SEQUENCE: 16

Gly Trp Ile Ile Gly Glu His Gly Asp Ser Ser Gly Ile Ile Trp Asn
1               5                   10                  15

Lys Arg Arg Thr Leu Ser Gln Tyr Pro Leu Cys Leu Gly Ala Glu Trp
            20                  25                  30

Cys Leu Arg Cys Cys Glu Asn
        35

<210> SEQ ID NO 17
<211> LENGTH: 23
<212> TYPE: PRT
<213> ORGANISM: Homo sapiens

<400> SEQUENCE: 17

Met Val Gly Leu Leu Glu Asn Met Val Ile Leu Val Gly Leu Tyr Gly
1               5                   10                  15

Ile Lys Glu Glu Leu Phe Leu
            20

<210> SEQ ID NO 18
<211> LENGTH: 17
<212> TYPE: PRT
<213> ORGANISM: Homo sapiens

<400> SEQUENCE: 18

Glu His Trp Lys Asn Ile His Lys Gln Val Ile Gln Arg Asp Tyr Met
1               5                   10                  15

Glu

<210> SEQ ID NO 19
<211> LENGTH: 2168
<212> TYPE: DNA
<213> ORGANISM: Homo sapiens

<400> SEQUENCE: 19

```
gaatccgcgg ggagggcaca acagctgcta cctgaacagt ttctgaccca acagttaccc      60
agcgccggac tcgctgcgcc ccggcggctc tagggacccc cggcgcctac acttagctcc     120
gcgcccgaga gaatgttgga ccgacgacac aagacctcag acttgtgtta ttctagcagc     180
tgaacacacc ccaggctctt ctgaccggca gtggctctgg aagcagtctg gtgtatagag     240
ttatggattc actaccagat tctactgtat gctcttgaca actatgacca caatggtcca     300
cccacaaatg aattatcagg agtgaaccca gaggcacgta tgaatgaaag tcctgatccg     360
actgacctgg cgggagtcat cattgagctc ggccccaatg acagtccaca gacaagtgaa     420
tttaaaggag caaccgagga ggcacctgcg aaagaaagcc cacacacaag tgaatttaaa     480
ggagcagccc gggtgtcacc tatcagtgaa agtgtgttag cacgactttc caagtttgaa     540
gttgaagatg ctgaaaatgt tgcttcatat gacagcaaga ttaagaaaat tgtgcattca     600
attgatcat cctttgcatt tggactattt ggagttttcc tggtcttact ggatgtcact     660
ctcatccttg ccgacctaat tttcactgac agcaaacttt atattccttt ggagtatcgt     720
tctatttctc tagctattgc cttatttttt ctcatggatg ttcttcttcg agtatttgta     780
gaaaggagac agcagtattt ttctgactta tttaacattt tagatactgc cattattgtg     840
attcttctgc tggttgatgt cgtttacatt ttttttgaca ttaagttgct taggaatatt     900
cccagatgga cacatttact tcgacttcta cgacttatta ttctgttaag aattttttcat    960
ctgtttcatc aaaaaagaca acttgaaaag ctgataagaa ggcgggtttc agaaaacaaa    1020
aggcgataca caagggatgg atttgaccta gacctcactt acgttacaga acgtattatt    1080
gctatgtcat ttccatcttc tggaaggcag tctttctata gaaatccaat caaggaagtt    1140
gtgcggtttc tagataagaa acaccgaaac cactatcgag tctacaatct atgcagtgaa    1200
agagcttacg atcctaagca cttccataat agggtcgtta gaatcatgat tgatgatcat    1260
aatgtcccca ctctacatca gatggtggtt ttcaccaagg aagtaaatga gtggatggct    1320
caagatcttg aaaacatcgt agcgattcac tgtaaaggag gcacagatag aacaggaact    1380
atggtttgtg ccttccttat tgcctctgaa atatgttcaa ctgcaaagga aagcctgtat    1440
tattttggag aaaggcgaac agataaaacc cacagcgaaa aatttcaggg agtagaaact    1500
ccttctcaga agagatatgt tgcatatttt gcacaagtga acatctctca aactggaat   1560
ctccctccaa gacggatact ctttataaaa cacttcatta tttattcgat tcctcgttat    1620
gtacgtgatc taaaaatcca aatagaaatg gagaaaaagg ttgtcttttc cactatttca    1680
ttaggaaaat gttcggtact tgataacatt acaacagaca aaatattaat tgatgtattc    1740
gacggtccac ctctgtatga tgatgtgaaa gtgcagtttt tctattcgaa tcttcctaca    1800
tactatgaca attgctcatt ttacttctgg ttgcacacat ctttattga aaataacagg    1860
ctttatctac caaaaatga attggataat ctacataaac aaaaagcacg gagaatttat    1920
ccatcagatt ttgccgtgga gatacttttt ggcgagaaaa tgacttccag tgatgttgta    1980
gctggatccg attaagtata gctcccccctt cccttctgg gaaagaatta tgttctttcc    2040
aaccctgcca catgttcata tatcctaaat ctatcctaaa tgttcccttg aagtatttat    2100
ttatgtttat atatgtttat acatgttctt caataaatct attacatata tataaaaaaa    2160
aaaaaaaa                                                              2168
```

<210> SEQ ID NO 20

<211> LENGTH: 2114
<212> TYPE: DNA
<213> ORGANISM: Homo sapiens

<400> SEQUENCE: 20

| | | | | | | |
|---|---|---|---|---|---|---|
| gaatccgcgg | ggagggcaca | acagctgcta | cctgaacagt | ttctgaccca | acagttaccc | 60 |
| agcgccggac | tcgctgcgcc | ccggcggctc | tagggacccc | cggcgcctac | acttagctcc | 120 |
| gcgcccgaga | gaatgttgga | ccgacgacac | aagacctcag | acttgtgtta | ttctagcagc | 180 |
| tgaacacacc | ccaggctctt | ctgaccggca | gtggctctgg | aagcagtctg | gtgtatagag | 240 |
| ttatggattc | actaccagat | tctactgtat | gctcttgaca | actatgacca | caatggtcca | 300 |
| cccacaaatg | aattatcagg | agtgaaccca | gaggcacgta | tgaatgaaag | tcctgatccg | 360 |
| actgacctgg | cgggagtcat | cattgagctc | ggccccaatg | acagtccaca | gacaagtgaa | 420 |
| tttaaggag | caaccgagga | ggcacctgcg | aaagaaagtg | tgttagcacg | actttccaag | 480 |
| tttgaagttg | aagatgctga | aaatgttgct | tcatatgaca | gcaagattaa | gaaaattgtg | 540 |
| cattcaattg | tatcatcctt | tgcatttgga | ctatttggag | ttttcctggt | cttactggat | 600 |
| gtcactctca | tccttgccga | cctaattttc | actgacagca | aactttatat | tcctttggag | 660 |
| tatcgttcta | tttctctagc | tattgcctta | ttttttctca | tggatgttct | tcttcgagta | 720 |
| tttgtagaaa | ggagacagca | gtattttct | gacttattta | acattttaga | tactgccatt | 780 |
| attgtgattc | ttctgctggt | tgatgtcgtt | tacattttt | ttgacattaa | gttgcttagg | 840 |
| aatattccca | gatggacaca | tttacttcga | cttctacgac | ttattattct | gttaagaatt | 900 |
| tttcatctgt | ttcatcaaaa | aagacaactt | gaaaagctga | taagaaggcg | ggtttcagaa | 960 |
| aacaaaaggc | gatacacaag | ggatggattt | gacctagacc | tcacttacgt | tacagaacgt | 1020 |
| attattgcta | tgtcatttcc | atcttctgga | aggcagtctt | tctatagaaa | tccaatcaag | 1080 |
| gaagttgtgc | ggtttctaga | taagaaacac | cgaaaccact | atcgagtcta | caatctatgc | 1140 |
| agtgaaagag | cttacgatcc | taagcacttc | cataataggg | tcgttagaat | catgattgat | 1200 |
| gatcataatg | tccccactct | acatcagatg | gtggttttca | ccaaggaagt | aaatgagtgg | 1260 |
| atggctcaag | atcttgaaaa | catcgtagcg | attcactgta | aaggaggcac | agatagaaca | 1320 |
| ggaactatgg | tttgtgcctt | ccttattgcc | tctgaaatat | gttcaactgc | aaaggaaagc | 1380 |
| ctgtattatt | ttggagaaag | gcgaacagat | aaaacccaca | gcgaaaaatt | tcagggagta | 1440 |
| gaaactcctt | ctcagaagag | atatgttgca | tattttgcac | aagtgaaaca | tctctacaac | 1500 |
| tggaatctcc | ctccaagacg | gatactcttt | ataaaacact | tcattattta | ttcgattcct | 1560 |
| cgttatgtac | gtgatctaaa | atccaaaata | gaaatggaga | aaaaggttgt | cttttccact | 1620 |
| atttcattag | gaaaatgttc | ggtacttgat | aacattacaa | cagacaaaat | attaattgat | 1680 |
| gtattcgacg | gtccacctct | gtatgatgat | gtgaaagtgc | agttttctcta | ttcgaatctt | 1740 |
| cctacatact | atgacaattg | ctcattttac | ttctggttgc | acacatcttt | tattgaaaat | 1800 |
| aacaggcttt | atctaccaaa | aaatgaattg | gataatctac | ataaacaaaa | agcacggaga | 1860 |
| atttatccat | cagattttgc | cgtggagata | cttttggcg | agaaaatgac | ttccagtgat | 1920 |
| gttgtagctg | gatccgatta | agtatagctc | ccccttcccc | ttctgggaaa | gaattatgtt | 1980 |
| ctttccaacc | ctgccacatg | ttcatatatc | ctaaatctat | cctaaatgtt | cccttgaagt | 2040 |
| atttatttat | gtttatatat | gtttatacat | gttcttcaat | aaatctatta | catatatata | 2100 |
| aaaaaaaaaa | aaaa | | | | | 2114 |

<210> SEQ ID NO 21
<211> LENGTH: 2222
<212> TYPE: DNA
<213> ORGANISM: Homo sapiens

<400> SEQUENCE: 21

| | | | | | |
|---|---|---|---|---|---|
| gaatccgcgg | ggagggcaca | acagctgcta | cctgaacagt | ttctgaccca | acagttaccc | 60 |
| agcgccggac | tcgctgcgcc | ccggcggctc | tagggacccc | cggcgcctac | acttagctcc | 120 |
| gcgcccgaga | gaatgttgga | ccgacgacac | aagacctcag | acttgtgtta | ttctagcagc | 180 |
| tgaacacacc | ccaggctctt | ctgaccggca | gtggctctgg | aagcagtctg | gtgtatagag | 240 |
| ttatggattc | actaccagat | tctactgtat | gctcttgaca | actatgacca | caatggtcca | 300 |
| cccacaaatg | aattatcagg | agtgaaccca | gaggcacgta | tgaatgaaag | tcctgatccg | 360 |
| actgacctgg | cgggagtcat | cattgagctc | ggccccaatg | cagtccaca | gacaagtgaa | 420 |
| tttaaaggag | caaccgagga | ggcacctgcg | aaagaaagcc | cacacacaag | tgaatttaaa | 480 |
| ggagcagccc | gggtgtcacc | tatcagtgaa | agtgtgttag | cacgactttc | caagtttgaa | 540 |
| gttgaagatg | ctgaaaatgt | tgcttcatat | gacagcaaga | ttaagaaaat | tgtgcattca | 600 |
| attgtatcat | cctttgcatt | tggactattt | ggagttttcc | tggtcttact | ggatgtcact | 660 |
| ctcatccttg | ccgacctaat | tttcactgac | agcaaacttt | atattccttt | ggagtatcgt | 720 |
| tctatttctc | tagctattgc | cttattttt | ctcatggatg | ttcttcttcg | agtatttgta | 780 |
| gaaaggagac | agcagtattt | ttctgactta | tttaacattt | tagatactgc | cattattgtg | 840 |
| attcttctgc | tggttgatgt | cgtttacatt | tttttttgaca | ttaagttgct | taggaatatt | 900 |
| cccagatgga | cacatttact | tcgacttcta | cgacttatta | ttctgttaag | aattttttcat | 960 |
| ctgtttcatc | aaaaaagaca | acttgaaaag | ctgataagaa | ggcgggtttc | agaaaacaaa | 1020 |
| aggcgataca | caagggatgg | atttgaccta | gacctcactt | acgttacaga | acgtattatt | 1080 |
| gctatgtcat | ttccatcttc | tggaaggcag | tctttctata | gaaatccaat | caaggaagtt | 1140 |
| gtgcggtttc | tagataagaa | acaccgaaac | cactatcgag | tctacaatct | atgcagtatg | 1200 |
| tacattactc | tatattgtgc | tactgtagat | agaaaacaga | ttactgcacg | tgaaagagct | 1260 |
| tacgatccta | agcacttcca | taatagggtc | gttagaatca | tgattgatga | tcataatgtc | 1320 |
| cccactctac | atcagatggt | ggttttcacc | aaggaagtaa | atgagtggat | ggctcaagat | 1380 |
| cttgaaaaca | tcgtagcgat | tcactgtaaa | ggaggcacag | atagaacagg | aactatggtt | 1440 |
| tgtgccttcc | ttattgcctc | tgaaatatgt | tcaactgcaa | aggaaagcct | gtattatttt | 1500 |
| ggagaaaggc | gaacagataa | aacccacagc | gaaaaatttc | agggagtaga | aactccttct | 1560 |
| cagaagagat | atgttgcata | ttttgcacaa | gtgaaacatc | tctacaactg | gaatctccct | 1620 |
| ccaagacgga | tactctttat | aaaacacttc | attatttatt | cgattcctcg | ttatgtacgt | 1680 |
| gatctaaaaa | tccaaataga | aatggagaaa | aaggttgtct | tttccactat | ttcattagga | 1740 |
| aaatgttcgg | tacttgataa | cattacaaca | gacaaaatat | taattgatgt | attcgacggt | 1800 |
| ccacctctgt | atgatgatgt | gaaagtgcag | tttttctatt | cgaatcttcc | tacatactat | 1860 |
| gacaattgct | catttactt | ctggttgcac | acatctttta | ttgaaaataa | caggctttat | 1920 |
| ctaccaaaaa | atgaattgga | taatctacat | aaacaaaaag | cacggagaat | ttatccatca | 1980 |
| gattttgccg | tggagatact | ttttggcgag | aaaatgactt | ccagtgatgt | tgtagctgga | 2040 |
| tccgattaag | tatagctccc | ccttccccctt | ctgggaaaga | attatgttct | ttccaacccct | 2100 |
| gccacatgtt | catatatcct | aaatctatcc | taaatgttcc | cttgaagtat | ttatttatgt | 2160 |

```
ttatatatgt ttatacatgt tcttcaataa atctattaca tatatataaa aaaaaaaaaa    2220
aa                                                                  2222

<210> SEQ ID NO 22
<211> LENGTH: 551
<212> TYPE: PRT
<213> ORGANISM: Homo sapiens

<400> SEQUENCE: 22

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Gly Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
            340                 345                 350

Leu Ile Ala Ser Glu Ile Cys Ser Thr Ala Lys Glu Ser Leu Tyr Tyr
```

```
                355                 360                 365
Phe Gly Glu Arg Arg Thr Asp Lys Thr His Ser Glu Lys Phe Gln Gly
370                 375                 380

Val Glu Thr Pro Ser Gln Lys Arg Tyr Val Ala Tyr Phe Ala Gln Val
385                 390                 395                 400

Lys His Leu Tyr Asn Trp Asn Leu Pro Pro Arg Arg Ile Leu Phe Ile
                405                 410                 415

Lys His Phe Ile Ile Tyr Ser Ile Pro Arg Tyr Val Arg Asp Leu Lys
                420                 425                 430

Ile Gln Ile Glu Met Glu Lys Lys Val Val Phe Ser Thr Ile Ser Leu
                435                 440                 445

Gly Lys Cys Ser Val Leu Asp Asn Ile Thr Thr Asp Lys Ile Leu Ile
                450                 455                 460

Asp Val Phe Asp Gly Pro Pro Leu Tyr Asp Val Lys Val Gln Phe
465                 470                 475                 480

Phe Tyr Ser Asn Leu Pro Thr Tyr Tyr Asp Asn Cys Ser Phe Tyr Phe
                485                 490                 495

Trp Leu His Thr Ser Phe Ile Glu Asn Asn Arg Leu Tyr Leu Pro Lys
                500                 505                 510

Asn Glu Leu Asp Asn Leu His Lys Gln Lys Ala Arg Arg Ile Tyr Pro
                515                 520                 525

Ser Asp Phe Ala Val Glu Ile Leu Phe Gly Lys Met Thr Ser Ser
                530                 535                 540

Asp Val Val Ala Gly Ser Asp
545                 550

<210> SEQ ID NO 23
<211> LENGTH: 533
<212> TYPE: PRT
<213> ORGANISM: Homo sapiens

<400> SEQUENCE: 23

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
                20                  25                  30

Glu Glu Ala Pro Ala Lys Glu Ser Val Leu Ala Arg Leu Ser Lys Phe
            35                  40                  45

Glu Val Glu Asp Ala Glu Asn Val Ala Ser Tyr Asp Ser Lys Ile Lys
        50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
                100                 105                 110

Leu Ala Ile Ala Leu Phe Phe Leu Met Asp Val Leu Leu Arg Val Phe
            115                 120                 125

Val Glu Arg Arg Gln Gln Tyr Phe Ser Asp Leu Phe Asn Ile Leu Asp
        130                 135                 140

Thr Ala Ile Ile Val Ile Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175
```

```
Arg Leu Leu Arg Leu Ile Ile Leu Leu Arg Ile Phe His Leu Phe His
            180                 185                 190

Gln Lys Arg Gln Leu Glu Lys Leu Ile Arg Arg Val Ser Glu Asn
        195                 200                 205

Lys Arg Arg Tyr Thr Arg Asp Gly Phe Asp Leu Asp Leu Thr Tyr Val
        210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
            340                 345                 350

Glu Arg Arg Thr Asp Lys Thr His Ser Glu Lys Phe Gln Gly Val Glu
        355                 360                 365

Thr Pro Ser Gln Lys Arg Tyr Val Ala Tyr Phe Ala Gln Val Lys His
    370                 375                 380

Leu Tyr Asn Trp Asn Leu Pro Pro Arg Arg Ile Leu Phe Ile Lys His
385                 390                 395                 400

Phe Ile Ile Tyr Ser Ile Pro Arg Tyr Val Arg Asp Leu Lys Ile Gln
                405                 410                 415

Ile Glu Met Glu Lys Lys Val Val Phe Ser Thr Ile Ser Leu Gly Lys
            420                 425                 430

Cys Ser Val Leu Asp Asn Ile Thr Thr Asp Lys Ile Leu Ile Asp Val
        435                 440                 445

Phe Asp Gly Pro Pro Leu Tyr Asp Asp Val Lys Val Gln Phe Phe Tyr
    450                 455                 460

Ser Asn Leu Pro Thr Tyr Tyr Asp Asn Cys Ser Phe Tyr Phe Trp Leu
465                 470                 475                 480

His Thr Ser Phe Ile Glu Asn Asn Arg Leu Tyr Leu Pro Lys Asn Glu
                485                 490                 495

Leu Asp Asn Leu His Lys Gln Lys Ala Arg Arg Ile Tyr Pro Ser Asp
            500                 505                 510

Phe Ala Val Glu Ile Leu Phe Gly Glu Lys Met Thr Ser Ser Asp Val
        515                 520                 525

Val Ala Gly Ser Asp
        530

<210> SEQ ID NO 24
<211> LENGTH: 569
<212> TYPE: PRT
<213> ORGANISM: Homo sapiens

<400> SEQUENCE: 24

Met Asn Glu Ser Pro Asp Pro Thr Asp Leu Ala Gly Val Ile Ile Glu
1               5                   10                  15
```

-continued

```
Leu Gly Pro Asn Asp Ser Pro Gln Thr Ser Glu Phe Lys Gly Ala Thr
             20                  25                  30
Glu Glu Ala Pro Ala Lys Glu Ser Pro His Thr Ser Glu Phe Lys Gly
         35                  40                  45
Ala Ala Arg Val Ser Pro Ile Ser Glu Ser Val Leu Ala Arg Leu Ser
    50                  55                  60
Lys Phe Glu Val Glu Asp Ala Glu Asn Val Ala Ser Tyr Asp Ser Lys
65                  70                  75                  80
Ile Lys Lys Ile Val His Ser Ile Val Ser Ser Phe Ala Phe Gly Leu
                85                  90                  95
Phe Gly Val Phe Leu Val Leu Leu Asp Val Thr Leu Ile Leu Ala Asp
            100                 105                 110
Leu Ile Phe Thr Asp Ser Lys Leu Tyr Ile Pro Leu Glu Tyr Arg Ser
        115                 120                 125
Ile Ser Leu Ala Ile Ala Leu Phe Phe Leu Met Asp Val Leu Leu Arg
    130                 135                 140
Val Phe Val Glu Arg Arg Gln Gln Tyr Phe Ser Asp Leu Phe Asn Ile
145                 150                 155                 160
Leu Asp Thr Ala Ile Ile Val Ile Leu Leu Val Asp Val Val Tyr
                165                 170                 175
Ile Phe Phe Asp Ile Lys Leu Leu Arg Asn Ile Pro Arg Trp Thr His
            180                 185                 190
Leu Leu Arg Leu Leu Arg Leu Ile Leu Leu Arg Ile Phe His Leu
        195                 200                 205
Phe His Gln Lys Arg Gln Leu Glu Lys Leu Ile Arg Arg Val Ser
    210                 215                 220
Glu Asn Lys Arg Arg Tyr Thr Arg Asp Gly Phe Asp Leu Asp Leu Thr
225                 230                 235                 240
Tyr Val Thr Glu Arg Ile Ile Ala Met Ser Phe Pro Ser Ser Gly Arg
                245                 250                 255
Gln Ser Phe Tyr Arg Asn Pro Ile Lys Glu Val Val Arg Phe Leu Asp
            260                 265                 270
Lys Lys His Arg Asn His Tyr Arg Val Tyr Asn Leu Cys Ser Met Tyr
        275                 280                 285
Ile Thr Leu Tyr Cys Ala Thr Val Asp Arg Lys Gln Ile Thr Ala Arg
    290                 295                 300
Glu Arg Ala Tyr Asp Pro Lys His Phe His Asn Arg Val Val Arg Ile
305                 310                 315                 320
Met Ile Asp Asp His Asn Val Pro Thr Leu His Gln Met Val Val Phe
                325                 330                 335
Thr Lys Glu Val Asn Glu Trp Met Ala Gln Asp Leu Glu Asn Ile Val
            340                 345                 350
Ala Ile His Cys Lys Gly Gly Thr Asp Arg Thr Gly Thr Met Val Cys
        355                 360                 365
Ala Phe Leu Ile Ala Ser Glu Ile Cys Ser Thr Ala Lys Glu Ser Leu
    370                 375                 380
Tyr Tyr Phe Gly Glu Arg Arg Thr Asp Lys Thr His Ser Glu Lys Phe
385                 390                 395                 400
Gln Gly Val Glu Thr Pro Ser Gln Lys Arg Tyr Val Ala Tyr Phe Ala
                405                 410                 415
Gln Val Lys His Leu Tyr Asn Trp Asn Leu Pro Pro Arg Ile Leu
            420                 425                 430
```

```
Phe Ile Lys His Phe Ile Ile Tyr Ser Ile Pro Arg Tyr Val Arg Asp
            435                 440                 445
Leu Lys Ile Gln Ile Glu Met Glu Lys Lys Val Val Phe Ser Thr Ile
        450                 455                 460
Ser Leu Gly Lys Cys Ser Val Leu Asp Asn Ile Thr Thr Asp Lys Ile
465                 470                 475                 480
Leu Ile Asp Val Phe Asp Gly Pro Pro Leu Tyr Asp Val Lys Val
                485                 490                 495
Gln Phe Phe Tyr Ser Asn Leu Pro Thr Tyr Tyr Asp Asn Cys Ser Phe
                500                 505                 510
Tyr Phe Trp Leu His Thr Ser Phe Ile Glu Asn Asn Arg Leu Tyr Leu
            515                 520                 525
Pro Lys Asn Glu Leu Asp Asn Leu His Lys Gln Lys Ala Arg Arg Ile
        530                 535                 540
Tyr Pro Ser Asp Phe Ala Val Glu Ile Leu Phe Gly Glu Lys Met Thr
545                 550                 555                 560
Ser Ser Asp Val Val Ala Gly Ser Asp
                565
```

<210> SEQ ID NO 25
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 25
tgccgtaggc atggcttgtg c                                        21

<210> SEQ ID NO 26
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 26
caacatctga gacaccattc c                                        21

<210> SEQ ID NO 27
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 27
tggatgtcac tctcatcctt g                                        21

<210> SEQ ID NO 28
<211> LENGTH: 21
<212> TYPE: DNA
<213> ORGANISM: Artificial Sequence
<220> FEATURE:
<223> OTHER INFORMATION: Description of artificial sequence:
      Oligonucleotide

<400> SEQUENCE: 28
ccatagttcc tgttctatct g                                        21

<210> SEQ ID NO 29
<211> LENGTH: 2192
<212> TYPE: DNA
<213> ORGANISM: Homo sapiens

<400> SEQUENCE: 29

```
agctcagctg ggagcgcaga ggctcacgcc tgtaatccca tcatttgctt aggtctgatc      60
aatctgctcc acacaatttc tcagtgatcc tctgcatctc tgcctacaag ggcctccctg     120
acacccaagt tcatattgct cagaaacagt gaacttgagt ttttcgtttt accttgatct     180
ctctctgaca aagaaatcca gatgatgcaa cacctgatga agacaataca tggaaaatga     240
cagtcttgga ataactttg gctgtcatcc tgactctact gggacttgcc atcctggcta      300
ttttgttaac aagatgggca cgacgtaagc aaagtgaaat gtatatctcc agatacagtt     360
cagaacaaag tgctagactt ctggactatg aggatggtag aggatcccga catgcatatc     420
aacacaaagt gacacttcat atgataaccg agagagatcc aaaaagagat tacacaccat     480
caaccaactc tctagcactg tctcgatcaa gtattgcttt acctcaagga tccatgagta     540
gtataaaatg tttacaaaca actgaagaac ctccttccag aactgcagga gccatgatgc     600
aattcacagc cctattcccg gagctacagg acctatcaag ctctctcaaa aaccattgt      660
gcaaactcca ggacctattg tacaatatct ggatccaatg tcagatcgca tctcacacaa     720
tcactggtca ccttcagcac ccgcggtcac ccatggcacc cataataatt tcacagagaa     780
ccgcaagtca gctggcagca cctataagaa tacctcaagt tcacactatg acagttctg      840
gaaaaatcac actgactcct gtggttatat taacaggtta catggacgaa gaacttcgaa     900
aaaaatcttg ttccaaaatc cagattctaa atgtggagg cactgcaagg tctcagatag      960
ccgagaagaa aacaaggaag caactaaaga atgacatcat atttacgaat tctgtagaat    1020
ccttgaaatc agcacacata aaggagccag aaagagaagg aaaaggcact gatttagaga    1080
aagacaaaat aggaatggag gtcaaggtag acagtgacgc tggaatacca aaaagacagg    1140
aaacccaact aaaaatcagt gaagatgagt ataccacaag gacagggagc ccaaataaag    1200
aaaagtgtgt cagatgtacc aagaggacag gagtccaagt aaagaagagt gagtcaggtg    1260
tcccaaaagg acaagaagcc caagtaacga agagtgggtt ggttgtactg aaaggacagg    1320
aagcccaggt agaagagagt gagatgggtg tgccaagaag acaggaatcc caagtaaaga    1380
agagtcagtc tggtgtctca aagggacagg aagcccaggt aaagaagagg gagtcagttg    1440
tactgaaagg acaggaagcc caggtagaga agagtgagtt gaaggtacca aaaggacaag    1500
aaggccaagt agagaagact gaggcagatg tgccaaagga acaagaggtc caagaaaaga    1560
agagtgaggc aggtgtactg aaaggaccag aatcccaagt aaagaacact gaggtgagtg    1620
taccagaaac actggaatcc caagtaaaga agagtgagtc aggtgtacta aaaggacagg    1680
aagcccaaga aaagaaggag agttttgagg ataaaggaaa taatgataaa gaaaaggaga    1740
gagatgcaga gaaagatcca aataaaaaag aaaaaggtga caaaacaca aaaggtgaca    1800
aaggaaagga caaagttaaa ggaagagag aatcagaaat caatggtgaa aaatcaaaag    1860
gctcgaaaag gcgaaggcaa atacaggaag gaagtacaac aaaaaagtgg aagagtaagg    1920
ataaattttt taaggcccca taagacaagt gattattatg attcccatac tccagataca    1980
aaccatatcc cagccattgc ctaaacagat tacaattata aaatcccttt catcttcata    2040
tcacagtttc tgctcttcag aagtttcacc ctttttaatc tctcagccac aaacctcagt    2100
tccaatattg ttataagtta agacgtatat gattccgtca agaaagactg gatactttct    2160
```
gaagtaaaac attttaatta aagaaaaaaa aa　　　　　　　　　　　　　　　　　　　　　2192

<210> SEQ ID NO 30
<211> LENGTH: 568
<212> TYPE: PRT
<213> ORGANISM: Homo sapiens

<400> SEQUENCE: 30

```
Met Thr Val Leu Glu Ile Thr Leu Ala Val Ile Leu Thr Leu Leu Gly
 1               5                   10                  15

Leu Ala Ile Leu Ala Ile Leu Leu Thr Arg Trp Ala Arg Arg Lys Gln
                20                  25                  30

Ser Glu Met Tyr Ile Ser Arg Tyr Ser Ser Glu Gln Ser Ala Arg Leu
            35                  40                  45

Leu Asp Tyr Glu Asp Gly Arg Gly Ser Arg His Ala Tyr Gln His Lys
        50                  55                  60

Val Thr Leu His Met Ile Thr Glu Arg Asp Pro Lys Arg Asp Tyr Thr
 65                  70                  75                  80

Pro Ser Thr Asn Ser Leu Ala Leu Ser Arg Ser Ser Ile Ala Leu Pro
                85                  90                  95

Gln Gly Ser Met Ser Ser Ile Lys Cys Leu Gln Thr Thr Glu Glu Pro
            100                 105                 110

Pro Ser Arg Thr Ala Gly Ala Met Met Gln Phe Thr Ala Leu Phe Pro
        115                 120                 125

Glu Leu Gln Asp Leu Ser Ser Ser Leu Lys Lys Pro Leu Cys Lys Leu
130                 135                 140

Gln Asp Leu Leu Tyr Asn Ile Trp Ile Gln Cys Gln Ile Ala Ser His
145                 150                 155                 160

Thr Ile Thr Gly His Leu Gln His Pro Arg Ser Pro Met Ala Pro Ile
                165                 170                 175

Ile Ile Ser Gln Arg Thr Ala Ser Gln Leu Ala Ala Pro Ile Arg Ile
            180                 185                 190

Pro Gln Val His Thr Met Asp Ser Ser Gly Lys Ile Thr Leu Thr Pro
        195                 200                 205

Val Val Ile Leu Thr Gly Tyr Met Asp Glu Glu Leu Arg Lys Lys Ser
210                 215                 220

Cys Ser Lys Ile Gln Ile Leu Lys Cys Gly Gly Thr Ala Arg Ser Gln
225                 230                 235                 240

Ile Ala Glu Lys Lys Thr Arg Lys Gln Leu Lys Asn Asp Ile Ile Phe
                245                 250                 255

Thr Asn Ser Val Glu Ser Leu Lys Ser Ala His Ile Lys Glu Pro Glu
            260                 265                 270

Arg Glu Gly Lys Gly Thr Asp Leu Glu Lys Asp Lys Ile Gly Met Glu
        275                 280                 285

Val Lys Val Asp Ser Asp Ala Gly Ile Pro Lys Arg Gln Glu Thr Gln
290                 295                 300

Leu Lys Ile Ser Glu Asp Glu Tyr Thr Thr Arg Thr Gly Ser Pro Asn
305                 310                 315                 320

Lys Glu Lys Cys Val Arg Cys Thr Lys Arg Thr Gly Val Gln Val Lys
                325                 330                 335

Lys Ser Glu Ser Gly Val Pro Lys Gly Gln Glu Ala Gln Val Thr Lys
            340                 345                 350

Ser Gly Leu Val Val Leu Lys Gly Gln Glu Ala Gln Val Glu Lys Ser
        355                 360                 365
```

```
Glu Met Gly Val Pro Arg Arg Gln Glu Ser Gln Val Lys Lys Ser Gln
            370                 375                 380

Ser Gly Val Ser Lys Gly Gln Glu Ala Gln Val Lys Lys Arg Glu Ser
385                 390                 395                 400

Val Val Leu Lys Gly Gln Glu Ala Gln Val Glu Lys Ser Glu Leu Lys
                405                 410                 415

Val Pro Lys Gly Gln Glu Gly Gln Val Glu Lys Thr Glu Ala Asp Val
                420                 425                 430

Pro Lys Glu Gln Glu Val Gln Glu Lys Lys Ser Glu Ala Gly Val Leu
            435                 440                 445

Lys Gly Pro Glu Ser Gln Val Lys Asn Thr Glu Val Ser Val Pro Glu
            450                 455                 460

Thr Leu Glu Ser Gln Val Lys Lys Ser Glu Ser Gly Val Leu Lys Gly
465                 470                 475                 480

Gln Glu Ala Gln Glu Lys Lys Glu Ser Phe Glu Asp Lys Gly Asn Asn
                485                 490                 495

Asp Lys Glu Lys Glu Arg Asp Ala Glu Lys Asp Pro Asn Lys Lys Glu
            500                 505                 510

Lys Gly Asp Lys Asn Thr Lys Gly Asp Lys Gly Lys Asp Lys Val Lys
            515                 520                 525

Gly Lys Arg Glu Ser Glu Ile Asn Gly Glu Lys Ser Lys Gly Ser Lys
530                 535                 540

Arg Arg Arg Gln Ile Gln Glu Gly Ser Thr Thr Lys Lys Trp Lys Ser
545                 550                 555                 560

Lys Asp Lys Phe Phe Lys Gly Pro
                565

<210> SEQ ID NO 31
<211> LENGTH: 1686
<212> TYPE: DNA
<213> ORGANISM: Homo sapiens

<400> SEQUENCE: 31
atgacagtct tggaaataac tttggctgtc atcctgactc tactgggact tgccatcctg      60 gctatttttgt taacaagatg ggcacgatgt aagcaaagtg aaatgtatat ctccagatac     120
agttcagaac aaagtgctag acttctggac tatgaggatg gtagaggatc ccgacatgca     180
tattcaacac aaagtgacac ttcatatgat aaccgagaga gatccaaaag agattacaca     240
ccatcaacca actctctagc actgtctcga tcaagtattg ctttacctca aggatccatg     300
agtagtataa atgtttaca acaactgaa gaacctcctt ccagaactgc aggagccatg     360
atgcaattca gcccctat tcccggagct acaggaccta tcaagctctc tcaaaaaacc     420
attgtgcaaa ctccaggacc tattgtacaa tatcctggat ccaatgctgg tccaccttca     480 gcacccgcg gtccacccat ggcacccata taatttcac agagaaccgc aagtcagctg      540
gcagcaccta taataatttc gcagagaact gcaagaatac ctcaagttca cactatggac     600
agttctggaa aaatcacact gactcctgtg ttatattaa caggttacat ggatgaagaa     660
cttgcaaaaa atcttgttc caaaatccag attctaaaat gtggaggcac tgcaaggtct     720
cagaatagcc gagaagaaaa caaggaagca ctaaagaatg acatcatatt tacgaattct     780
gtagaatcct tgaaatcagc acacataaag gagccagaaa gagaaggaaa aggcactgat     840
ttagagaaag acaaaatagg aatggaggtc aaggtagaca gtgacgctgg aataccaaaa     900
agacaggaaa cccaactaaa aatcagtgag atgagtatac cacaaggaca gggagcccaa     960
```

| | |
|---|---|
| ataaagaaaa gtgtgtcaga tgtaccaaga ggacaggagt cccaagtaaa gaagagtgag | 1020 |
| tcaggtgtcc caaaaggaca agaagcccaa gtaacgaaga gtgggttggt tgtactgaaa | 1080 |
| ggacaggaag cccaggtaga gaagagtgag atgggtgtgc caagaagaca ggaatcccaa | 1140 |
| gtaaagaaga gtcagtctgg tgtctcaaag ggacaggaag cccaggtaaa gaagagggag | 1200 |
| tcagttgtac tgaaaggaca ggaagcccag gtagagaaga gtgagttgaa ggtaccaaaa | 1260 |
| ggacaagaag gccaagtaga gaagactgag gcagatgtgc caaggaaaca agaggtccaa | 1320 |
| gaaaagaaga gtgaggcagg tgtactgaaa ggaccagaat cccaagtaaa gaacactgag | 1380 |
| gtgagtgtac cagaaacact ggaatcccaa gtaaagaaga gtgagtcagg tgtactaaaa | 1440 |
| ggacaggaag cccaagaaaa gaaggagagt tttgaggata aaggaaataa tgataaagaa | 1500 |
| aaggagagag atgcagagaa agatccaaat aaaaaagaaa aaggtgacaa aaacacaaaa | 1560 |
| ggtgacaaag gaaaggacaa agttaaagga agagagaat cagaaatcaa tggtgaaaaa | 1620 |
| tcaaaaggct cgaaaagggc gaaggcaaat acaggaagga agtacaacaa aaaagtggaa | 1680 |
| gagtaa | 1686 |

<210> SEQ ID NO 32
<211> LENGTH: 1710
<212> TYPE: DNA
<213> ORGANISM: Homo sapiens

<400> SEQUENCE: 32

| | |
|---|---|
| atgacagtct tggaaataac tttggctgtc atcctgactc tactgggact tgccatcctg | 60 |
| gctattttgt taacaagatg ggcacgacgt aagcaaagtg aaatgcatat ctccagatac | 120 |
| agttcagaac aaagtgctag acttctggac tatgaggatg gtagaggatc ccgacatgca | 180 |
| tattcaacac aaagtgacac ttcatgtgat aaccgagaga gatccaaaag agattacaca | 240 |
| ccatcaacca actctctagc actgtctcga tcaagtattg ctttacctca aggatccatg | 300 |
| agtagtataa aatgtttaca aacaactgaa gaacttcctt ccagaactgc aggagccatg | 360 |
| atgcaattca cagcccctat tcccggagct acaggaccta tcaagctctc tcaaaaaacc | 420 |
| attgtgcaaa ctccaggacc tattgtacaa tatcctggac ccaatgtcag atcgcatcct | 480 |
| cacacaatca ctggtccacc ttcagcaccc cgcggtccac ccatggcacc cataataatt | 540 |
| tcacagagaa ccgcaagtca gctggcagca cctataataa tttcgcagag aactgcaaga | 600 |
| atacctcaag ttcacactat ggacagttct ggaaaaacca cactgactcc tgtggttata | 660 |
| ttaacaggtt acatggatga agaacttgca aaaaaatctt gttccaaaat ccagattcta | 720 |
| aaatgtggag gcactgcaag gtctcagaat agccgagaag aaaacaagga agcactaaag | 780 |
| aatgacatca tatttacgaa ttctgtagaa tccttgaaat cagcacacat aaaggagcca | 840 |
| gaaagagaag gaaaaggcac tgatttagag aaagacaaaa taggaatgga ggtcaaggta | 900 |
| gacagtgacg ctggaatacc aaaaagacag gaaacccaac taaaaatcag tgagatgagt | 960 |
| ataccacaag gacagggagc ccaaataaag aaaagtgtgt cagatgtacc aagaggacag | 1020 |
| gagtcccaag taagaagag tgagtcaggt gtcccaaaag gacaagaagc ccaagtaacg | 1080 |
| aagagtgggt tggttgtact gaaaggacag gaagcccagg tagagaagag tgagatgggt | 1140 |
| gtgccaagaa gacaggaatc ccaagtaaag aagagtcagt ctggtgtctc aaagggacag | 1200 |
| gaagcccagg taaagaagag ggagtcagtt gtactgaaag gacaggaagc ccaggtagag | 1260 |
| aagagtgagt tgaaggtacc aaaaggacaa gaaggccaag tagagaagac tgaggcagat | 1320 |

| | |
|---|---:|
| gtgccaaagg aacaagaggt ccaagaaaag aagagtgagg caggtgtact gaaaggacca | 1380 |
| gaatcccaag taaagaacac tgaggtgagt gtaccagaaa cactggaatc ccaagtaaag | 1440 |
| aagagtgagt caggtgtact aaaaggacag gaagcccaag aaaagaagga gagttttgag | 1500 |
| gataaaggaa ataatgataa agaaaaggag agagatgcag agaaagatcc aaataaaaaa | 1560 |
| gaaaaaggtg acaaaaacac aaaaggtgac aaaggaaagg acaaagttaa aggaaagaga | 1620 |
| gaatcagaaa tcaatggtga aaaatcaaaa ggctcgaaaa gggcgaaggc aaatacagga | 1680 |
| aggaagtaca acaaaaaagt ggaagagtaa | 1710 |

<210> SEQ ID NO 33
<211> LENGTH: 1665
<212> TYPE: DNA
<213> ORGANISM: Homo sapiens

<400> SEQUENCE: 33

| | |
|---|---:|
| atgacagtct tggaaataac tttggctgtc atcctgactc tactgggact tgccatcctg | 60 |
| gctatttgt taacaagatg ggcacgatgt aagcaaagtg aaatgtatat ctccagatac | 120 |
| agttcagaac aaagtgctag acttctggac tatgaggatg gtagaggatc ccgacatgca | 180 |
| tattcaacac aaagtgagag atccaaaaga gattacacac catcaaccaa ctctctagca | 240 |
| ctgtctcgat caagtattgc tttacctcaa ggatccatga gtagtataaa atgtttacaa | 300 |
| acaactgaag aacctccttc cagaactgca ggagccatga tgcaattcac agcccctatt | 360 |
| cccggagcta caggacctat caagctctct caaaaaacca ttgtgcaaac tccaggacct | 420 |
| attgtacaat atcctggatc caatgctggt ccaccttcag caccccgcgg tccacccatg | 480 |
| gcacccataa taatttcaca gagaaccgca agtcagctgg cagcacctat aataatttcg | 540 |
| cagagaactg caagaatacc tcaagttcac actatggaca gttctggaaa aatcacactg | 600 |
| actcctgtgg ttatattaac aggttacatg gatgaagaac ttgcaaaaaa atcttgttcc | 660 |
| aaaatccaga ttctaaaatg tggaggcact gcaaggtctc agaatagccg agaagaaaac | 720 |
| aaggaagcac taaagaatga catcatattt acgaattctg tagaatcctt gaaatcagca | 780 |
| cacataaagg agccagaaag agaaggaaaa ggcactgatt tagagaaaga caaaatagga | 840 |
| atggaggtca aggtagacag tgacgctgga ataccaaaaa gacaggaaac ccaactaaaa | 900 |
| atcagtgaga tgagtatacc acaaggacag ggagcccaaa taagaaaaag tgtgtcagat | 960 |
| gtaccaagag gacaggagtc ccaagtaaag aagagtgagt caggtgtccc aaaaggacaa | 1020 |
| gaagcccaag taacgaagag tgggttggtt gtactgaaag gacaggaagc ccaggtagag | 1080 |
| aagagtgaga tgggtgtgcc aagaagacag gaatcccaag taaagaagag tcagtctggt | 1140 |
| gtctcaaagg acaggaagc ccaggtaaag aagggagtg cagttgtact gaaaggacag | 1200 |
| gaagcccagg tagagaagag tgagttgaag gtaccaaaag gacaagaagg ccaagtagag | 1260 |
| aagactgagg cagatgtgcc aaaggaacaa gaggtccaag aaaagaagag tgaggcaggt | 1320 |
| gtactgaaag gaccagaatc ccaagtaaag aacactgagg tgagtgtacc agaaacactg | 1380 |
| gaatcccaag taaagaagag tgagtcaggt gtactaaaag gacaggaagc ccaagaaaag | 1440 |
| aaggagagtt ttgaggataa aggaaataat gataaagaaa aggagagaga tgcagagaaa | 1500 |
| gatccaaaata aaaagaaaa aggtgacaaa aacacaaaag gtgacaaagg aaaggacaaa | 1560 |
| gttaaaggaa agagaatc agaaatcaat ggtgaaaaat caaaaggctc gaaaagggcg | 1620 |
| aaggcaaata caggaaggaa gtacaacaaa aaagtggaag agtaa | 1665 |

-continued

```
<210> SEQ ID NO 34
<211> LENGTH: 561
<212> TYPE: PRT
<213> ORGANISM: Homo sapiens

<400> SEQUENCE: 34
```

Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Cys Lys Gln
            20                  25                  30

Ser Glu Met Tyr Ile Ser Arg Tyr Ser Ser Glu Gln Ser Ala Arg Leu
        35                  40                  45

Leu Asp Tyr Glu Asp Gly Arg Gly Ser Arg His Ala Tyr Ser Thr Gln
    50                  55                  60

Ser Asp Thr Ser Tyr Asp Asn Arg Glu Arg Ser Lys Arg Asp Tyr Thr
65                  70                  75                  80

Pro Ser Thr Asn Ser Leu Ala Leu Ser Arg Ser Ser Ile Ala Leu Pro
                85                  90                  95

Gln Gly Ser Met Ser Ser Ile Lys Cys Leu Gln Thr Thr Glu Glu Pro
            100                 105                 110

Pro Ser Arg Thr Ala Gly Ala Met Met Gln Phe Thr Ala Pro Ile Pro
        115                 120                 125

Gly Ala Thr Gly Pro Ile Lys Leu Ser Gln Lys Thr Ile Val Gln Thr
    130                 135                 140

Pro Gly Pro Ile Val Gln Tyr Pro Gly Ser Asn Ala Gly Pro Pro Ser
145                 150                 155                 160

Ala Pro Arg Gly Pro Pro Met Ala Pro Ile Ile Ile Ser Gln Arg Thr
                165                 170                 175

Ala Ser Gln Leu Ala Ala Pro Ile Ile Ile Ser Gln Arg Thr Ala Arg
            180                 185                 190

Ile Pro Gln Val His Thr Met Asp Ser Ser Gly Lys Ile Thr Leu Thr
        195                 200                 205

Pro Val Val Ile Leu Thr Gly Tyr Met Asp Glu Glu Leu Ala Lys Lys
    210                 215                 220

Ser Cys Ser Lys Ile Gln Ile Leu Lys Cys Gly Gly Thr Ala Arg Ser
225                 230                 235                 240

Gln Asn Ser Arg Glu Glu Asn Lys Glu Ala Leu Lys Asn Asp Ile Ile
                245                 250                 255

Phe Thr Asn Ser Val Glu Ser Leu Lys Ser Ala His Ile Lys Glu Pro
            260                 265                 270

Glu Arg Glu Gly Lys Gly Thr Asp Leu Glu Lys Asp Lys Ile Gly Met
        275                 280                 285

Glu Val Lys Val Asp Ser Asp Ala Gly Ile Pro Lys Arg Gln Glu Thr
    290                 295                 300

Gln Leu Lys Ile Ser Glu Met Ser Ile Pro Gln Gly Gln Gly Ala Gln
305                 310                 315                 320

Ile Lys Lys Ser Val Ser Asp Val Pro Arg Gly Gln Glu Ser Gln Val
                325                 330                 335

Lys Lys Ser Glu Ser Gly Val Pro Lys Gly Gln Glu Ala Gln Val Thr
            340                 345                 350

Lys Ser Gly Leu Val Val Leu Lys Gly Gln Glu Ala Gln Val Glu Lys
        355                 360                 365

Ser Glu Met Gly Val Pro Arg Arg Gln Glu Ser Gln Val Lys Lys Ser
    370                 375                 380

```
Gln Ser Gly Val Ser Lys Gly Gln Glu Ala Gln Val Lys Lys Arg Glu
385                 390                 395                 400

Ser Val Val Leu Lys Gly Gln Glu Ala Gln Val Glu Lys Ser Glu Leu
            405                 410                 415

Lys Val Pro Lys Gly Gln Glu Gly Gln Val Glu Lys Thr Glu Ala Asp
        420                 425                 430

Val Pro Lys Glu Gln Glu Val Gln Glu Lys Lys Ser Glu Ala Gly Val
    435                 440                 445

Leu Lys Gly Pro Glu Ser Gln Val Lys Asn Thr Glu Val Ser Val Pro
    450                 455                 460

Glu Thr Leu Glu Ser Gln Val Lys Ser Glu Ser Gly Val Leu Lys
465                 470                 475                 480

Gly Gln Glu Ala Gln Glu Lys Lys Glu Ser Phe Glu Asp Lys Gly Asn
                485                 490                 495

Asn Asp Lys Glu Lys Glu Arg Asp Ala Glu Lys Asp Pro Asn Lys Lys
                500                 505                 510

Glu Lys Gly Asp Lys Asn Thr Lys Gly Asp Lys Gly Lys Asp Lys Val
            515                 520                 525

Lys Gly Lys Arg Glu Ser Glu Ile Asn Gly Glu Lys Ser Lys Gly Ser
        530                 535                 540

Lys Arg Ala Lys Ala Asn Thr Gly Arg Lys Tyr Asn Lys Lys Val Glu
545                 550                 555                 560

Glu

<210> SEQ ID NO 35
<211> LENGTH: 569
<212> TYPE: PRT
<213> ORGANISM: Homo sapiens

<400> SEQUENCE: 35

Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Arg Lys Gln
            20                  25                  30

Ser Glu Met His Ile Ser Arg Tyr Ser Ser Gln Ser Ala Arg Leu
        35                  40                  45

Leu Asp Tyr Glu Asp Gly Arg Gly Ser Arg His Ala Tyr Ser Thr Gln
    50                  55                  60

Ser Asp Thr Ser Cys Asp Asn Arg Glu Arg Ser Lys Arg Asp Tyr Thr
65                  70                  75                  80

Pro Ser Thr Asn Ser Leu Ala Leu Ser Arg Ser Ser Ile Ala Leu Pro
                85                  90                  95

Gln Gly Ser Met Ser Ser Ile Lys Cys Leu Gln Thr Thr Glu Glu Leu
            100                 105                 110

Pro Ser Arg Thr Ala Gly Ala Met Met Gln Phe Thr Ala Pro Ile Pro
        115                 120                 125

Gly Ala Thr Gly Pro Ile Lys Leu Ser Gln Lys Thr Ile Val Gln Thr
    130                 135                 140

Pro Gly Pro Ile Val Gln Tyr Pro Gly Pro Asn Val Arg Ser His Pro
145                 150                 155                 160

His Thr Ile Thr Gly Pro Pro Ser Ala Pro Arg Gly Pro Pro Met Ala
                165                 170                 175

Pro Ile Ile Ile Ser Gln Arg Thr Ala Ser Gln Leu Ala Ala Pro Ile
            180                 185                 190
```

Ile Ile Ser Gln Arg Thr Ala Arg Ile Pro Gln Val His Thr Met Asp
            195                 200                 205

Ser Ser Gly Lys Thr Thr Leu Thr Pro Val Val Ile Leu Thr Gly Tyr
210                 215                 220

Met Asp Glu Glu Leu Ala Lys Lys Ser Cys Ser Lys Ile Gln Ile Leu
225                 230                 235                 240

Lys Cys Gly Gly Thr Ala Arg Ser Gln Asn Ser Arg Glu Glu Asn Lys
                245                 250                 255

Glu Ala Leu Lys Asn Asp Ile Ile Phe Thr Asn Ser Val Glu Ser Leu
            260                 265                 270

Lys Ser Ala His Ile Lys Glu Pro Glu Arg Glu Gly Lys Gly Thr Asp
        275                 280                 285

Leu Glu Lys Asp Lys Ile Gly Met Glu Val Lys Val Asp Ser Asp Ala
290                 295                 300

Gly Ile Pro Lys Arg Gln Glu Thr Gln Leu Lys Ile Ser Glu Met Ser
305                 310                 315                 320

Ile Pro Gln Gly Gln Gly Ala Gln Ile Lys Lys Ser Val Ser Asp Val
                325                 330                 335

Pro Arg Gly Gln Glu Ser Gln Val Lys Lys Ser Glu Ser Gly Val Pro
            340                 345                 350

Lys Gly Gln Glu Ala Gln Val Thr Lys Ser Gly Leu Val Val Leu Lys
        355                 360                 365

Gly Gln Glu Ala Gln Val Glu Lys Ser Glu Met Gly Val Pro Arg Arg
370                 375                 380

Gln Glu Ser Gln Val Lys Lys Ser Gln Ser Gly Val Ser Lys Gly Gln
385                 390                 395                 400

Glu Ala Gln Val Lys Lys Arg Glu Ser Val Val Leu Lys Gly Gln Glu
                405                 410                 415

Ala Gln Val Glu Lys Ser Glu Leu Lys Val Pro Lys Gly Gln Glu Gly
            420                 425                 430

Gln Val Glu Lys Thr Glu Ala Asp Val Pro Lys Glu Gln Glu Val Gln
        435                 440                 445

Glu Lys Lys Ser Glu Ala Gly Val Leu Lys Gly Pro Glu Ser Gln Val
450                 455                 460

Lys Asn Thr Glu Val Ser Val Pro Glu Thr Leu Glu Ser Gln Val Lys
465                 470                 475                 480

Lys Ser Glu Ser Gly Val Leu Lys Gly Gln Glu Ala Gln Glu Lys Lys
                485                 490                 495

Glu Ser Phe Glu Asp Lys Gly Asn Asn Asp Lys Glu Lys Glu Arg Asp
            500                 505                 510

Ala Glu Lys Asp Pro Asn Lys Glu Lys Gly Asp Lys Asn Thr Lys
        515                 520                 525

Gly Asp Lys Gly Lys Asp Lys Val Lys Gly Lys Arg Glu Ser Glu Ile
530                 535                 540

Asn Gly Glu Lys Ser Lys Gly Ser Lys Arg Ala Lys Ala Asn Thr Gly
545                 550                 555                 560

Arg Lys Tyr Asn Lys Lys Val Glu Glu
                565

<210> SEQ ID NO 36
<211> LENGTH: 554
<212> TYPE: PRT
<213> ORGANISM: Homo sapiens

<400> SEQUENCE: 36

```
Met Thr Val Leu Glu Ile Thr Leu Ala Val Ile Leu Thr Leu Leu Gly
1               5                   10                  15

Leu Ala Ile Leu Ala Ile Leu Leu Thr Arg Trp Ala Arg Cys Lys Gln
                20                  25                  30

Ser Glu Met Tyr Ile Ser Arg Tyr Ser Ser Glu Gln Ser Ala Arg Leu
        35                  40                  45

Leu Asp Tyr Glu Asp Gly Arg Gly Ser Arg His Ala Tyr Ser Thr Gln
    50                  55                  60

Ser Glu Arg Ser Lys Arg Asp Tyr Thr Pro Ser Thr Asn Ser Leu Ala
65                  70                  75                  80

Leu Ser Arg Ser Ser Ile Ala Leu Pro Gln Gly Ser Met Ser Ser Ile
                85                  90                  95

Lys Cys Leu Gln Thr Thr Glu Glu Pro Pro Ser Arg Thr Ala Gly Ala
                100                 105                 110

Met Met Gln Phe Thr Ala Pro Ile Pro Gly Ala Thr Gly Pro Ile Lys
                115                 120                 125

Leu Ser Gln Lys Thr Ile Val Gln Thr Pro Gly Pro Ile Val Gln Tyr
    130                 135                 140

Pro Gly Ser Asn Ala Gly Pro Pro Ser Ala Pro Arg Gly Pro Pro Met
145                 150                 155                 160

Ala Pro Ile Ile Ile Ser Gln Arg Thr Ala Ser Gln Leu Ala Ala Pro
                165                 170                 175

Ile Ile Ile Ser Gln Arg Thr Ala Arg Ile Pro Gln Val His Thr Met
                180                 185                 190

Asp Ser Ser Gly Lys Ile Thr Leu Thr Pro Val Val Ile Leu Thr Gly
                195                 200                 205

Tyr Met Asp Glu Glu Leu Ala Lys Lys Ser Cys Ser Lys Ile Gln Ile
    210                 215                 220

Leu Lys Cys Gly Gly Thr Ala Arg Ser Gln Asn Ser Arg Glu Glu Asn
225                 230                 235                 240

Lys Glu Ala Leu Lys Asn Asp Ile Ile Phe Thr Asn Ser Val Glu Ser
                245                 250                 255

Leu Lys Ser Ala His Ile Lys Glu Pro Glu Arg Glu Gly Lys Gly Thr
                260                 265                 270

Asp Leu Glu Lys Asp Lys Ile Gly Met Glu Val Lys Val Asp Ser Asp
    275                 280                 285

Ala Gly Ile Pro Lys Arg Gln Glu Thr Gln Leu Lys Ile Ser Glu Met
    290                 295                 300

Ser Ile Pro Gln Gly Gln Gly Ala Gln Ile Lys Lys Ser Val Ser Asp
305                 310                 315                 320

Val Pro Arg Gly Gln Glu Ser Gln Val Lys Lys Ser Glu Ser Gly Val
                325                 330                 335

Pro Lys Gly Gln Glu Ala Gln Val Thr Lys Ser Gly Leu Val Val Leu
                340                 345                 350

Lys Gly Gln Glu Ala Gln Val Glu Lys Ser Glu Met Gly Val Pro Arg
                355                 360                 365

Arg Gln Glu Ser Gln Val Lys Lys Ser Gln Ser Gly Val Ser Lys Gly
    370                 375                 380

Gln Glu Ala Gln Val Lys Lys Arg Glu Ser Val Val Leu Lys Gly Gln
385                 390                 395                 400

Glu Ala Gln Val Glu Lys Ser Glu Leu Lys Val Pro Lys Gly Gln Glu
                405                 410                 415
```

```
Gly Gln Val Glu Lys Thr Glu Ala Asp Val Pro Lys Glu Gln Val
            420                 425                 430
Gln Glu Lys Lys Ser Glu Ala Gly Val Leu Lys Gly Pro Glu Ser Gln
        435                 440                 445
Val Lys Asn Thr Glu Val Ser Val Pro Glu Thr Leu Glu Ser Gln Val
    450                 455                 460
Lys Lys Ser Glu Ser Gly Val Leu Lys Gly Gln Ala Gln Glu Lys
465                 470                 475                 480
Lys Glu Ser Phe Glu Asp Lys Gly Asn Asn Asp Lys Glu Lys Glu Arg
                485                 490                 495
Asp Ala Glu Lys Asp Pro Asn Lys Lys Glu Lys Gly Asp Lys Asn Thr
            500                 505                 510
Lys Gly Asp Lys Gly Lys Asp Lys Val Lys Gly Lys Arg Glu Ser Glu
        515                 520                 525
Ile Asn Gly Glu Lys Ser Lys Gly Ser Lys Arg Ala Lys Ala Asn Thr
    530                 535                 540
Gly Arg Lys Tyr Asn Lys Lys Val Glu Glu
545                 550

<210> SEQ ID NO 37
<211> LENGTH: 1182
<212> TYPE: DNA
<213> ORGANISM: Homo sapiens

<400> SEQUENCE: 37
acacaggttg gagcagagaa agaggaaaca tagaggtgcc aaaggaacaa agacataatg      60
atgtcatcca agccaacaag ccatgctgaa gtaaatgaaa ccatacccaa cccttaccca     120
ccaggcagct ttatggctcc tggatttcaa cagcctctgg gttcaatcaa cttagaaaac     180
caagctcagg gtgctcagcg tgctcagccc tacggcatca catctccggg aatctttgct     240
agcagtcaac cgggtcaagg aaatatacaa atgataaatc caagtgtggg aacagcagta     300 atgaactta aagaagaagc aaaggcacta ggggtgatcc agatcatggt tggattgatg     360
cacattggtt ttggaattgt tttgtgttta atatccttct cttttagaga agtattaggt     420
tttgcctcta ctgctgttat tggtggatac ccattctggg gtggcctttc ttttattatc     480
tctggctctc tctctgtgtc agcatccaag gagctttccc gttgtctggt gaaaggcagc     540
ctgggaatga acattgttag ttctatcttg gccttcattg gagtgattct gctgctggtg     600
gatatgtgca tcaatggggt agctggccaa gactactggg ccgtgctttc tggaaaaggc     660
atttcagcca cgctgatgat cttctccctc ttggagttct tcgtagcttg tgccacagcc     720
cattttgcca accaagcaaa caccacaacc aatatgtctg tcctggttat tccaaatatg     780
tatgaaagca accctgtgac accagcgtct tcttcagctc ctcccagatg caacaactac     840
tcagctaatg cccctaaata gtaaaagaaa aaggggtatc agtctaatct catggagaaa     900
aactacttgc aaaaacttct taagaagatg tcttttattg tctacaatga tttctagtct     960
ttaaaaactg tgtttgagat tgttttttag gttggtcgct aatgatggct gtatctccct    1020
tcactgtctc ttcctacatt accactacta catgctggca aggtgaagg atcagaggac     1080 tgaaaaatga ttctgcaact ctcttaaagt tagaaatgtt tctgttcata ttactttttc    1140
cttaataaaa tgtcattaga aacaaaaaaa aaaaaaaaaa aa                       1182

<210> SEQ ID NO 38
<211> LENGTH: 267
<212> TYPE: PRT
```

<213> ORGANISM: Homo sapiens

<400> SEQUENCE: 38

```
Met Met Ser Ser Lys Pro Thr Ser His Ala Glu Val Asn Glu Thr Ile
1               5                   10                  15

Pro Asn Pro Tyr Pro Pro Gly Ser Phe Met Ala Pro Gly Phe Gln Gln
            20                  25                  30

Pro Leu Gly Ser Ile Asn Leu Glu Asn Gln Ala Gln Gly Ala Gln Arg
        35                  40                  45

Ala Gln Pro Tyr Gly Ile Thr Ser Pro Gly Ile Phe Ala Ser Ser Gln
    50                  55                  60

Pro Gly Gln Gly Asn Ile Gln Met Ile Asn Pro Ser Val Gly Thr Ala
65                  70                  75                  80

Val Met Asn Phe Lys Glu Glu Ala Lys Ala Leu Gly Val Ile Gln Ile
                85                  90                  95

Met Val Gly Leu Met His Ile Gly Phe Gly Ile Val Leu Cys Leu Ile
            100                 105                 110

Ser Phe Ser Phe Arg Glu Val Leu Gly Phe Ala Ser Thr Ala Val Ile
        115                 120                 125

Gly Gly Tyr Pro Phe Trp Gly Gly Leu Ser Phe Ile Ile Ser Gly Ser
    130                 135                 140

Leu Ser Val Ser Ala Ser Lys Glu Leu Ser Arg Cys Leu Val Lys Gly
145                 150                 155                 160

Ser Leu Gly Met Asn Ile Val Ser Ser Ile Leu Ala Phe Ile Gly Val
                165                 170                 175

Ile Leu Leu Leu Val Asp Met Cys Ile Asn Gly Val Ala Gly Gln Asp
            180                 185                 190

Tyr Trp Ala Val Leu Ser Gly Lys Gly Ile Ser Ala Thr Leu Met Ile
        195                 200                 205

Phe Ser Leu Leu Glu Phe Phe Val Ala Cys Ala Thr Ala His Phe Ala
    210                 215                 220

Asn Gln Ala Asn Thr Thr Thr Asn Met Ser Val Leu Val Ile Pro Asn
225                 230                 235                 240

Met Tyr Glu Ser Asn Pro Val Thr Pro Ala Ser Ser Ser Ala Pro Pro
                245                 250                 255

Arg Cys Asn Asn Tyr Ser Ala Asn Ala Pro Lys
            260                 265
```

<210> SEQ ID NO 39
<211> LENGTH: 1948
<212> TYPE: DNA
<213> ORGANISM: Homo sapiens

<400> SEQUENCE: 39

```
gcacgaggtt ttgaggacca gcaacacagc aatacttcca gatctccata taacctctgt      60
tcatttggga ggggctttgt attttcaaca ggagagttca aagttcattt tttttttcagc    120 aactacagtt ctaagtgaaa tctatttta ttgatacatg gtattttaca tgtttatggg     180
atacatatga gtcataatct attttaaata ataccttagt gttgtaaaat caacagtgct     240
ttttaaaaga aatataccct tgttaattatc ccacatgtgt ctccagaagt acagcttgaa    300
caaatccacc ttctgtggac caagcaccac cctgggcatt tctagcatga gcaaaatcca    360
aggtcctggc tggactccag agatgctatt tacctcagaa gcatgacaat aggaggcaga    420
aggagcaggc aaatccaagt cctttcttgt agtttccttg tttggggagg aaaagttgag    480
```

| | |
|---|---|
| ttttactatt atggaaaaga aacaggaaat agagacagac aaagagatat gacaatacag | 540 |
| tcctgccacc cagatactca tttccaccta ccattccatg catttgtttt gaatatataa | 600 |
| gtatgtacat aaaggtaggt actctcaagt ccatcagggc ttggctgtcc actgttttg | 660 |
| aagttccaga atgttttgc taagttgagg aaataccaaa tcaggactat gaaaattatg | 720 |
| gtatatattg atgtgtcaca gaacacagat gtgacataat aaagatgtgt aagattatat | 780 |
| ataaacttg tgtgtacacc tacctcatct ggggataaca cctcaagttt aattttgagg | 840 |
| cttgggtcaa tcgtgcttcc cttcccttc ataggtcctc tatgagatat tgtcatagat | 900 |
| tccatgttat gcaatagcca tagaatatga catctctcta tgataattct atattacttt | 960 |
| aattgctgca cagaagttca ttgtatgtaa gtgccacagt atattataga tcttcttgtg | 1020 |
| ggacatctat ttctagttta tgtgatagta tagcactttc atgaatgttc ttgtacttga | 1080 |
| tctttacaca ttttctttt tccttaggat gaattctgag agatgtaatt gatggggcaa | 1140 |
| aatgtactca ctgtttgagg tttgaaattt ttccatcaaa agctggtact cttggttttt | 1200 |
| taagacaaag agcaaatcct cccctgccag gattgacttt tggctctttt ttttcaaacc | 1260 |
| tcactgcttt ttggtttagt tgtcataaaa tgccaagcac catgaacagg gctccatgaa | 1320 |
| ggggctcaga ggtaggaggg ctgtgattag agagaggctt ggactgatgg gcaattgag | 1380 |
| tgctcagaat tagagtgagg gggtggggt gctgcaggga cagatgctgg ggaaagacac | 1440 |
| cctgaagggc aaagggagca acaatggctg cagtacatgt ggcctttcag ctagcgcaga | 1500 |
| ggatggaaac cagagtgggc tgatgattgg atgccaggcc tgagccagca actgtgatcc | 1560 |
| tgagctgtgc acacttctgg ttgggattat ttctggtttc tacttcctgt ttgaagatgt | 1620 |
| ggcatggaga gtgctctgct ttgacctgaa gtattttatc tatcctcagt ctcaggacac | 1680 |
| tgttgatgga attaaggcca agcacatctg caaaaaagac attgctggag gaggtgcaaa | 1740 |
| gagctggaaa ccaagtctcc agtcctggga aaagcagtgg tatggaaaag caatggaaag | 1800 |
| agcattttga aaatgccatt ccactgtttt ctggccttta tgatttctgc tgagaaatcc | 1860 |
| actgttagtc tgatggggtc tccttcatag caccaatgac ctgaagagcc ttgttgaagg | 1920 |
| aagactccat ctgatgactc agagcaag | 1948 |

<210> SEQ ID NO 40
<211> LENGTH: 1406
<212> TYPE: DNA
<213> ORGANISM: Homo sapiens

<400> SEQUENCE: 40

| | |
|---|---|
| cggtgagagg ggcgcgcagc agcagctcct caacgccgca acgcgccggc ccaactgcag | 60 |
| gaaggtctgt gctctggagc cagggtaaat ggttataaaa ttatacacca tggccctcct | 120 |
| aaagacactc taggaaaacc atgtcatcct gatcttaaaa cacctgcaag aaagagcaca | 180 |
| gtacttcacc attaataaag tagatatttc atcctgctca gaaaaccaac atttccagca | 240 |
| atggctttac taccggtgtt gtttctggtt actgtgctgc ttccatcttt acctgcagaa | 300 |
| ggaaaggatc ccgcttttac tgctttgtta accacccagt tgcaagtgca aagggagatt | 360 |
| gtaaataaac acaatgaact aaggaaagca gtctctccac ctgccagtaa catgctaaag | 420 |
| atggaatgga gcagagaggt aacaacgaat gcccaaaggt gggcaaacaa gtgcacttta | 480 |
| caacatagtg atccagagga ccgcaaaaac agtacaagat gtggtgagaa tctctatatg | 540 |
| tcaagtgacc ctacttcctg gtcttctgca atccaaagct ggtatgacga gatcctagat | 600 |
| tttgtctatg gtgtaggacc aaagagtccc aatgcagttg ttggacatta tactcagctt | 660 |

```
gtttggtact cgacttacca ggtaggctgt ggaattgcct actgtcccaa tcaagatagt    720
ctaaaatact actatgtttg ccaatattgt cctgctggta ataatatgaa tagaaagaat    780
accccgtacc aacaaggaac accttgtgcc ggttgccctg atgactgtga caaaggacta    840
tgcaccaata gttgccagta tcaagatctc ctaagtaact gtgattcctt gaagaataca    900
gctggctgtg aacatgagtt actcaaggaa aagtgcaagg ctacttgcct atgtgagaac    960
aaaatttact gatttaccta gtgagcattg tgcaagactg catggataag ggctgcatca   1020
tttaattgcg acataccagt ggaaattgta tgtatgttag tgacaaattt gatttcaaag   1080
agcaatgcat cttctccccc agatcatcac agaaatcact ttcaggcaat gatttacaaa   1140
agtagcatag tagatgatga caactgtgaa ctctgacata aatttagtgc tttataacga   1200
actgaatcag gttgaggatt ttgaaaactg tataaccata ggatttaggt cactaggact   1260
ttggatcaaa atggtgcatt acgtatttcc tgaaacatgc taaagaagaa gactgtaaca   1320
tcattgccat tcctactacc tgagtttta cttgcataaa caataaattc aaagctttac   1380
atctgcaaaa aaaaaaaaaa aaaaaa                                        1406
```

<210> SEQ ID NO 41
<211> LENGTH: 243
<212> TYPE: PRT
<213> ORGANISM: Homo sapiens

<400> SEQUENCE: 41

```
Met Ala Leu Leu Pro Val Leu Phe Leu Val Thr Val Leu Leu Pro Ser
1               5                   10                  15

Leu Pro Ala Glu Gly Lys Asp Pro Ala Phe Thr Ala Leu Leu Thr Thr
            20                  25                  30

Gln Leu Gln Val Gln Arg Glu Ile Val Asn Lys His Asn Glu Leu Arg
        35                  40                  45

Lys Ala Val Ser Pro Pro Ala Ser Asn Met Leu Lys Met Glu Trp Ser
    50                  55                  60

Arg Glu Val Thr Thr Asn Ala Gln Arg Trp Ala Asn Lys Cys Thr Leu
65                  70                  75                  80

Gln His Ser Asp Pro Glu Asp Arg Lys Thr Ser Thr Arg Cys Gly Glu
                85                  90                  95

Asn Leu Tyr Met Ser Ser Asp Pro Thr Ser Trp Ser Ser Ala Ile Gln
            100                 105                 110

Ser Trp Tyr Asp Glu Ile Leu Asp Phe Val Tyr Gly Val Gly Pro Lys
        115                 120                 125

Ser Pro Asn Ala Val Val Gly His Tyr Thr Gln Leu Val Trp Tyr Ser
    130                 135                 140

Thr Tyr Gln Val Gly Cys Gly Ile Ala Tyr Cys Pro Asn Gln Asp Ser
145                 150                 155                 160

Leu Lys Tyr Tyr Tyr Val Cys Gln Tyr Cys Pro Ala Gly Asn Asn Met
                165                 170                 175

Asn Arg Lys Asn Thr Pro Tyr Gln Gln Gly Thr Pro Cys Ala Gly Cys
            180                 185                 190

Pro Asp Asp Cys Asp Lys Gly Leu Cys Thr Asn Ser Cys Gln Tyr Gln
        195                 200                 205

Asp Leu Leu Ser Asn Cys Asp Ser Leu Lys Asn Thr Ala Gly Cys Glu
    210                 215                 220

His Glu Leu Leu Lys Glu Lys Cys Lys Ala Thr Cys Leu Cys Glu Asn
225                 230                 235                 240
```

Lys Ile Tyr

<210> SEQ ID NO 42
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 42
tctagcactg tctcgatcaa g                                             21

<210> SEQ ID NO 43
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 43
tgtcctcttg gtacatctga c                                             21

<210> SEQ ID NO 44
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 44
ctgtgtcagc atccaaggag c                                             21

<210> SEQ ID NO 45
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 45
ttcacctttg ccagcatgta g                                             21

<210> SEQ ID NO 46
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 46
cttgctctga gtcatcagat g                                             21

<210> SEQ ID NO 47
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 47
cacagaatat gagccataca g                                              21

<210> SEQ ID NO 48
<211> LENGTH: 22
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 48
ggtgtcactt ctgtgccttc ct                                             22

<210> SEQ ID NO 49
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 49
cggcaccagt tccaacaata g                                              21

<210> SEQ ID NO 50
<211> LENGTH: 18
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 50
caaaggttct ccaaatgt                                                  18

<210> SEQ ID NO 51
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 51
tagcgcctca actgtcgttg g                                              21

<210> SEQ ID NO 52
<211> LENGTH: 23
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 52
cgtgagcgct tcgagatgtt ccg                                            23

<210> SEQ ID NO 53
<211> LENGTH: 23
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 53
cctaaccagc tgcccaactg tag                                            23

<210> SEQ ID NO 54
<211> LENGTH: 1550
<212> TYPE: DNA
<213> ORGANISM: Homo sapiens

<400> SEQUENCE: 54

| | | |
|---|---|---|
| atgaatgaaa gtcctgatcc gactgacctg gcgggagtca tcattgagct cggccccaat | 60 |
| gacagtccac agacaagtga atttaaagga gcaaccgagg aggcacctgc gaaagaaagc | 120 |
| ccacacacaa gtgaatttaa aggagcagcc cgggtgtcac ctatcagtga aagtgtgtta | 180 |
| gcacgacttt ccaagtttga agttgaagat gctgaaaatg ttgcttcata tgacagcaag | 240 |
| attaagaaaa ttgtgcattc aattgtatca tcctttgcat ttggactatt tggagttttc | 300 |
| ctggtcttac tggatgtcac tctcatcctt gccgacctaa ttttcactga cagcaaactt | 360 |
| tatattcctt tggagtatcg ttctatttct ctagctattg ccttatttt tctcatggat | 420 |
| gttcttcttc gagtatttgt agaaaggaga cagcagtatt tttctgactt atttaacatt | 480 |
| ttagatactg ccattattgt gattcttctg ctggttgatg tcgtttacat ttttttttgac | 540 |
| attaagttgc ttaggaatat tcccagatgg acacatttac ttcgacttct acgacttatt | 600 |
| attctgttaa gaattttca tctgtttcat caaaaaagac aacttgaaaa gctgataaga | 660 |
| aggcgggttt cagaaaacaa aaggcgatac acaagggatg gatttgacct agacctcact | 720 |
| tacgttacag aacgtattat tgctatgtca tttccatctt ctggaaggca gtctttctat | 780 |
| agaaatccaa tcaaggaagt tgtgcggttt ctagataaga aacaccgaaa ccactatcga | 840 |
| gtctacaatc tatgcagtga aagagcttac gatcctaagc acttccataa tagggtcgtt | 900 |
| agaatcatga ttgatgatca taatgtcccc actctacatc agatggtggt tttcaccaag | 960 |
| gaagtaaatg agtggatggc tcaagatctt gaaaacatcg tagcgattca ctgtaaagga | 1020 |
| ggcacagata gaacaggaac tatggttttgt gccttcctta ttgcctctga aatatgttca | 1080 |
| actgcaaagg aaagcctgta ttattttgga gaaaggcgaa cagataaaac ccacagcgaa | 1140 |
| aaatttcagg gagtagaaac tccttctcag gttatgtacg tgatctaaaa atccaaatag | 1200 |
| aaatggagaa aaaggttgtc ttttccacta tttcattagg aaaatgttcg gtacttgata | 1260 |
| acattacaac agacaaaata ttaattgatg tattcgacgg tccacctctg tatgatgatg | 1320 |
| tgaaagtgca gttttctat tcgaatcttc ctacatacta tgacaattgc tcattttact | 1380 |
| tctggttgca cacatctttt attgaaaata acaggcttta tctaccaaaa aatgaattgg | 1440 |
| ataatctaca taaacaaaaa gcacggagaa tttatccatc agattttgcc gtggagatac | 1500 |
| tttttggcga gaaaatgact tccagtgatg ttgtagctgg atccgattaa | 1550 |

<210> SEQ ID NO 55
<211> LENGTH: 1407
<212> TYPE: DNA
<213> ORGANISM: Homo sapiens

<400> SEQUENCE: 55

| | | |
|---|---|---|
| atgaatgaaa gtcctgatcc gactgacctg gcgggagtca tcattgagct cggccccaat | 60 |
| gacagtccac agacaagtga atttaaagga gcaaccgagg aggcacctgc gaaagaaagc | 120 |
| ccacacacaa gtgaatttaa aggagcagcc cgggtgtcac ctatcagtga aagtgtgtta | 180 |
| gcacgacttt ccaagtttga agttgaagat gctgaaaatg ttgcttcata tgacagcaag | 240 |
| attaagaaaa ttgtgcattc aattgtatca tcctttgcat ttggactatt tggagttttc | 300 |

```
ctggtcttac tggatgtcac tctcatcctt gccgacctaa ttttcactga cagcaaactt      360
tatattcctt tggagtatcg ttctatttct ctagctattg ccttattttt tctcatggat      420
gttcttcttc gagtatttgt agaaaggaga cagcagtatt tttctgactt atttaacatt      480
ttagatactg ccattattgt gattcttctg ctggttgatg tcgtttacat ttttttttgac     540 attaagttgc ttaggaatat tcccagatgg acacatttac ttcgacttct acgacttatt     600
attctgttaa gaattttcca tctgtttcat caaaaaagac aacttgaaaa gctgataaga     660
aggcgggttt cagaaaacaa aaggcgatac acaagggatg gatttgacct agacctcact     720
tacgttacag aacgtattat tgctatgtca tttccatctt ctggaaggca gtctttctat     780
agaaatccaa tcaaggaagt gtgtgcggttt ctagataaga aacaccgaaa ccactatcga    840
gtctacaatc tatgcagtga aagagcttac gatcctaagc acttccataa tagggtcgtt     900
agaatcatga ttgatgatca taatgtcccc actctacatc agatggtggt tttcaccaag     960
gaagtaaatg agtggatggc tcaagatctt gaaaacatcg tagcgattca ctgtaaagga     1020
ggcacaggtt atgtacgtga tctaaaaatc caaatagaaa tggagaaaaa ggttgtcttt     1080
tccactattt cattaggaaa atgttcggta cttgataaca ttacaacaga caaaatatta     1140
attgatgtat tcgacggtcc acctctgtat gatgatgtga aagtgcagtt tttctattcg     1200
aatcttccta catactatga caattgctca ttttacttct ggttgcacac atcttttatt     1260
gaaaataaca ggctttatct accaaaaaat gaattggata atctacataa acaaaaagca     1320
cggagaattt atccatcaga ttttgccgtg gagatacttt ttggcgagaa aatgacttcc     1380
agtgatgttg tagctggatc cgattaa                                         1407

<210> SEQ ID NO 56
<211> LENGTH: 1413
<212> TYPE: DNA
<213> ORGANISM: Homo sapiens

<400> SEQUENCE: 56
atgaatgaaa gtcctgatcc gactgacctg gcgggagtca tcattgagct cggccccaat     60
gacagtccac agacaagtga atttaaagga gcaaccgagg aggcacctgc gaaagaaagt     120
gtgttagcac gactttccaa gtttgaagtt gaagatgctg aaaatgttgc ttcatatgac     180
agcaagatta gaaaattgt gcattcaatt gtatcatcct ttgcatttgg actatttgga     240
gttttcctgg tcttactgga tgtcactctc atccttgccg acctaatttt cactgacagc     300
aaactttata ttcctttgga gtatcgttct atttctctag ctattgcctt ttttttttctc    360 atggatgttc ttcttcgagt atttgtagaa aggagacagc agtatttttc tgacttatttt   420 aacattttag atactgccat tattgtgatt cttctgctgg ttgatgtcgt ttacattttt     480
tttgacatta agttgcttag gaatattccc agatggacac atttacttcg acttctacga    540
cttattattc tgttaagaat ttttcatctg tttcatcaaa aaagacaact tgaaaagctg    600
ataagaaggc gggtttcaga aaacaaaagg cgatacacaa gggatggatt tgacctagac    660
ctcacttacg ttacagaacg tattattgct atgtcatttc catcttctgg aaggcagtct    720
ttctatagaa atccaatcaa ggaagttgtg cggtttctag ataagaaaca ccgaaaccac   780
tatcgagtct acaatctatg cagtgaaaga gcttacgatc ctaagcactt ccataatagg    840
gtcgttagaa tcatgattga tgatcataat gtccccactc tacatcagat ggtggttttc    900
accaaggaag taaatgagtg gatggctcaa gatcttgaaa acatcgtagc gattcactgt    960
aaaggaggca cagatagaac aggaactatg gtttgtgcct tccttattgc ctctgaaata    1020
```

```
tgttcaactg caaaggaaag cctgtattat tttggagaaa ggcgaacaga taaaacccac    1080
agcgaaaaat ttcagggagt agaaactcct tctgtacttg ataacattac aacagacaaa    1140
atattaattg atgtattcga cggtccacct ctgtatgatg atgtgaaagt gcagttttc     1200 tattcgaatc ttcctacata ctatgacaat tgctcatttt acttctggtt gcacacatct    1260
tttattgaaa ataacaggct ttatctacca aaaatgaat tggataatct acataaacaa     1320
aaagcacgga gaatttatcc atcagatttt gccgtggaga tacttttggg cgagaaaatg    1380
acttccagtg atgttgtagc tggatccgat taa                                 1413
```

<210> SEQ ID NO 57
<211> LENGTH: 1353
<212> TYPE: DNA
<213> ORGANISM: Homo sapiens

<400> SEQUENCE: 57

```
atgaatgaaa gtcctgatcc gactgacctg gcgggagtca tcattgagct cggccccaat    60
gacagtccac agacaagtga atttaaagga gcaaccgagg aggcacctgc gaaagaaagt    120
gtgttagcac gactttccaa gtttgaagtt gaagatgctg aaaatgttgc ttcatatgac    180
agcaagatta agaaaattgt gcattcaatt gtatcatcct ttgcatttgg actatttgga    240
gttttcctgg tcttactgga tgtcactctc atccttgccg acctaatttt cactgacagc    300
aaactttata ttcctttgga gtatcgttct atttctctag ctattgcctt attttttctc    360
atggatgttc ttcttcgagt atttgtagaa aggagacagc agtatttttc tgacttattt    420
aacattttag atactgccat tattgtgatt cttctgctgg ttgatgtcgt ttacattttt    480
tttgacatta agttgcttag gaatattccc agatggacac atttacttcg acttctacga    540
cttattattc tgttaagaat ttttcatctg tttcatcaaa aaagacaact tgaaaagctg    600
ataagaaggc gggtttcaga aaacaaaagg cgatacacaa gggatggatt tgacctagac    660
ctcacttacg ttacagaacg tattattgct atgtcatttc catcttctgg aaggcagtct    720
ttctatagaa atccaatcaa ggaagttgtg cggtttctag ataagaaaca ccgaaaccac    780
tatcgagtct acaatctatg cagtgaaaga gcttacgatc ctaagcactt ccataatagg    840
gtcgttagaa tcatgattga tgatcataat gtccccactc tacatcagat ggtggttttc    900
accaaggaag taaatgagtg gatggctcaa gatcttgaaa acatcgtagc gattcactgt    960
aaaggaggca caggttatgt acgtgatcta aaaatccaaa tagaaatgga gaaaaaggtt   1020
gtcttttcca ctatttcatt aggaaaatgt tcggtacttg ataacattac aacagacaaa   1080
atattaattg atgtattcga cggtccacct ctgtatgatg atgtgaaagt gcagttttc    1140 tattcgaatc ttcctacata ctatgacaat tgctcatttt acttctggtt gcacacatct   1200
tttattgaaa ataacaggct ttatctacca aaaatgaat tggataatct acataaacaa    1260
aaagcacgga gaatttatcc atcagatttt gccgtggaga tacttttggg cgagaaaatg   1320
acttccagtg atgttgtagc tggatccgat taa                                 1353
```

<210> SEQ ID NO 58
<211> LENGTH: 395
<212> TYPE: PRT
<213> ORGANISM: Homo sapiens

<400> SEQUENCE: 58

```
Met Asn Glu Ser Pro Asp Pro Thr Asp Leu Ala Gly Val Ile Ile Glu
1               5                   10                  15
```

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Arg Ile Met Ile
    290                 295                 300

Asp Asp His Asn Val Pro Thr Leu His Gln Met Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
            340                 345                 350

Leu Ile Ala Ser Glu Ile Cys Ser Thr Ala Lys Glu Ser Leu Tyr Tyr
        355                 360                 365

Phe Gly Glu Arg Arg Thr Asp Lys Thr His Ser Glu Lys Phe Gln Gly
    370                 375                 380

Val Glu Thr Pro Ser Gln Val Met Tyr Val Ile
385                 390                 395

<210> SEQ ID NO 59
<211> LENGTH: 468
<212> TYPE: PRT
<213> ORGANISM: Homo sapiens

```
<400> SEQUENCE: 59

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Gly Tyr Val Arg Asp Leu Lys Ile Gln Ile
            340                 345                 350

Glu Met Glu Lys Lys Val Val Phe Ser Thr Ile Ser Leu Gly Lys Cys
        355                 360                 365

Ser Val Leu Asp Asn Ile Thr Thr Asp Lys Ile Leu Ile Asp Val Phe
    370                 375                 380

Asp Gly Pro Pro Leu Tyr Asp Asp Val Lys Val Gln Phe Phe Tyr Ser
385                 390                 395                 400

Asn Leu Pro Thr Tyr Tyr Asp Asn Cys Ser Phe Tyr Phe Trp Leu His
                405                 410                 415
```

```
Thr Ser Phe Ile Glu Asn Asn Arg Leu Tyr Leu Pro Lys Asn Glu Leu
            420                 425                 430

Asp Asn Leu His Lys Gln Lys Ala Arg Arg Ile Tyr Pro Ser Asp Phe
            435                 440                 445

Ala Val Glu Ile Leu Phe Gly Glu Lys Met Thr Ser Ser Asp Val Val
450                 455                 460

Ala Gly Ser Asp
465

<210> SEQ ID NO 60
<211> LENGTH: 470
<212> TYPE: PRT
<213> ORGANISM: Homo sapiens

<400> SEQUENCE: 60

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
                20                  25                  30

Glu Glu Ala Pro Ala Lys Glu Ser Val Leu Ala Arg Leu Ser Lys Phe
            35                  40                  45

Glu Val Glu Asp Ala Glu Asn Val Ala Ser Tyr Asp Ser Lys Ile Lys
        50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
                100                 105                 110

Leu Ala Ile Ala Leu Phe Phe Leu Met Asp Val Leu Leu Arg Val Phe
            115                 120                 125

Val Glu Arg Arg Gln Gln Tyr Phe Ser Asp Leu Phe Asn Ile Leu Asp
        130                 135                 140

Thr Ala Ile Ile Val Ile Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Val Ser Glu Asn
        195                 200                 205

Lys Arg Arg Tyr Thr Arg Asp Gly Phe Asp Leu Asp Leu Thr Tyr Val
        210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Arg Ile Met Ile Asp Asp
        275                 280                 285

His Asn Val Pro Thr Leu His Gln Met Val Val Phe Thr Lys Glu Val
        290                 295                 300

Asn Glu Trp Met Ala Gln Asp Leu Glu Asn Ile Val Ala Ile His Cys
```

```
            305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
                340                 345                 350

Glu Arg Arg Thr Asp Lys Thr His Ser Glu Lys Phe Gln Gly Val Glu
                355                 360                 365

Thr Pro Ser Val Leu Asp Asn Ile Thr Thr Asp Lys Ile Leu Ile Asp
            370                 375                 380

Val Phe Asp Gly Pro Pro Leu Tyr Asp Val Lys Val Gln Phe Phe
385                 390                 395                 400

Tyr Ser Asn Leu Pro Thr Tyr Tyr Asp Asn Cys Ser Phe Tyr Phe Trp
                405                 410                 415

Leu His Thr Ser Phe Ile Glu Asn Asn Arg Leu Tyr Leu Pro Lys Asn
                420                 425                 430

Glu Leu Asp Asn Leu His Lys Gln Lys Ala Arg Arg Ile Tyr Pro Ser
                435                 440                 445

Asp Phe Ala Val Glu Ile Leu Phe Gly Glu Lys Met Thr Ser Ser Asp
                450                 455                 460

Val Val Ala Gly Ser Asp
465                 470

<210> SEQ ID NO 61
<211> LENGTH: 450
<212> TYPE: PRT
<213> ORGANISM: Homo sapiens

<400> SEQUENCE: 61

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
                20                  25                  30

Glu Glu Ala Pro Ala Lys Glu Ser Val Leu Ala Arg Leu Ser Lys Phe
            35                  40                  45

Glu Val Glu Asp Ala Glu Asn Val Ala Ser Tyr Asp Ser Lys Ile Lys
        50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
                100                 105                 110

Leu Ala Ile Ala Leu Phe Phe Leu Met Asp Val Leu Leu Arg Val Phe
            115                 120                 125

Val Glu Arg Arg Gln Gln Tyr Phe Ser Asp Leu Phe Asn Ile Leu Asp
        130                 135                 140

Thr Ala Ile Ile Val Ile Leu Leu Val Asp Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
                180                 185                 190

Gln Lys Arg Gln Leu Glu Lys Leu Ile Arg Arg Val Ser Glu Asn
                195                 200                 205
```

```
Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Gly Tyr Val Arg Asp Leu Lys Ile Gln Ile Glu Met
                325                 330                 335

Glu Lys Lys Val Val Phe Ser Thr Ile Ser Leu Gly Lys Cys Ser Val
            340                 345                 350

Leu Asp Asn Ile Thr Thr Asp Lys Ile Leu Ile Asp Val Phe Asp Gly
        355                 360                 365

Pro Pro Leu Tyr Asp Asp Val Lys Val Gln Phe Phe Tyr Ser Asn Leu
    370                 375                 380

Pro Thr Tyr Tyr Asp Asn Cys Ser Phe Tyr Phe Trp Leu His Thr Ser
385                 390                 395                 400

Phe Ile Glu Asn Asn Arg Leu Tyr Leu Pro Lys Asn Glu Leu Asp Asn
                405                 410                 415

Leu His Lys Gln Lys Ala Arg Arg Ile Tyr Pro Ser Asp Phe Ala Val
            420                 425                 430

Glu Ile Leu Phe Gly Glu Lys Met Thr Ser Ser Asp Val Val Ala Gly
        435                 440                 445

Ser Asp
    450

<210> SEQ ID NO 62
<211> LENGTH: 1299
<212> TYPE: DNA
<213> ORGANISM: Homo sapiens

<400> SEQUENCE: 62
cgcccttaga catggctcag atgtgcagcc acagtgagct tctgaacatt tcttctcaga      60
ctaagctctt acacacagtt gcagttgaaa gaaagaattg cttgacatgg ccacaggagc     120
aggcagcttc ctgcagacat gacagtcaac gcaaactcat gtcactgtgg gcagacacat     180
gtttgcaaag agactcagag ccaaacaagc acactcaatg tgctttgccc aaatttaccc     240
attaggtaaa tcttccctcc tcccaagaag aaagtggaga gagcatgagt cctcacatgg     300
gaacttgaag tcagggaaat gaaggctcac caattatttg tgcatgggtt taagttttcc     360
ttgaaattaa gttcaggttt gtctttgtgt gtaccaatta atgacaagag gttagataga     420
agtatgctag atggcaaaga gaaatatgtt ttgtgtcttc aattttgcta aaaataaccc     480
agaacatgga taattcattt attaattgat tttggtaagc caagtcctat ttggagaaaa     540
ttaatagttt ttctaaaaaa gaattttctc aatatcacct ggcttgataa cattttctc      600 cttcgagttc cttttctgg agtttaacaa acttgttctt tacaaataga ttatattgac       660
tacctctcac tgatgttatg atattagttt ctattgctta ctttgtattt ctaattttag     720
```

```
gattcacaat ttagctggag aactatttt  taacctgttg cacctaaaca tgattgagct      780
agaagacagt tttaccatat gcatgcattt tctctgagtt atattttaaa atctatacat      840
ttctcctaaa tatggaggaa atcactggca tcaaatgcca gtctcagacg aagacctaa       900 agcccatttc tggcctggag ctacttggct ttgtgaccta tggtgaggca taagtgctct      960
gagtttgtgt tgcctctttt gtaaaatgag ggtttgactt aatcagtgat tttcatagct     1020 taaaatttt  ttgaagaaca gaactttttt taaaaacagt tagatgcaac catattatat     1080
aaaacagaac agatacaagt agagctaact tgctaaagaa aggatggagg ctctgaagct     1140
gtgacttcat tatcccttaa tactgctatg tcctctgtag taccttagat ttctatggga     1200
catcgtttaa aaactattgt ttatgcgaga gccttgctaa tttcctaaaa attgtggata     1260
cattttttct cccatgtata attttctcac cttctattt                            1299
```

<210> SEQ ID NO 63
<211> LENGTH: 405
<212> TYPE: DNA
<213> ORGANISM: Homo sapiens

<400> SEQUENCE: 63

```
gcacaaggcc tgctcttact ccaaaaagat ggacccaggt ccgaaggggc actgccactg       60 tgggggcat  ggccatcctc caggtcactg cgggccaccc cctggccatg gcccagggcc      120
ctgcgggcca cccccacca  tggtccaggg ccctgcgggc caccccctgg ccatggccca      180
gggccctgcg ggccaccccc ccaccatggt ccagggccct gcgggcctcc ccctggccat      240
ggcccaggtc acccacccc  tggtccacat cactgaggaa gtagaagaaa acaggacaca      300
agatggcaag cctgagagaa ttgcccagct gacctggaat gaggcctaaa ccacaatctt      360
ctcttcctaa taaacagcct cctagaggcc acattctatt ctgta                     405
```

<210> SEQ ID NO 64
<211> LENGTH: 106
<212> TYPE: PRT
<213> ORGANISM: Homo sapiens

<400> SEQUENCE: 64

```
Met Asp Pro Gly Pro Lys Gly His Cys His Cys Gly Gly His Gly His
1               5                   10                  15

Pro Pro Gly His Cys Gly Pro Pro Gly His Gly Pro Gly Pro Cys
            20                  25                  30

Gly Pro Pro Thr Met Val Gln Gly Pro Ala Gly His Pro Leu Ala
        35                  40                  45

Met Ala Gln Gly Pro Ala Gly His Pro Pro Thr Met Val Gln Gly Pro
50                  55                  60

Ala Gly Leu Pro Leu Ala Met Ala Gln Val Thr His Pro Leu Val His
65                  70                  75                  80

Ile Thr Glu Glu Val Glu Glu Asn Arg Thr Gln Asp Gly Lys Pro Glu
                85                  90                  95

Arg Ile Ala Gln Leu Thr Trp Asn Glu Ala
            100                 105
```

<210> SEQ ID NO 65
<211> LENGTH: 71
<212> TYPE: PRT
<213> ORGANISM: Homo sapiens

<400> SEQUENCE: 65

```
Met Ala Ile Leu Gln Val Thr Ala Gly His Pro Leu Ala Met Ala Gln
1               5                   10                  15

Gly Pro Ala Gly His Pro Pro Trp Ser Arg Ala Leu Arg Ala Thr
            20                  25                  30

Pro Trp Pro Trp Pro Arg Ala Leu Arg Ala Thr Pro Pro Trp Ser
        35                  40                  45

Arg Ala Leu Arg Ala Ser Pro Trp Pro Trp Arg Ser Pro Thr Pro
        50                  55                  60

Trp Ser Thr Ser Leu Arg Lys
65                  70

<210> SEQ ID NO 66
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 66
agacatggct cagatgtgca g                                         21

<210> SEQ ID NO 67
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 67
ggaaattagc aaggctctcg c                                         21

<210> SEQ ID NO 68
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 68
tcaggtattc cctgctctta c                                         21

<210> SEQ ID NO 69
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 69
tgggcaattc tctcaggctt g                                         21

<210> SEQ ID NO 70
<211> LENGTH: 908
<212> TYPE: DNA
<213> ORGANISM: Homo sapiens

<400> SEQUENCE: 70
aaaattcggc acgaggccgg gctgtggtct agcataaagg cggagcccag aagaaggggc    60
ggggtatggg agaagcctcc ccacctgccc ccgcaaggcg gcatctgctg gtcctgctgc   120
```

```
tgctcctctc taccctggtg atcccctccg ctgcagctcc tatccatgat gctgacgccc      180
aagagagctc cttgggtctc acaggcctcc agagcctact ccaaggcttc agccgacttt      240
tcctgaaagg taacctgctt cggggcatag acagcttatt ctctgccccc atggacttcc      300
ggggcctccc tgggaactac cacaaagagg agaaccagga gcaccagctg ggaacaaca       360 ccctctccag ccacctccag atcgacaaga tgaccgacaa caagacagga gaggtgctga      420
tctccgagaa tgtggtggca tccattcaac cagcggaggg gagcttcgag ggtgatttga      480
aggtacccag gatggaggag aaggaggccc tggtacccat ccagaaggcc acggacagct      540
tccacacaga actccatccc cgggtggcct tctggatcat taagctgcca cggcggaggt      600
cccaccagga tgccctggag ggcggccact ggctcagcga aagcgacac cgcctgcagg       660 ccatccggga tggactccgc aaggggaccc acaaggacgt cctagaagag gggaccgaga      720
gctcctccca ctccaggctg tccccccgaa agacccactt actgtacatc ctcaggccct      780
ctcggcagct gtaggggtgg ggaccgggga gcacctgcct gtagccccca tcagaccctg      840
ccccaagcac catatggaaa taaagttctt tcttacatct aaaaaaaaaa aaaaaaaaa      900 aaaaaaaa                                                                 908
```

<210> SEQ ID NO 71
<211> LENGTH: 242
<212> TYPE: PRT
<213> ORGANISM: Homo sapiens

<400> SEQUENCE: 71

```
Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Gly Asn Leu
    50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
            100                 105                 110

Lys Thr Gly Glu Val Leu Ile Ser Glu Asn Val Val Ala Ser Ile Gln
        115                 120                 125

Pro Ala Glu Gly Ser Phe Glu Gly Asp Leu Lys Val Pro Arg Met Glu
    130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Gly His Trp Leu Ser Glu
            180                 185                 190

Lys Arg His Arg Leu Gln Ala Ile Arg Asp Gly Leu Arg Lys Gly Thr
        195                 200                 205

His Lys Asp Val Leu Glu Glu Gly Thr Glu Ser Ser Ser His Ser Arg
    210                 215                 220
```

Leu Ser Pro Arg Lys Thr His Leu Leu Tyr Ile Leu Arg Pro Ser Arg
225                 230                 235                 240

Gln Leu

<210> SEQ ID NO 72
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 72
ctcctatcca tgatgctgac g                                         21

<210> SEQ ID NO 73
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 73
cctgaggatg tacagtaagt g                                         21

<210> SEQ ID NO 74
<211> LENGTH: 2987
<212> TYPE: DNA
<213> ORGANISM: Homo sapiens

<400> SEQUENCE: 74
tttcccagcg aggtggtcat tcagagccta cacatctgtt ctgtattta acccatggat      60 gagaatattc attcaagcca agagagttaa aactaaacat ctttgctatt gcctctacag     120
acccagaaag tatctttatg tcacatcttc ttttaaagga gcatttaaag atgaagttaa     180
aaaggcagaa gaagcagtaa agattgctga atccatattg aaagaagcac aaatcaaagt     240
aaaccagtgt gacagaacct ctttatcttc tgccaaggat gtattacaga gagctttgga     300
agatgtagaa gcaaagcaaa agaatcttaa agagaaacaa agagaattaa aaacagcaag     360
aacgctctcc ctgttctatg gagtgaacgt agaaaaccga agccaagctg gaatgttcat     420
ttacagtaat aaccgtttga tcaaaatgca tgaaaaagtg ggctcacagt tgaaactgaa     480
gtccttactt ggcgcaggcg tggttggaat tgttaatata cccttggagg tcatggaacc     540
atcccataat aaacaggaat ttctcaatgt ccaagatgat aatcatctac taaaagtcat     600
gggacagtac ttggtccagt actgtaagga caccggcatc aataatagaa atttaacatt     660
gttttgcaat gaatttggat accagaatga catcgatgtg gagaaacctt taaattcttt     720
tcaatatcaa agaagacaag ccatgggtat cccattcatc atacaatgtg atctttgtct     780
taaatggaga gtcttgcctt cctctactaa ttatcaggaa aaagaatttt ttgacatttg     840
gatttgtgct aataatccca accgcttgga aaacagttgt catcaggtag aatgtctacc     900
ttccatccca ctgggcacca tgagcacaat atcaccatca aaaatgagaa aagaaagca     960 acttagagag tcggtcataa agtatcaaaa tagactggca gaacagcagc cacagcctca    1020
atttatacca gtggacgaaa tcactgtcac ttccacctgc ctaacttcag cacataagga    1080
aaataccaaa acccagaaaa tcaggctttt gggcgatgac ttgaagcatg aatctctttc    1140
atcctttgag ctttcagcga gccgtagagg acagaaaaga aacatagaag agacagactc    1200

```
tgatgtagag tatatttcag aaacaaaaat tatgaaaaag tctatggagg agaaaatgaa    1260
ctctcaacag cagagaattc cagtagctct gccagaaaat gtcaaactag ctgagagatc    1320
ccagagaagt cagattgcta atattaccac tgtctggaga gctcaaccaa ctgaagggtg    1380
cctgaagaat gcccaggccg cttcttggga aatgaaaagg aagcagagtc tgaactttgt    1440
agaggaatgt aaggtattga ctgaagatga aacacgagt gattcagata taatcctggt     1500
ttcagataaa agcaacactg atgtttcatt gaaacaagaa aaaaggaaa ttcctctttt      1560 aaaccaagaa aaacaggagc tgtgcaatga tgttctagca atgaaaagaa gctcttcatt    1620
acctagctgg aaaagcttgc tcaatgtgcc gatggaagat gtgaatctaa gttctggaca    1680
catagccaga gtttctgtga gtggcagttg taaagttgct tcttcgccag cgtcttctca    1740
aagcacacct gtcaaggaaa cagtgagaaa actgaagtct aagttaaggg agattcttct    1800 gtatttttt cctgagcatc agctaccatc agaattggaa gaacctgcat taagttgtga    1860
gctggagcag tgcccagagc agatgaacaa aaagctgaaa atgtgtttca accagataca    1920
gaatacttac atggtccaat atgaaaaaaa aataaagagg aaattgcagt ccattatcta    1980
tgattcaaat acaagaggaa tacataatga aatctctctg gggcaatgtg aaaataaaag    2040
aaaaatctct gaggataagc tgaagaatct tcgtataaaa ctggcactat tgttgcagaa    2100
actccaactg ggtggtccag aaggtgacct ggagcagact gacacttatt tagaagcttt    2160
gcttaaagaa gataatcttc tcttccagaa caatttaaat aaagtaacta tagatgcaag    2220
acatagactc cctttagaaa aaaatgaaaa gacttcggaa aattaagtca gagatggtat    2280
taccttttaa aaaatgctaa taagaaaatt ggaagattct tttaaaaatt tttcttttt      2340 gttgttgtta ctgtaaagtc tattctgttt aacaataaga aataagaaat aattttttc      2400 aaataagaaa attgtgtact ctagaaatgg agaccgattt acaatttatg tattccctaa    2460
tccaattatc taaatcttcc ttttctttca gaaatattaa taatatctag agttctctaa    2520
ttttcatgtg agctactgaa aaaaatgaaa atgtcactca agcttaactt ttgttattcc    2580
ttaaaagatt gttattgtaa ttttgttatt ccttaaaaac atttaaaagc agatttttc     2640 aaaatcgata tgtgaaggac tacagaatca cctcctcttg aagatattga aaagaaaga    2700 cattatgccc tttctccact atagccaaca ctcagtcaag cagaaaatac aaatccccc    2760 aaaactttga gacatagctt atataatttt attatttagt catagtaaaa gaataaatct    2820
cctaagcata atatgtatac atattacaca tatgtaaaaa ttgttgtttt acatttacat    2880
atacgtaaag aagtatgttt ttacacttttt cttgataagt gttttttttt tgtttagaaa    2940
tgtctgaaac tttagacaaa aacagtaaaa catttaatat tcatttg                  2987
```

<210> SEQ ID NO 75
<211> LENGTH: 735
<212> TYPE: PRT
<213> ORGANISM: Homo sapiens

<400> SEQUENCE: 75

```
Met Arg Ile Phe Ile Gln Ala Lys Arg Val Lys Thr Lys His Leu Cys
1               5                   10                  15

Tyr Cys Leu Tyr Arg Pro Arg Lys Tyr Leu Tyr Val Thr Ser Ser Phe
            20                  25                  30

Lys Gly Ala Phe Lys Asp Glu Val Lys Ala Glu Glu Ala Val Lys
        35                  40                  45

Ile Ala Glu Ser Ile Leu Lys Glu Ala Gln Ile Lys Val Asn Gln Cys
    50                  55                  60
```

-continued

```
Asp Arg Thr Ser Leu Ser Ser Ala Lys Asp Val Leu Gln Arg Ala Leu
 65                  70                  75                  80

Glu Asp Val Glu Ala Lys Gln Lys Asn Leu Lys Glu Lys Gln Arg Glu
                 85                  90                  95

Leu Lys Thr Ala Arg Thr Leu Ser Leu Phe Tyr Gly Val Asn Val Glu
            100                 105                 110

Asn Arg Ser Gln Ala Gly Met Phe Ile Tyr Ser Asn Asn Arg Leu Ile
        115                 120                 125

Lys Met His Glu Lys Val Gly Ser Gln Leu Lys Leu Lys Ser Leu Leu
130                 135                 140

Gly Ala Gly Val Val Gly Ile Val Asn Ile Pro Leu Glu Val Met Glu
145                 150                 155                 160

Pro Ser His Asn Lys Gln Glu Phe Leu Asn Val Gln Glu Tyr Asn His
                165                 170                 175

Leu Leu Lys Val Met Gly Gln Tyr Leu Val Gln Tyr Cys Lys Asp Thr
            180                 185                 190

Gly Ile Asn Asn Arg Asn Leu Thr Leu Phe Cys Asn Glu Phe Gly Tyr
        195                 200                 205

Gln Asn Asp Ile Asp Val Glu Lys Pro Leu Asn Ser Phe Gln Tyr Gln
210                 215                 220

Arg Arg Gln Ala Met Gly Ile Pro Phe Ile Ile Gln Cys Asp Leu Cys
225                 230                 235                 240

Leu Lys Trp Arg Val Leu Pro Ser Ser Thr Asn Tyr Gln Glu Lys Glu
                245                 250                 255

Phe Phe Asp Ile Trp Ile Cys Ala Asn Asn Pro Asn Arg Leu Glu Asn
            260                 265                 270

Ser Cys His Gln Val Glu Cys Leu Pro Ser Ile Pro Leu Gly Thr Met
        275                 280                 285

Ser Thr Ile Ser Pro Ser Lys Asn Glu Lys Glu Lys Gln Leu Arg Glu
290                 295                 300

Ser Val Ile Lys Tyr Gln Asn Arg Leu Ala Glu Gln Gln Pro Gln Pro
305                 310                 315                 320

Gln Phe Ile Pro Val Asp Glu Ile Thr Val Thr Ser Thr Cys Leu Thr
                325                 330                 335

Ser Ala His Lys Glu Asn Thr Lys Thr Gln Lys Ile Arg Leu Leu Gly
            340                 345                 350

Asp Asp Leu Lys His Glu Ser Leu Ser Ser Phe Glu Leu Ser Ala Ser
        355                 360                 365

Arg Arg Gly Gln Lys Arg Asn Ile Glu Glu Thr Asp Ser Asp Val Glu
370                 375                 380

Tyr Ile Ser Glu Thr Lys Ile Met Lys Lys Ser Met Glu Glu Lys Met
385                 390                 395                 400

Asn Ser Gln Gln Gln Arg Ile Pro Val Ala Leu Pro Glu Asn Val Lys
                405                 410                 415

Leu Ala Glu Arg Ser Gln Arg Ser Gln Ile Ala Asn Ile Thr Thr Val
            420                 425                 430

Trp Arg Ala Gln Pro Thr Glu Gly Cys Leu Lys Asn Ala Gln Ala Ala
        435                 440                 445

Ser Trp Glu Met Lys Arg Lys Gln Ser Leu Asn Phe Val Glu Glu Cys
450                 455                 460

Lys Val Leu Thr Glu Asp Glu Asn Thr Ser Asp Ser Asp Ile Ile Leu
465                 470                 475                 480
```

```
Val Ser Asp Lys Ser Asn Thr Asp Val Ser Leu Lys Gln Glu Lys Lys
                485                 490                 495

Glu Ile Pro Leu Leu Asn Gln Glu Lys Gln Glu Leu Cys Asn Asp Val
            500                 505                 510

Leu Ala Met Lys Arg Ser Ser Ser Leu Pro Ser Trp Lys Ser Leu Leu
        515                 520                 525

Asn Val Pro Met Glu Asp Val Asn Leu Ser Ser Gly His Ile Ala Arg
    530                 535                 540

Val Ser Val Ser Gly Ser Cys Lys Val Ala Ser Ser Pro Ala Ser Ser
545                 550                 555                 560

Gln Ser Thr Pro Val Lys Glu Thr Val Arg Lys Leu Lys Ser Lys Leu
                565                 570                 575

Arg Glu Ile Leu Leu Tyr Phe Phe Pro Glu His Gln Leu Pro Ser Glu
            580                 585                 590

Leu Glu Glu Pro Ala Leu Ser Cys Glu Leu Glu Gln Cys Pro Glu Gln
        595                 600                 605

Met Asn Lys Lys Leu Lys Met Cys Phe Asn Gln Ile Gln Asn Thr Tyr
    610                 615                 620

Met Val Gln Tyr Glu Lys Lys Ile Lys Arg Lys Leu Gln Ser Ile Ile
625                 630                 635                 640

Tyr Asp Ser Asn Thr Arg Gly Ile His Asn Glu Ile Ser Leu Gly Gln
                645                 650                 655

Cys Glu Asn Lys Arg Lys Ile Ser Glu Asp Lys Leu Lys Asn Leu Arg
            660                 665                 670

Ile Lys Leu Ala Leu Leu Leu Gln Lys Leu Gln Leu Gly Gly Pro Glu
        675                 680                 685

Gly Asp Leu Glu Gln Thr Asp Thr Tyr Leu Glu Ala Leu Leu Lys Glu
    690                 695                 700

Asp Asn Leu Leu Phe Gln Asn Asn Leu Asn Lys Val Thr Ile Asp Ala
705                 710                 715                 720

Arg His Arg Leu Pro Leu Glu Lys Asn Glu Lys Thr Ser Glu Asn
                725                 730                 735

<210> SEQ ID NO 76
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 76
ctgagtatca gctaccatca g                                              21

<210> SEQ ID NO 77
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 77
tctgtagtcc ttcacatatc g                                              21

<210> SEQ ID NO 78
<211> LENGTH: 21
<212> TYPE: DNA
<213> ORGANISM: Artificial Seqeunce
```

```
<220> FEATURE:
<223> OTHER INFORMATION: Description of the artificial sequence:
      Oligonucleotide

<400> SEQUENCE: 78
ttttgtctat ggtgtaggac c                                              21

<210> SEQ ID NO 79
<211> LENGTH: 21
<212> TYPE: DNA
<213> ORGANISM: Artificial Sequence
<220> FEATURE:
<223> OTHER INFORMATION: Description of the artificial sequence:
      Oligonucleotide

<400> SEQUENCE: 79
ggaatggcaa tgatgttaca g                                              21

<210> SEQ ID NO 80
<211> LENGTH: 20
<212> TYPE: PRT
<213> ORGANISM: Homo sapiens

<400> SEQUENCE: 80

Met Ser Thr Val Lys Glu Gln Leu Ile Glu Lys Leu Ile Glu Asp Asp
1               5                   10                  15
Glu Asn Ser Gln
            20

<210> SEQ ID NO 81
<211> LENGTH: 14
<212> TYPE: PRT
<213> ORGANISM: Homo sapiens

<400> SEQUENCE: 81

Phe Thr Asp Ser Lys Leu Tyr Ile Pro Leu Glu Tyr Arg Ser
1               5                   10

<210> SEQ ID NO 82
<211> LENGTH: 13
<212> TYPE: PRT
<213> ORGANISM: Homo sapiens

<400> SEQUENCE: 82

Phe Asp Ile Lys Leu Leu Arg Asn Ile Pro Arg Trp Thr
1               5                   10

<210> SEQ ID NO 83
<211> LENGTH: 15
<212> TYPE: PRT
<213> ORGANISM: Homo sapiens

<400> SEQUENCE: 83

Gly Val Ala Gly Gln Asp Tyr Trp Ala Val Leu Ser Gly Lys Gly
1               5                   10                  15

<210> SEQ ID NO 84
<211> LENGTH: 10
<212> TYPE: PRT
<213> ORGANISM: Homo sapiens

<400> SEQUENCE: 84

Ser Arg Glu Val Thr Thr Asn Ala Gln Arg
1               5                   10
```

<210> SEQ ID NO 85
<211> LENGTH: 216
<212> TYPE: DNA
<213> ORGANISM: Homo sapiens

<400> SEQUENCE: 85

| tgctcttact ccaaaaagat ggacccaggg ccctgcgggc ctcccctgg ccatggccca | 60 |
| ggtcacccac ccctggtcc acatcactga ggaagtagaa gaaaacagga cacaagatgg | 120 |
| caagcctgag agaattgccc agctgacctg gaaggaggcc taaaccgcaa tattctcttc | 180 |
| ctaataaaca gcctcctaga ggccacattc tattct | 216 |

<210> SEQ ID NO 86
<211> LENGTH: 227
<212> TYPE: DNA
<213> ORGANISM: Homo sapiens

<400> SEQUENCE: 86

| tgctcttact ccaaaaagat ggacccaggt ccgaaggggc actgccactg tgggggcat | 60 |
| ggccatcctc caggtcaccc accccctggt ccacatcact gaggaagtag aagaaaacag | 120 |
| gacacaagat ggcaagcctg agagaattgc ccagctgacc tggaatgagg cctaaaccac | 180 |
| aatcttctct tcctaataaa cagcctccta gaggccacat tctattc | 227 |

<210> SEQ ID NO 87
<211> LENGTH: 261
<212> TYPE: DNA
<213> ORGANISM: Homo sapiens

<400> SEQUENCE: 87

| tgctcttact ccaaaaagat ggacccaggt ccgaaggggc actgccactg tgggggcat | 60 |
| ggccatcctc caggtcactg cgggcctccc cctggccatg gcccaggtca cccacccct | 120 |
| ggtccacatc actgaggaag tagaagaaaa caggacacaa gatggcaagc tgagagaat | 180 |
| tgcccagctg acctggaatg aggcctaaac cacaatcttc tcttcctaat aaacagcctc | 240 |
| ctagaggcca cattctattc t | 261 |

<210> SEQ ID NO 88
<211> LENGTH: 327
<212> TYPE: DNA
<213> ORGANISM: Homo sapiens

<400> SEQUENCE: 88

| tgctcttact ccaaaaagat ggacccaggt ccgaaggggc actgccactg tgggggcat | 60 |
| ggccatcctc caggtcactg cgggccaccc ccaccatg gtccagggcc ctgcgggcca | 120 |
| ccccccacc atggtccagg gcctgcgggc ctcccctg gccatggccc aggtcaccca | 180 |
| cccctggtc cacatcactg aggaagtaga agaaaacagg acacaagatg gcaagcctga | 240 |
| gagaattgcc cagctgacct ggaatgaggc ctaaaccaca atcttctctt cctaataaac | 300 |
| agcctcctag aggccacatt ctattct | 327 |

<210> SEQ ID NO 89
<211> LENGTH: 31
<212> TYPE: PRT
<213> ORGANISM: Homo sapiens

<400> SEQUENCE: 89

Leu Leu Leu Gln Lys Asp Gly Pro Arg Ala Leu Arg Ala Ser Pro Trp

```
1               5                   10                  15
Pro Trp Pro Arg Ser Pro Thr Pro Trp Ser Thr Ser Leu Arg Lys
                20                  25                  30

<210> SEQ ID NO 90
<211> LENGTH: 23
<212> TYPE: PRT
<213> ORGANISM: Homo sapiens

<400> SEQUENCE: 90

Met Asp Pro Gly Pro Cys Gly Pro Pro Gly His Gly Pro Gly His
1               5                   10                  15

Pro Pro Pro Gly Pro His His
                20

<210> SEQ ID NO 91
<211> LENGTH: 36
<212> TYPE: PRT
<213> ORGANISM: Homo sapiens

<400> SEQUENCE: 91

Met Ala Gln Val Thr His Pro Leu Val His Ile Thr Glu Glu Val Glu
1               5                   10                  15

Glu Asn Arg Thr Gln Asp Gly Lys Pro Glu Arg Ile Ala Gln Leu Thr
                20                  25                  30

Trp Lys Glu Ala
        35

<210> SEQ ID NO 92
<211> LENGTH: 34
<212> TYPE: PRT
<213> ORGANISM: Homo sapiens

<400> SEQUENCE: 92

Leu Leu Gln Lys Asp Gly Pro Arg Ser Glu Gly Ala Leu Pro Leu Trp
1               5                   10                  15

Gly Ala Trp Pro Ser Ser Arg Ser Pro Thr Pro Trp Ser Thr Ser Leu
                20                  25                  30

Arg Lys

<210> SEQ ID NO 93
<211> LENGTH: 27
<212> TYPE: PRT
<213> ORGANISM: Homo sapiens

<400> SEQUENCE: 93

Met Asp Pro Gly Pro Lys Gly His Cys His Cys Gly Gly His Gly His
1               5                   10                  15

Pro Pro Gly His Pro Pro Gly Pro His His
                20                  25

<210> SEQ ID NO 94
<211> LENGTH: 38
<212> TYPE: PRT
<213> ORGANISM: Homo sapiens

<400> SEQUENCE: 94

Met Ala Ile Leu Gln Val Thr His Pro Leu Val His Ile Thr Glu Glu
1               5                   10                  15

Val Glu Glu Asn Arg Thr Gln Asp Gly Lys Pro Glu Arg Ile Ala Gln
                20                  25                  30
```

```
Leu Thr Trp Asn Glu Ala
        35

<210> SEQ ID NO 95
<211> LENGTH: 46
<212> TYPE: PRT
<213> ORGANISM: Homo sapiens

<400> SEQUENCE: 95

Leu Leu Leu Gln Lys Asp Gly Pro Arg Ser Glu Gly Ala Leu Pro Leu
1               5                   10                  15

Trp Gly Ala Trp Pro Ser Ser Arg Ser Leu Arg Ala Ser Pro Trp Pro
            20                  25                  30

Trp Pro Arg Ser Pro Thr Pro Trp Ser Thr Ser Leu Arg Lys
        35                  40                  45

<210> SEQ ID NO 96
<211> LENGTH: 38
<212> TYPE: PRT
<213> ORGANISM: Homo sapiens

<400> SEQUENCE: 96

Met Asp Pro Gly Pro Lys Gly His Cys His Cys Gly His Gly His His
1               5                   10                  15

Pro Pro Gly His Cys Gly Pro Pro Gly His Gly Pro Gly His Pro
            20                  25                  30

Pro Pro Gly Pro His His
        35

<210> SEQ ID NO 97
<211> LENGTH: 49
<212> TYPE: PRT
<213> ORGANISM: Homo sapiens

<400> SEQUENCE: 97

Met Ala Ile Leu Gln Val Thr Ala Gly Leu Pro Leu Ala Met Ala Gln
1               5                   10                  15

Val Thr His Pro Leu Val His Ile Thr Glu Glu Val Glu Glu Asn Arg
            20                  25                  30

Thr Gln Asp Gly Lys Pro Glu Arg Ile Ala Gln Leu Thr Trp Asn Glu
        35                  40                  45

Ala

<210> SEQ ID NO 98
<211> LENGTH: 68
<212> TYPE: PRT
<213> ORGANISM: Homo sapiens

<400> SEQUENCE: 98

Leu Leu Leu Gln Lys Asp Gly Pro Arg Ser Glu Gly Ala Leu Pro Leu
1               5                   10                  15

Trp Gly Ala Trp Pro Ser Ser Arg Ser Leu Arg Ala Thr Pro Pro Pro
            20                  25                  30

Trp Ser Arg Ala Leu Arg Ala Thr Pro Pro Trp Ser Arg Ala Leu
        35                  40                  45

Arg Ala Ser Pro Trp Pro Trp Pro Arg Ser Pro Thr Pro Trp Ser Thr
    50                  55                  60

Ser Leu Arg Lys
65
```

<210> SEQ ID NO 99
<211> LENGTH: 60
<212> TYPE: PRT
<213> ORGANISM: Homo sapiens

<400> SEQUENCE: 99

Met Asp Pro Gly Pro Lys Gly His Cys His Cys Gly Gly His Gly His
1               5                   10                  15

Pro Pro Gly His Cys Gly Pro Pro Pro His His Gly Pro Gly Pro Cys
            20                  25                  30

Gly Pro Pro Pro His His Gly Pro Gly Pro Cys Gly Pro Pro Pro Gly
        35                  40                  45

His Gly Pro Gly His Pro Pro Pro Gly Pro His His
    50                  55                  60

<210> SEQ ID NO 100
<211> LENGTH: 71
<212> TYPE: PRT
<213> ORGANISM: Homo sapiens

<400> SEQUENCE: 100

Met Ala Ile Leu Gln Val Thr Ala Gly His Pro Pro Thr Met Val Gln
1               5                   10                  15

Gly Pro Ala Gly His Pro Pro Thr Met Val Gln Gly Pro Ala Gly Leu
            20                  25                  30

Pro Leu Ala Met Ala Gln Val Thr His Pro Leu Val His Ile Thr Glu
        35                  40                  45

Glu Val Glu Glu Asn Arg Thr Gln Asp Gly Lys Pro Glu Arg Ile Ala
    50                  55                  60

Gln Leu Thr Trp Asn Glu Ala
65                  70